United States Patent
Orlow et al.

(10) Patent No.: US 9,138,433 B2
(45) Date of Patent: Sep. 22, 2015

(54) INDOLE ALKALOID COMPOUNDS AS MELANOGENESIS PROMOTERS AND USES THEREOF

(75) Inventors: Seth J. Orlow, New York, NY (US); Li Ni Komatsu, Clarksville, MD (US)

(73) Assignee: NEW YORK UNIVERSITY, New York, NY (US)

( * ) Notice: Subject to any disclaimer, the term of this patent is extended or adjusted under 35 U.S.C. 154(b) by 41 days.

(21) Appl. No.: 13/885,685

(22) PCT Filed: Nov. 16, 2011

(86) PCT No.: PCT/US2011/001915
§ 371 (c)(1),
(2), (4) Date: Aug. 5, 2013

(87) PCT Pub. No.: WO2012/091730
PCT Pub. Date: Jul. 5, 2012

(65) Prior Publication Data
US 2013/0302264 A1 Nov. 14, 2013

Related U.S. Application Data

(60) Provisional application No. 61/414,156, filed on Nov. 16, 2010.

(51) Int. Cl.
| | | |
|---|---|---|
| *A61K 31/475* | (2006.01) | |
| *A61K 31/4375* | (2006.01) | |
| *A61K 45/06* | (2006.01) | |
| *A61K 31/437* | (2006.01) | |
| *A61K 36/72* | (2006.01) | |
| *C07D 471/14* | (2006.01) | |
| *C07D 491/22* | (2006.01) | |
| *A61K 8/49* | (2006.01) | |
| *A61Q 17/04* | (2006.01) | |
| *A61Q 19/04* | (2006.01) | |

(52) U.S. Cl.
CPC .............. *A61K 31/475* (2013.01); *A61K 8/4906* (2013.01); *A61K 8/4926* (2013.01); *A61K 31/437* (2013.01); *A61K 31/4375* (2013.01); *A61K 36/72* (2013.01); *A61K 45/06* (2013.01); *A61Q 17/04* (2013.01); *A61Q 19/04* (2013.01); *C07D 471/14* (2013.01); *C07D 491/22* (2013.01)

(58) Field of Classification Search
None
See application file for complete search history.

(56) References Cited

U.S. PATENT DOCUMENTS

| | | |
|---|---|---|
| 5,508,026 A | 4/1996 | Gerwick et al. |
| 2010/0158833 A1 | 6/2010 | Clemente et al. |

FOREIGN PATENT DOCUMENTS

| | | | |
|---|---|---|---|
| EP | 0680761 | * | 8/1995 |

OTHER PUBLICATIONS

Mayser, et al., Arch Dermatol Res, "Pityriacitrin—an ultraviolet-absorbing indole alkaloid from the yeast *Malassezia furfur*," 2002; 294: 131-134.
Brown, Journal of Photochemistry and Photobiology B: Biology, "Skin pigmentation enhancers," 2001; 63: 148-161.
Malawista, The Journal of Cell Biology, "The Melanocyte Model. Colchicine-like Effects of Other Antimitotic Agents," 1971; 49: 848-855.

* cited by examiner

*Primary Examiner* — Robert A. Wax
*Assistant Examiner* — Danah Al-Awadi
(74) *Attorney, Agent, or Firm* — Klauber & Jackson LLC

(57) ABSTRACT

Provided are indole alkaloid compounds of formula I, for example, pubescine, and the use of such compounds and compositions thereof to promote (e.g., enhance) melanogenesis and pigmentation.

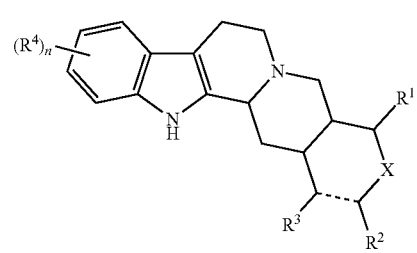

Also provided are plant extracts containing a compound of formula I, for example, pubescine, and the use of such a plant extract to promote (e.g., enhance) melanogenesis and pigmentation. The compound or plant extract may be prepared as pharmaceutical and cosmetic compositions, and may be used for the prevention and treatment of conditions that are related to aberrant melanogenesis activity.

18 Claims, 6 Drawing Sheets

Study 2

Melanin content of Asian skin equivalent (MEL-A) increases ~40% with pubescine treatment.

INDOLE ALKALOID COMPOUNDS AS MELANOGENESIS PROMOTERS AND USES THEREOF

CROSS REFERENCE TO RELATED APPLICATIONS

The present application is a National Stage Application claiming the priority of co-pending PCT Application No. PCT/US2011/001915 filed Nov. 16, 2011, which in turn, claims priority from U.S. Provisional Application Ser. No. 61/414,156, filed Nov. 16, 2010. Applicants claim the benefits of 35 U.S.C. §120 as to the PCT application and priority under 35 U.S.C. §119 as to the said U.S. provisional application, and the entire disclosures of both applications are incorporated herein by reference in their entireties.

GOVERNMENT RIGHTS

This invention was made in part with government support under Grant No. AR41880 awarded by the National Institute of Health. Accordingly, the United States Government has certain rights in the invention.

FIELD OF THE INVENTION

The present invention relates to the identification of compounds that promote melanin synthesis (melanogenesis), and the use of such compounds and compositions thereof to stimulate (enhance) melanin production. This invention also relates to methods for increasing the pigmentation of mammalian skin, hair, wool or fur using the compounds of the invention. This invention further relates to use of the indole alkaloid compounds, for example, as tanning agents, skin or hair darkening agents, and/or as agents to prevent skin damage due to UV irradiation. It is to be understood that such compounds may be used either alone or in combination with other compounds, agents or treatment modalities having the activities set forth herein.

BACKGROUND OF THE INVENTION

Several publications and patent documents are referenced in this application in order to more fully describe the state of the art to which this disclosure pertains. The disclosure of each of these publications and documents is expressly incorporated by reference herein.

Melanin is a dark pigment found in plants and animals that protects against ultraviolet radiation and provides decoration in the skin, eyes, hair, and fur of animals (reviewed in Riley, P. A., 1997, Int. J. Biochem. Cell Biol 11:1235-39). There are two different types of melanin: brown/black eumelanin and yellow/red pheomelanin. Melanocytes are cells of the epidermis specialized to produce melanin. A sophisticated intercellular signaling system determines whether an individual melanocyte will produce melanin or pheomelanin (reviewed in Brilliant, M. H. and Barsh, G. S., 1998, in The System: 217-29, Oxford University, J. J. et al., eds)).

Melanocytes synthesize melanin inside of specialized organelles called melanosomes (reviewed in Orlow, S. J., 1998, in The Pigmentary System: Physiology and 97-106, Oxford University, New York (Nordlund, J. J. eds.)). Melanosomes are formed by the fusion of two types of vesicles. One type of vesicle, called a premelanosome, apparently derives directly from either the smooth endoplasmic reticulum or the trans-Golgi network. The other type of vesicle derives from the network. Each of these types of vesicles contributes proteins to the melanosome necessary for its function.

Defects in the production of melanin result in pigmentation deficiencies such as albinism. Genetic analysis of abnormally pigmented strains of mice has identified more than 60 genes necessary for the normal production of melanin (reviewed in Silvers, W. K., 1979, The Coat Colors of Mice: A Model for Mammalian Gene Action and Interaction, Springer-Verlag, Basel). One of these genes encodes the enzyme tyrosinase. Tyrosinase protein is a multi-functional enzyme that catalyzes several steps in the production of melanin; tyrosinase activities include the rate-limiting steps of converting tyrosine to (DOPA), and DOPA to dopaquinone (reviewed in Lerner, A. B., and Fitzpatrick, T. B., 1950, Physiol. Rev. 30: 91-126), as well as the oxidation of 5,6-dihydroxyindole to 5,6-indolequinone (Korner and Pawelek, 1982, Science 217: 1163-1165). Both humans and mice lacking tyrosinase activity suffer a severe form of albinism.

Two tyrosinase-related proteins (TRP-1, encoded by the mouse brown gene, and TRP-2, encoded by the mouse slaty gene) also are important for melanogenesis (reviewed in Hearing, V. J., 1993, Am. J. Hum. Genet. 52: 1-7). Each of the TRP proteins shares about 40% sequence identity with tyrosinase and with each other. Each of these three enzymes (tyrosinase, TRP-1 and TRP-2) is predicted to contain one transmembrane domain. Together, they form a high molecular weight complex associated with the melanosomal membrane (Orlow, S. J., 1994, 103: 196-201).

Another protein that is important for the production of melanin is the P protein. In mice, it is the product of the pink-eye dilution (p) gene. In humans, it is the product of the P gene. p-null mice produce significantly less melanin than wild-type mice (Silvers, supra). A wild-type human P gene, but not a mutant human P gene, can complement the hypopigmented phenotype of p-null mouse melanocytes (Sviderskaya, E. V., et 1997, J. Invest Dermatol. 108: 30-34). P protein is apparently needed for the production of eumelanin, but not of pheomelanin (Lamoreux, M. L., 1995, Pigment. Cell. Res. 8: 263-70).

Tyrosinase positive oculocutaneous albinism (Ty-pos OCA) or type 2 oculocutaneous albinism (OCA2) is the most common form of albinism worldwide. It results from mutations at the pink-eyed dilution gene (P) (King, R A. (1995) Scriver, C R. (eds) The Metabolic Basis of Inherited Disease, McGraw-Hill, New York. pp 4353-4392; Ramsay, M. et al (1992) Am. J. Hum. Genet. 51:879-84; Rinchik, E. M. et al. (1993) Nature 361: 72-76. Affected individuals have hypopigmented skin, hair and eyes (Manga P. et al. (1999) J. Dermatol. 26: 738-47), and are thus at increased risk of developing UV-induced carcinomas JG. (1989) Clin. Genet. 36 43-52).

Other conditions that can and may be prevented or treated by increased melanin levels in a subject, include conditions where the skin is more sensitive to the deleterious effects of light, such as porphyrias, polymorphous light eruptions, and the like.

Various studies are directed to methods and compositions for increasing melanogenesis. U.S. Pat. No. 5,352,440, for example, is directed to increasing melanin synthesis in melanocytes and increasing pigmentation by administration of certain diacylglycerol compounds. U.S. Pat. No. 5,532,001 is directed to increasing pigmentation in mammalian skin via administration of certain DNA fragments. U.S. Pat. No. 5,554,359 is directed to increasing levels of melanin in melanocytes by administration of lysosomotropic agents. U.S. Pat. Nos. 6,750,229 and 6,995,804 are directed to the identification of protease-activated receptor-2 (PAR-2) pathway and nitric oxide synthesis modulators, respectively, and their use in modulating pigmentation levels.

Additionally, a wide variety of natural products are known to alter the melanin synthesis in melanocytes. A number of alkaloids, in particular indole alkaloids, are known to decrease the melanin synthesis in melanocytes. For example, U.S. Pat. Nos. 6,110,448, 6,096,295, 5,989,576, 5,919,436 and 5,879,665, all by the patentee in U.S. Pat. No. 5,554,359, describe yohimbine, an indole alkaloid, as skin-lightening agent. However, so far none of these indole alkaloids have been reported to be useful in increasing melanin synthesis.

Despite the development of the noted compositions and methods for promoting skin darkening and melanogenesis, there remains a need in the art for the development of less toxic, safer alternatives to the agents and techniques that are presently available. It is accordingly toward the satisfaction of that need that the present invention is directed.

SUMMARY OF THE INVENTION

The present invention is generally directed to compounds and corresponding methods, for increasing melanin content in mammals that need or desire the same, and more particularly, to such compounds and methods, which promote or stimulate melanogenesis. It has been surprisingly discovered that a certain class of indole alkaloids stimulate or promote (rather than inhibit) melanogenesis. Thus, these compounds may be useful for increasing the pigmentation of mammalian skin, hair, wool or fur.

As such, disclosed herein are embodiments directed to the identification of previously unidentified indole akaloid melanogenesis promoters, and their use in increasing pigmentation in in vitro and in vivo applications.

The novel melanogenesis promoters or stimulators include compounds of a certain class of indole alkaloid family.

This invention also relates to methods for increasing the pigmentation of mammalian skin, hair, wool or fur using the compounds of the invention. This invention further relates to use of the indole alkaloid compounds as tanning agents, skin or hair darkening agents, and as agents to prevent skin damage due to UV irradiation.

In one particular aspect, the invention provides a method for enhancing melanogenesis comprising administering to a mammal an effective amount of an indole alkaloid compound.

In one particular embodiment, the indole alkaloid compound is according to formula I:

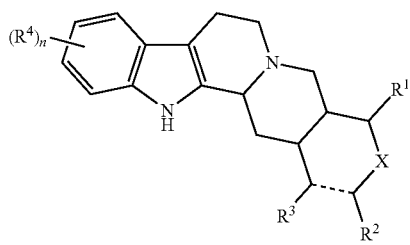

wherein
X is O or CR$^5$;
R$^1$ is selected from the group consisting of hydrogen, hydroxy, substituted or unsubstituted (C$_1$-C$_6$) alkyl, and substituted or unsubstituted (C$_1$-C$_6$) alkoxy;
R$^2$ is selected from the group consisting of hydrogen, hydroxy, substituted or unsubstituted (C$_1$-C$_6$) alkyl, substituted or unsubstituted acyloxy, and substituted or unsubstituted (C$_1$-C$_6$) alkoxy;
R$^3$ is selected from the group consisting of hydrogen, hydroxy, substituted or unsubstituted (C$_1$-C$_6$) alkyl, substituted or unsubstituted acyloxy, substituted or unsubstituted (C$_1$-C$_6$) alkoxy, carboxy, substituted or unsubstituted alkoxycarbonyl, and substituted or unsubstituted amido;
R$^4$ is selected from the group consisting of hydroxy, substituted or unsubstituted (C$_1$-C$_6$) alkyl, substituted or unsubstituted (C$_1$-C$_6$) alkoxy, and halo;
R$^5$ is selected from the group consisting of hydrogen, hydroxy, substituted or unsubstituted (C$_1$-C$_6$) alkyl, substituted or unsubstituted acyloxy, substituted or unsubstituted (C$_1$-C$_6$) alkoxy;
n is 0, 1, 2, 3, or 4; and the dotted bond is a single or a double bond;
or pharmaceutically acceptable salts, solvates, stereo isomers, tautomers, metabolites, analogs, isotopic variants or prodrugs thereof.

In one particular embodiment, with respect to formula I, the compound is pubescine, or pharmaceutically acceptable salts, solvates, stereo isomers, tautomers, metabolites, analogs, isotopic variants or prodrugs thereof.

With respect to in vitro applications, test-tube based and additional cell-based assays may be used to test the ability of modified versions and/or indole alkaloid compounds to promote melanogenesis. In vivo applications are directed to the administration of at least one of the novel melanogenesis stimulator compounds to a subject desirous thereof or in need thereof to increase pigmentation levels for prophylactic, therapeutic and/or cosmetic purposes.

In accordance with the disclosed embodiments, a method is presented for effecting changes in mammalian skin pigmentation comprising topical application of at least one indole alkaloid compound or a composition thereof to the skin of a mammal. Compositions disclosed herein may contain one or more of the indole alkaloid compounds which have been identified as promoters of melanogenesis.

More specifically and with respect to those compounds capable of increasing or enhancing melanogenesis, the disclosed embodiments encompass a method for increasing pigmentation in mammalian skin, hair or wool, which comprises topically administering to the mammal an effective amount of one or more compounds described herein as a melanogenesis promoter.

In a further aspect, the disclosed embodiments provide compositions, including pharmaceutical compositions, cosmetic and personal care formulations, comprising a compound or compounds disclosed herein, and a suitable biocompatible or bioinert carrier, excipient or diluent. In this aspect, the cosmetic, personal care or pharmaceutical composition can comprise one or more of the compounds described herein. Moreover, the compounds disclosed herein are useful in personal care, cosmetic and/or pharmaceutical compositions and treatment methods disclosed herein, are all pharmaceutically and/or cosmetically acceptable as prepared and used.

In a further aspect, the disclosed embodiments provide indole alkaloid compositions useful for darkening the skin or hair.

In a further aspect, the disclosed embodiments provide indole alkaloid compounds or compositions useful as skin tanning agents.

In a further aspect, the disclosed embodiments provide indole alkaloid compounds or compositions useful as self-tanning agents.

In a further aspect, the disclosed embodiments provide methods for darkening the skin or hair using the indole alkaloids of the present invention.

In a further aspect, the disclosed embodiments provide methods for self-tanning using the indole alkaloids of the present invention.

In a further aspect, the disclosed embodiments provide methods for skin tanning using the indole alkaloids of the present invention.

In a further aspect, the disclosed embodiments provide methods for treating loss of skin pigmentation using the indole alkaloids of the present invention.

In a further aspect, the disclosed embodiments provide methods for promoting pigmentation of the skin, the body hair and/or the cranial hair using the indole alkaloids of the present invention.

In a further aspect, the disclosed embodiments provide methods for stimulating melanogenesis of the skin, the body hair and/or the cranial hair, using the indole alkaloids of the present invention.

In a further aspect, the disclosed embodiments provide methods for increasing the pigmentation of mammalian skin, hair, wool or fur using the indole alkaloids of the present invention.

In a further aspect, disclosed herein are compositions comprising a combination of a compound described herein with various additional compounds or agents, including compounds or agents that may have a like effect on melanogenesis, such as, for example, other skin darkening agents. In some embodiments, the additional compound or agent may be a skin care active agent, such as an abrasive, an absorbent, an astringent, an aesthetic component, such as fragrances, pigments, colorings/colorants, essential oils, skin sensates, astringents and other aesthetic components, an antioxidant, a skin tanning or darkening agent, a skin conditioning agent, for example humectants and emollients, a skin soothing agent, a skin healing agent, such as panthenol and derivatives, aloe vera, pantothenic acid, allantoin, bisbolol, dipotassium glycyrrhizinate, skin treating agents, vitamins and derivatives, such as a retinoid, or mixtures thereof. In some embodiments, the retinoid is retinol, retinal, retinol esters, retinyl propionate, retinoic acid, retinyl palmitate, or mixtures thereof. In this aspect, the pharmaceutical and/or cosmetic compositions can comprise one or more of the compounds described herein. Moreover, the compounds are useful in the pharmaceutical and/or cosmetic compositions and treatment methods disclosed herein, are all pharmaceutically and/or cosmetically acceptable as prepared and used.

Also provided are methods for promoting melanogenesis by melanocytes, comprising administering to the melanocytes or to skin tissue an effective amount of a plant extract containing a melanogenesis promoter. In some embodiments, the melanogenesis promoter is indole alkaloid melanogenesis promoter as in Formula I. In some embodiments, the melanogenesis promoter is pubescine or a pubescine derivative. In some embodiments, the melanocytes are mammalian melanocytes. In some embodiments, the skin tissue is human skin including but not limited to African American, Asian and Caucasian skin equivalents. In some embodiments, the plant extract is derived from a plant of the *Discaria pubescens* family. Other examples include plant extract derived from *Rauwolfia Nitida* as described in U.S. Pat. No. 3,072,664, which is hereby incorporated by reference in its entirety.

In some embodiments, also provided are plant extracts containing a prophylactically, therapeutically and/or cosmetically effective amount of a melanogenesis promoter for use as a promoter of melanogenesis. The plant extract can be used as a pharmaceutical, a medicament or as a cosmetic agent. In some embodiments, the plant extract is substantially purified or partially purified for concentration of the melanogenesis promoter. In other embodiments, the plant extract may be substantially liquefied or partially liquefied for administration to a patient in need thereof. The plant extract may also be processed to remove particulate matter prior to administration. In some embodiments, the melanogenesis promoter is pubescine or a pubescine derivative.

Also provided are uses of a plant extract as disclosed herein for the manufacture of a medicament or cosmetic agent to treat a disease, condition or effect for which a melanogenesis promoter is indicated. The diseases, condition or effect that can be prevented, treated, ameliorated and/or managed by the subject compositions and methods include but are not limited to uneven pigmentation disorders such as white spots. In other embodiments, a topical formulation comprising a composition is provided for cosmetic and/or dermatological/pharmaceutical use, said composition comprising a plant extract containing a prophylactically, cosmetically or therapeutically effective amount of pubescine.

In some embodiments, the plant extract is derived from a plant of the *Discaria pubescens* family. In some embodiments, the plant extract is derived from *Rauwolfia Nitida*. In some embodiments, the plant extract is substantially purified or partially purified for concentration of the melanogenesis promoter. In other embodiments, the plant extract may be substantially liquefied or partially liquefied for administration to a patient in need thereof. The plant extract may also be processed to remove particulate matter prior to administration. In some embodiments, the melanogenesis promoter is pubescine or a pubescine derivative.

In some embodiments, the plant extract is derived from any plant which can be used as a source for pubescen and related alkaloids. In one embodiment, the plant extract is derived from *Hollarrhena antidysenterica* (H. Pubescens).

Also provided are methods for preventing, treating, ameliorating or managing a disease or condition involving aberrant melanogenesis, which comprises administering to a patient in need or desirous of such prevention, treatment, amelioration or management, a prophylactically or therapeutically effective melanogenesis-promoting amount of a plant extract containing a melanogenesis promoter. In some embodiments, the melanogenesis promoter is an indole alkaloid melanogenesis promoter as in Formula I. In one embodiment, the melanogenesis promoter is pubescine or a pubescine derivative.

In yet another aspect, methods are provided for altering or restoring pigmentation in mammalian skin, hair, wool or fur comprising administering to the mammalian skin, hair, wool or fur an amount, which is effective to alter or restore pigmentation in mammalian skin, hair, wool or fur, of a plant extract containing pubescine.

In still another aspect, also provided are methods of treatment of a mammal, including a human being, to treat a disease for which a melanogenesis promoter is indicated, including treating said mammal with an effective amount of a plant extract containing pubescine. In some embodiments, the plant extract is derived from a plant of the *Discaria pubescens* family. In some embodiments, the plant extract is derived from *Rauwolfia Nitida*. In some embodiments, the plant extract is substantially purified or partially purified for concentration of the melanogenesis promoter. In other embodiments, the plant extract may be substantially liquefied or partially liquefied for administration to a patient in need thereof. The plant extract may also be processed to remove particulate matter prior to administration. In some embodiments, the melanogenesis promoter is pubescine or a pubescine derivative.

In some embodiments of the subject methods, the melanogenesis-promoter containing plant extract is administered to darken or increase pigmentation levels. For example, the melanogenesis-promoter-containing plant extract is administered to darken or increase pigmentation levels of hypopigmented sites on skin. In some embodiments, the melanogenesis promoter is pubescine or a pubescine-derivative. In some embodiments, the plant extract is derived from a plant of the *Discaria pubescens* family. In some embodiments, the plant extract is derived from *Rauwolfia Nitida*. In some embodiments, the plant extract is substantially purified or partially purified for concentration of the melanogenesis promoter. In other embodiments, the plant extract may be substantially liquefied or partially liquefied for administration to a patient in need thereof. The plant extract may also be processed to remove particulate matter prior to administration. In some embodiments, the melanogenesis promoter is pubescine or a pubescine derivative. In some embodiments, the melanogenesis promoter is pubescine or a pubescine derivative.

In a further embodiment, combinations of a plant extract as disclosed herein and a like-acting agent are provided. The like acting agent can be selected from a cosmetic ingredient and/or a pharmacologically active agent. For example, the cosmetic ingredient may be a skin tanning agent. The pharmacologically active agent can be selected from another melanogenesis promoter, or even a tanning modality such as a source of ultra-violet light.

Another aspect encompasses a method for enhancing melanogenesis by melanocytes comprising administering to the melanocytes an effective amount of a plant extract containing a melanogenesis-promoter in combination with a like-acting agent. In some embodiments, the plant extract is substantially purified or partially purified for concentration of the melanogenesis promoter. In other embodiments, the plant extract may be substantially liquefied or partially liquefied for administration to a patient in need thereof. The plant extract may also be processed to remove particulate matter prior to administration. In some embodiments, the melanogenesis promoter is pubescine or a pubescine derivative. In some embodiments, the melanogenesis promoter is pubescine or a pubescine derivative.

Also provided herein is a method for preventing, treating, ameliorating or managing a disease or condition involving aberrant melanogenesis, which comprises administering to a patient in need or desirous of such prevention, treatment, amelioration or management, a prophylactically or therapeutically effective melanogenesis-enhancing amount of a plant extract in combination with a like-acting agent. In another aspect, provided are methods for altering or restoring pigmentation in mammalian skin, hair, wool or fur comprising administering to the mammalian skin, hair, wool or fur an amount, which is effective to alter or restore pigmentation in mammalian skin, hair, wool or fur, of a plant extract containing a melanogenesis-promoter in combination with a like-acting agent.

In still another aspect, also provided are methods of treatment of a mammal, including a human being, to treat a condition for which a melanogenesis promoter is indicated, including treating said mammal with an effective amount of a plant extract containing a melanogenesis-inhibitor in combination with a like-acting agent. In some embodiments, the plant extract is derived from a plant of the *Discaria pubescens* family. In some embodiments, the plant extract is derived from *Rauwolfia Nitida*.

In any of the above subject methods, the like acting agent can be selected from a cosmetic ingredient and a pharmacologically active agent. One example of a cosmetic ingredient is a skin darkener. The pharmacologically active agent can be selected from another melanogenesis promoter.

Also provided are uses of the indole alkaloids of the invention as agents to prevent skin damage due to visible light or ultraviolet irradiation. In a particular embodiment, the indole alkaloid agent is pubescine or a pubescine derivative.

Other objects and advantages will become apparent to those skilled in the art from a consideration of the ensuing detailed description, which proceeds with reference to the following illustrative drawings.

DETAILED DESCRIPTION OF THE INVENTION

Definitions

Figure 1:
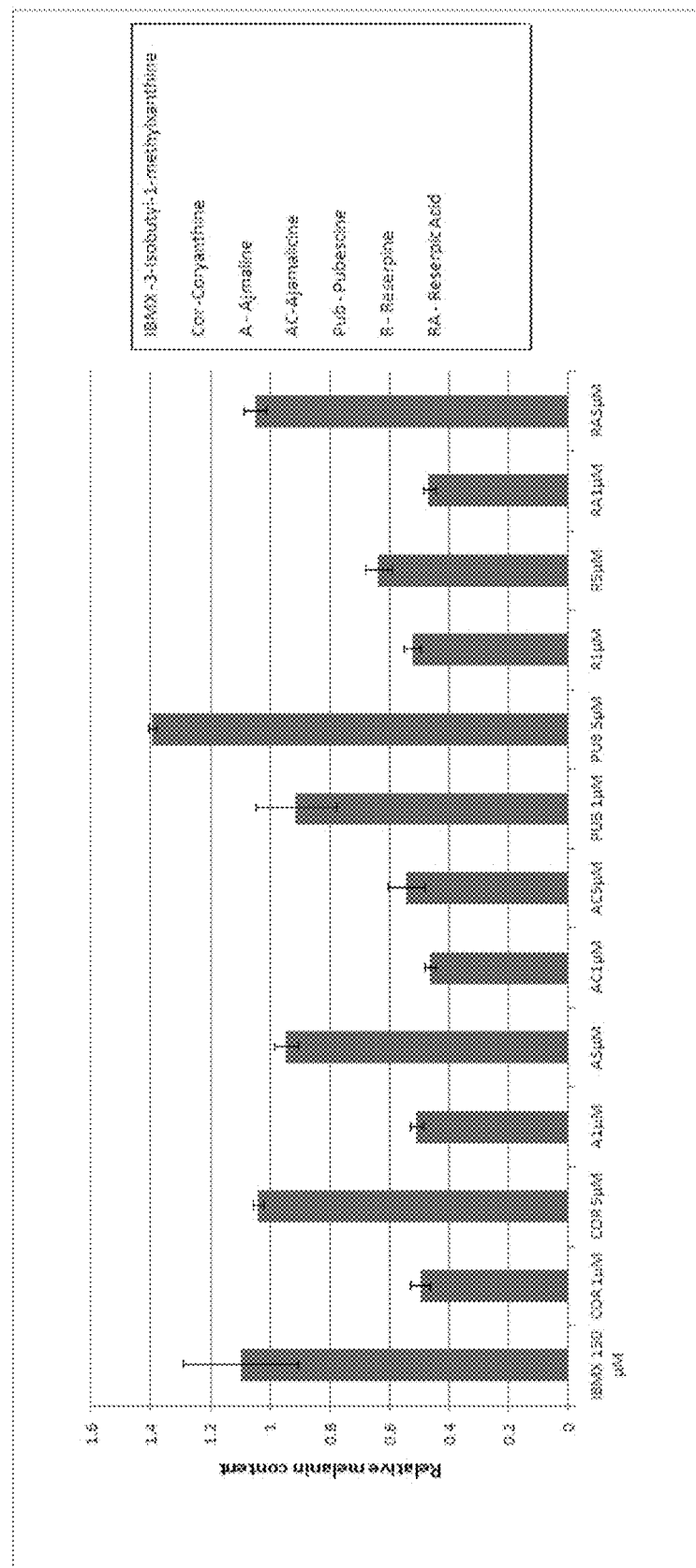
FIG. 1 is a bar graph presenting the melanine assay results for the representative indole alkaloids at 1 uM and 5 uM concentrations.

When describing the compounds, pharmaceutical and/or cosmetic compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Acyl" refers to a group or radical —C(O)R$^{20}$, where R$^{20}$ is hydrogen, substituted or unsubstituted alkyl, substituted or unsubstituted cycloalkyl, substituted or unsubstituted cycloheteroalkyl, substituted or unsubstituted aryl, substituted or unsubstituted arylalkyl, substituted or unsubstituted heteroalkyl, substituted or unsubstituted heteroaryl, substituted or unsubstituted heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylathino" refers to a group or radical —NR$^{21}$C(O)R$^{22}$, where R$^{21}$ is hydrogen, substituted or unsubstituted alkyl, substituted or unsubstituted cycloalkyl, substituted or unsubstituted cycloheteroalkyl, substituted or unsubstituted aryl, substituted or unsubstituted arylalkyl, substituted or unsubstituted heteroalkyl, substituted or unsubstituted heteroaryl, substituted or unsubstituted heteroarylalkyl and R$^{22}$ is hydrogen, substituted or unsubstituted alkyl, substituted or unsubstituted alkoxy, substituted or unsubstituted cycloalkyl, substituted or unsubstituted cycloheteroalkyl, substituted or unsubstituted aryl, substituted or unsubstituted arylalkyl, substituted or unsubstituted heteroalkyl, substituted or unsubstituted heteroaryl or substituted or unsubstituted heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group or radical —OC(O)$R^{23}$ where $R^{23}$ is hydrogen, substituted or unsubstituted alkyl, substituted or unsubstituted aryl or substituted or unsubstituted cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —O$R^{24}$ where $R^{24}$ is alkyl. Particular alkoxy groups include, by way of example, substituted or unsubstituted methoxy, substituted or unsubstituted ethoxy, substituted or unsubstituted n-propoxy, substituted or unsubstituted isopropoxy, substituted or unsubstituted n-butoxy, substituted or unsubstituted tert-butoxy, substituted or unsubstituted sec-butoxy, substituted or unsubstituted n-pentoxy, substituted or unsubstituted n-hexoxy, substituted or unsubstituted 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —N$R^{25}$C(O)$R^{26}$ where $R^{25}$ is hydrogen, substituted or unsubstituted alkyl, substituted or unsubstituted aryl or substituted or unsubstituted cycloalkyl, and $R^{26}$ is substituted or unsubstituted alkyl or substituted or unsubstituted cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, iso-propyl, n-butyl, iso-butyl, tert-butyl, n-hexyl, n-octyl, tert-octyl and the like, and may be substituted or unsubstituted. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as substituted or unsubstituted methylene (—CH$_2$—), substituted or unsubstituted ethylene (—CH$_2$CH$_2$—), the substituted or unsubstituted propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonyl amino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include substituted or unsubstituted ethenyl (—CH=CH$_2$), substituted or unsubstituted n-propenyl (—CH$_2$CH=CH$_2$), substituted or unsubstituted isopropenyl (—C(CH$_3$)=CH$_2$), substituted or unsubstituted vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as substituted or unsubstituted ethenylene (—CH=CH—), substituted or unsubstituted propenylene isomers (e.g., —CH=CHCH$_2$— and —C(CH$_3$)=CH— and —CH=C(CH$_3$)—) and the like.

"Alkynyl" refers to acetylenically or alkynically unsaturated hydrocarbyl groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include substituted or unsubstituted acetylenic, substituted or unsubstituted ethynyl (—C≡CH), substituted or unsubstituted propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group $R^{27}$—C(O)—, where $R^{27}$ is hydrogen or substituted or unsubstituted alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like, and may be substituted or unsubstituted. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second substituted or unsubstituted aryl ring or with a substituted or unsubstituted aliphatic ring.

"Alkaryl" refers to an aryl group, as defined above, substituted with one or more substituted or unsubstituted alkyl groups, as defined above.

"Aralkyl" or "arylalkyl" refers to an alkyl group, as defined above, substituted with one or more substituted or unsubstituted aryl groups, as defined above.

"Aryloxy" refers to substituted or unsubstituted —O-aryl groups wherein "aryl" is as defined above.

"Alkylamino" refers to the group alkyl-$NR^{28}R^{29}$, wherein each of $R^{28}$ and $R^{29}$ are independently selected from hydrogen and substituted or unsubstituted alkyl.

"Arylamino" refers to the group aryl-$NR^{30}R^{31}$, wherein each of $R^{30}$ and $R^{31}$ are independently selected from hydrogen, substituted or unsubstituted aryl and substituted or unsubstituted heteroaryl.

"Alkoxyamino" refers to a radical —N(H)O$R^{32}$ where $R^{32}$ represents a substituted or unsubstituted alkyl or substituted or unsubstituted cycloalkyl group as defined herein.

"Alkoxycarbonyl" refers to a substituted or unsubstituted radical —C(O)-alkoxy where alkoxy is as defined herein.

"Alkylarylamino" refers to a substituted or unsubstituted radical —$NR^{33}R^{34}$ where $R^{33}$ represents an alkyl or cycloalkyl group and $R^{34}$ is an aryl as defined herein.

"Alkylsulfonyl" refers to a substituted or unsubstituted radical —S(O)$_2R^{35}$ where $R^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a substituted or unsubstituted radical —S(O)$R^{35}$ where $R^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a substituted or unsubstituted radical —S$R^{35}$ where $R^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N($R^{36}$)$_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N($R^{36}$)$_2$ is an amino group.

"Aminocarbonyl" refers to the group —C(O)N$R^{37}R^{37}$ where each $R^{37}$ is independently hydrogen, substituted or unsubstituted alkyl, substituted or unsubstituted aryl and substituted or unsubstituted cycloalkyl, or where the $R^{37}$ groups are joined to form an alkylene group.

"Aminocarbonylamino" refers to the group —$NR^{38}$C(O)N$R^{38}R^{38}$ where each $R^{38}$ is independently hydrogen, substituted or unsubstituted alkyl, substituted or unsubstituted aryl or substituted or unsubstituted cycloalkyl, or where two R groups are joined to form an alkylene group.

"Aminocarbonyloxy" refers to the group —OC(O)N$R^{39}R^{39}$ where each $R^{39}$ is independently hydrogen, substituted or unsubstituted alkyl, substituted or unsubstituted aryl or substituted or unsubstituted cycloalkyl, or where the R groups are joined to form an alkylene group.

"Arylalkyloxy" refers to a substituted or unsubstituted —O-arylalkyl radical where arylalkyl is as defined herein.

"Arylamino" means a substituted or unsubstituted radical —NH$R^{40}$ where $R^{40}$ represents an aryl group as defined herein.

"Aryloxycarbonyl" refers to a substituted or unsubstituted radical —C(O)—O-aryl where aryl is as defined herein.

"Arylsulfonyl" refers to a r substituted or unsubstituted radical —S(O)$_2R^{41}$ where $R^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like, and may be substituted or unsubstituted. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like, and may be substituted or unsubstituted. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N($R^{42}$)$_2$ where each $R^{42}$ group is independently hydrogen, substituted or unsubstituted alkyl, substituted or unsubstituted cycloalkyl or substituted or unsubstituted aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like, and may be substituted or unsubstituted.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —O$R^{43}$ where $R^{43}$ is substituted or unsubstituted cycloalkyl. Such cycloalkoxy groups include, by way of example, substituted or unsubstituted cyclopentoxy, substituted or unsubstituted cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as substituted or unsubstituted cyclohexenyl, substituted or unsubstituted cyclopentenyl, substituted or unsubstituted cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a substituted or unsubstituted cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —N$R^{44}R^{45}$ where $R^{44}$ and $R^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —$R^{46}$, —O$^-$, =O, —O$R^{46}$, —S$R^{46}$, —S$^-$, =S, —N$R^{46}R^{47}$, =N$R^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$$R^{46}$, —OS(O$_2$)O$^-$, —OS(O)$_2$$R^{46}$, —P(O)(O$^-$)$_2$, —P(O)(O$R^{46}$)(O$^-$), —OP(O)(O$R^{46}$)(O$R^{47}$), —C(O)$R^{46}$, —C(S)$R^{46}$, K C(O)O$R^{46}$, C(O)N$R^{46}R^{47}$, —C(O)O$^-$, —C(S)O$R^{46}$, —N$R^{48}$C(O)N$R^{46}R^{47}$, —N$R^{48}$C(S)N$R^{46}R^{47}$, —N$R^{49}$C(N$R^{48}$)N$R^{46}R^{47}$ and —C(N$R^{48}$)N$R^{46}R^{47}$, where each X is independently a halogen; each $R^{46}$, $R^{47}$, $R^{48}$ and $R^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —N$R^{50}R^{51}$, —C(O)$R^{50}$ or —S(O)$_2$$R^{50}$ or optionally $R^{50}$ and $R^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

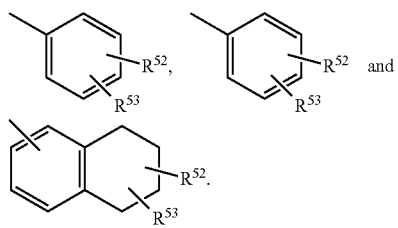

In these formulae one of $R^{52}$ and $R^{53}$ may be hydrogen and at least one of $R^{52}$ and $R^{53}$ is each independently selected from alkyl, alkenyl, alkynyl, cycloheteroalkyl, alkanoyl, alkoxy, aryloxy, heteroaryloxy, alkylamino, arylamino, heteroarylamino, N$R^{54}$CO$R^{55}$, N$R^{54}$SO$R^{55}$, N$R^{54}$SO$_2$$R^{57}$, COOalkyl, COOaryl, CON$R^{54}R^{55}$, CON$R^{54}$O$R^{55}$, N$R^{54}R^{55}$, SO$_2$N$R^{54}R^{55}$, S-alkyl, S-alkyl, SOalkyl, SO$_2$alkyl, Saryl, SOaryl, SO$_2$aryl; or $R^{52}$ and $R^{53}$ may be joined to form a cyclic ring (saturated or unsaturated) from 5 to 8 atoms, optionally containing one or more heteroatoms selected from the group N, O or S. $R^{54}$, $R^{55}$, and $R^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

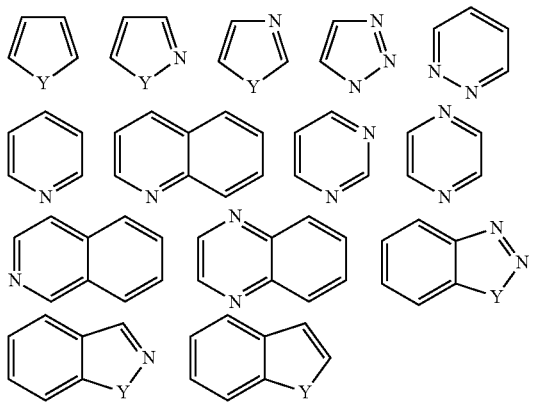

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

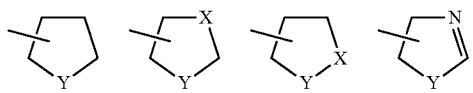

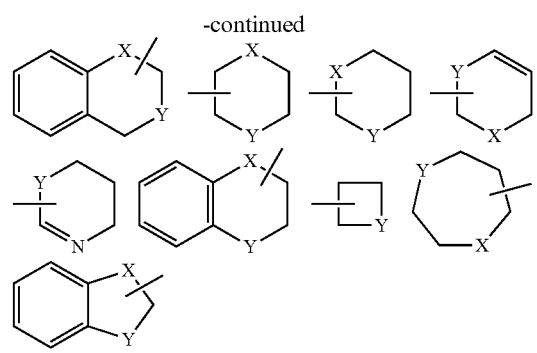

wherein each X is selected from $CR^{58}$, $CR^{58}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

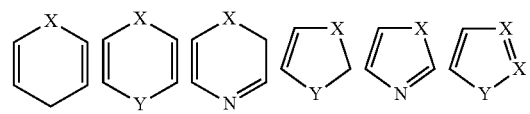

wherein each X is selected from $CR^{58}$, $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

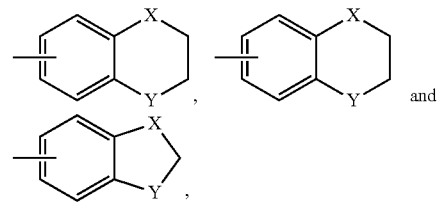

wherein each X is selected from $CR^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an $R^4$ in a $R^4C$ group present as substituents directly on the ring or rings of the compounds disclosed herein, or that may be present as a substituent in any "substituted" aryl and aliphatic groups present in the compounds.

Examples of hetero substituents include:
-halo,
—$NO_2$, —$NH_2$, —$NHR^{59}$, —$N(R^{59})_2$,
—$NRCOR$, —$NR^{59}SOR^{59}$, —$NR^{59}SO_2R^{59}$, OH, CN,
—$CO_2H$,
—$R^{59}$—OH, —O—$R^{59}$, —$COOR^{59}$,
—$CON(R^{59})_2$, —$CONROR^{59}$,
—$SO_3H$, —$R^{59}$—S, —$SO_2N(R^{59})_2$,
—$S(O)R^{59}$, —$S(O)_2R^{59}$ wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Dihydroxyphosphoryl" refers to the substituted or unsubstituted radical —$PO(OH)_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the substituted or unsubstituted radical —$PO(OH)NH_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the substituted or unsubstituted group —$SR^{60}$ where $R^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Sulfanyl" refers to the substituted or unsubstituted radical HS—. "Substituted sulfanyl" refers to a radical such as RS— wherein R is any substituent described herein.

"Sulfonyl" refers to the divalent substituted or unsubstituted radical —$S(O_2)$—. "Substituted sulfonyl" refers to a radical such as $R^{61}$—$(O_2)S$— wherein $R^{61}$ is any substituent described herein. "Aminosulfonyl" or "Sulfonamide" refers to the radical $H_2N(O_2)S$—, and "substituted aminosulfonyl" "substituted sulfonamide" refers to a radical such as $R^{62}_2N(O_2)S$— wherein each $R^{62}$ is independently any substituent described herein.

"Sulfone" refers to the substituted or unsubstituted group —$SO_2R^{63}$. In particular embodiments, $R^{63}$ is selected from H, lower alkyl, alkyl, aryl and heteroaryl.

"Thioaryloxy" refers to the substituted or unsubstituted group —$SR^{64}$ where $R^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

As used herein, "mammal" refers to any member of the higher vertebrate animals comprising the class Mammalia, which includes, but is not limited to, humans.

As used herein, the term "melanogenesis promoter" is used to describe a compound identified herein as possessing the ability to enhance melanogenesis in a melanocyte.

As used herein, an "amount effective" shall mean an amount sufficient to cover the region of skin, hair, fur, or wool surface where a change in pigmentation is desired.

"Pharmaceutically acceptable" means approved by a regulatory agency of the Federal or a state government or listed in the U.S. Pharmacopoeia or other generally recognized pharmacopoeia for use in animals, and more particularly in humans.

"Cosmeceutically acceptable" means suitable for cosmetic applications, including topical application of the compositions disclosed herein in the absence of significant adverse side effects upon application of the composition or compounds disclosed herein. Other applications include skin care applications, including but not limited to lotions, cream, cleansing creams or lotions, soaps and other cleansers, antiperspirant and/or deodorants, makeup products, such as face powders, foundations, rouge, eye shadow, mascara, eyeliner or lipstick, sun protection products, such as sunscreen or other UV-protective cosmetics, lotions or creams, hairdressing products, such as shampoo, rinses, or treatment setting agents. The phrases "pharmaceutically acceptable" and "cosmeceutically acceptable" are not meant to imply mutual exclusiveness in all applications. In some embodiments, a composition may be both "pharmaceutically acceptable" and "cosmeceutically acceptable," dependent upon the need and course of action of the compositions disclosed herein.

"Pharmaceutically acceptable salt" refers to a salt of a compound disclosed herein that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. In some embodiments, a "pharmaceutically acceptable salt" may also be used in conjunction with cosmeceutically-acceptable compositions.

The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like. In some embodiments, a "pharmaceutically acceptable cation" may also be used in conjunction with cosmeceutically-acceptable compositions.

"Pharmaceutically acceptable vehicle" refers to a diluent, adjuvant, excipient or carrier with which a disclosed compound is administered. In some embodiments, a "pharmaceutically acceptable vehicle" may also be used in conjunction with cosmeceutically-acceptable compositions.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of disclosed compounds, which have cleavable groups and become by solvolysis or under physiological conditions of compounds which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds disclosed herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same. In a still further embodiment, "treating" or "treatment" refers to administration of the compound or compositions disclosed herein for cosmetic purposes.

Other derivatives of the disclosed compounds have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the disclosed compounds are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the disclosed compounds herein.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H/D$, any carbon may be $^{13}C$, or any nitrogen may be $^{15}N$, and that the presence and placement of such atoms may be determined within the skill of the art. Likewise, the disclosed compounds may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the contemplated compounds.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The disclosed compounds may possess one or more asymmetric centers; such compounds can therefore be produced as individual (R)— or (S)— stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

THE COMPOUNDS

The present invention is directed to compounds that enhance or stimulate melanogenesis.

As such, disclosed herein are embodiments directed to the identification of previously unidentified indole akaloid melanogenesis promoters, and their use in controlling (e.g. increasing) pigmentation in in vitro and in vivo applications.

The novel melanogenesis promoters or stimulators include compounds of a certain class of indole alkaloid family.

This invention also relates to methods for increasing the pigmentation of mammalian skin, hair, wool or fur using the compounds of the invention. This invention further relates to use of the indole alkaloid compounds as tanning agents, skin or hair darkening agents, and as agents to prevent skin damage due to UV irradiation.

In one particular aspect, the invention provides a method for enhancing melanogenesis comprising administering to a mammal an effective amount of an indole alkaloid compound.

In one particular aspect, the invention provides a method for enhancing melanogenesis comprising administering to a mammal an effective amount of an indole alkaloid compound.

In one particular embodiment, the indole alkaloid compound is according to formula I:

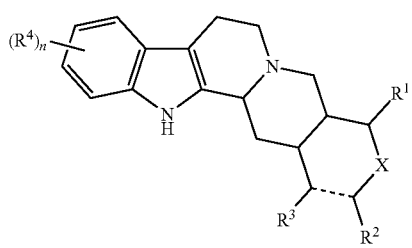

I wherein
X is O or $CR^5$;
$R^1$ is selected from the group consisting of hydrogen, hydroxy, substituted or unsubstituted ($C_1$-$C_6$) alkyl, and substituted or unsubstituted ($C_1$-$C_6$) alkoxy;
$R^2$ is selected from the group consisting of hydrogen, hydroxy, substituted or unsubstituted ($C_1$-$C_6$) alkyl, substituted or unsubstituted acyloxy, and substituted or unsubstituted ($C_1$-$C_6$) alkoxy;
$R^3$ is selected from the group consisting of hydrogen, hydroxy, substituted or unsubstituted ($C_1$-$C_6$) alkyl, substituted or unsubstituted acyloxy, substituted or unsubstituted ($C_1$-$C_6$) alkoxy, carboxy, substituted or unsubstituted alkoxycarbonyl, and substituted or unsubstituted amido;
$R^4$ is selected from the group consisting of hydroxy, substituted or unsubstituted ($C_1$-$C_6$) alkyl, substituted or unsubstituted ($C_1$-$C_6$) alkoxy, and halo;
$R^5$ is selected from the group consisting of hydrogen, hydroxy, substituted or unsubstituted ($C_1$-$C_6$) alkyl, substituted or unsubstituted acyloxy, substituted or unsubstituted ($C_1$-$C_6$) alkoxy;
n is 0, 1, 2, 3, or 4; and the dotted bond is a single or a double bond;

or pharmaceutically acceptable salts, solvates, stereo isomers, tautomers, metabolites, analogs, isotopic variants or prodrugs thereof.

In one embodiment, with respect to the indole alkaloid compound according to formula I, X is $CR^5$; and the dotted bond is a single bond. In another embodiment, X is $CR^5$; and the dotted bond is a double bond.

In one embodiment, with respect to the indole alkaloid compound according to formula I, the compound is according to formula II:

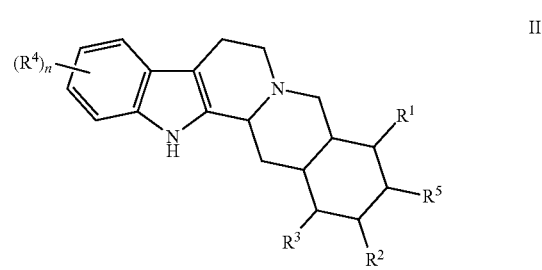

II wherein $R^1$-$R^5$, and n are as described for formula I; or a pharmaceutically acceptable salt, solvate, stereo isomer, tautomer, metabolite, analog, isotopic variant or prodrug thereof.

In one embodiment, with respect to the indole alkaloid compound according to formulae I-II, $R^5$ is H, OH, substituted or unsubstituted ($C_1$-$C_6$) alkoxy, or $OCOR^6$; and $R^6$ is OH, substituted or unsubstituted ($C_1$-$C_6$) alkyl, substituted or unsubstituted aryl, or substituted or unsubstituted heteroaryl. In another embodiment, $R^5$ is H, OH, OMe, OCOPh, OC(O)-(3,4,5-trimethoxyphen-1-yl), OCOMe, or $OCOCH_2COMe$. In one particular embodiment, $R^5$ is OCOPh. In a more particular embodiment, $R^5$ is OC(O)-(3,4,5-trimethoxyphen-1-yl).

In one embodiment, with respect to the indole alkaloid compound according to formula I, X is O; and the dotted bond is a double bond. In another embodiment, the dotted bond is a single bond.

In one embodiment, with respect to the indole alkaloid compound according to formula I, the compound is according to formula III:

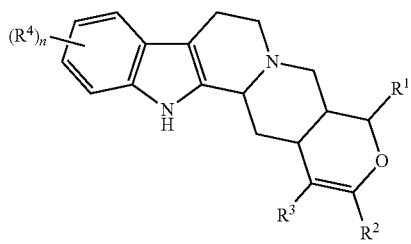

III wherein R¹-R⁴, and n are as described for formula I; or a pharmaceutically acceptable salt, solvate, stereo isomer, tautomer, metabolite, analog, isotopic variant or prodrug thereof.

In one embodiment, with respect to the indole alkaloid compound according to formulae I-III, R¹ is H, OH, substituted or unsubstituted ($C_1$-$C_6$) alkoxy or substituted or unsubstituted ($C_1$-$C_6$) alkyl. In another embodiment, R¹ is H, OH, OMe, Me, or Et. In a particular embodiment, R¹ is H, or Me. In a more particular embodiment R¹ is a-Me In one embodiment, with respect to the indole alkaloid compound according to formulae I-III, R² is H, OH, substituted or unsubstituted acyloxy, and substituted or unsubstituted ($C_1$-$C_6$) alkoxy. In another embodiment, R² is H, OH, OMe, or OCOMe. In a particular embodiment, R² is H, or OMe. In a more particular embodiment R² is H.

In one embodiment, with respect to the indole alkaloid compound according to formulae I-III, R³ is H, carboxy, substituted or unsubstituted alkoxycarbonyl, or substituted or unsubstituted amido. In another embodiment, R³ is $CO_2H$, $CO_2Me$, $CO_2Et$, $C(O)OCH_2CH_2NH_2$, $C(O)OCH_2CH_2NMe_2$, $CONH_2$, $CONHMe$, $CONHPh$, $CONMe_2$, or $C(O)NHCH_2CH_2NH_2$. In a particular embodiment, R³ is $CO_2H$, or $CO_2Me$. In a more particular embodiment R³ is $CO_2Me$.

In one embodiment, with respect to the indole alkaloid compound according to formulae I-III, n is 0.

In one embodiment, with respect to the indole alkaloid compound according to formulae I-III, n is 1; and R⁴ is halo.

In one embodiment, with respect to the indole alkaloid compound according to formulae I-III, n is 1; and R⁴ is F or Cl.

In one embodiment, with respect to the indole alkaloid compound according to formulae I-III, n is 1; and R⁴ is Me.

In one embodiment, with respect to the indole alkaloid compound according to formulae I-III, n is 1 or 2; and each R⁴ is independently substituted or unsubstituted ($C_1$-$C_6$) alkoxy.

In one embodiment, with respect to the indole alkaloid compound according to formulae I-III, n is 1 or 2; and each R⁴ is independently OMe or OEt. In one particular embodiment, n is 1 and R⁴ is 3-OMe. In another particular embodiment, R⁴ is 4-OMe. In a further embodiment, n is 2 and one R⁴ is 3-OMe and the other is 4-OMe.

In one particular embodiment, with respect to the indole alkaloid compound according to formula I, the compound is according to formula IV:

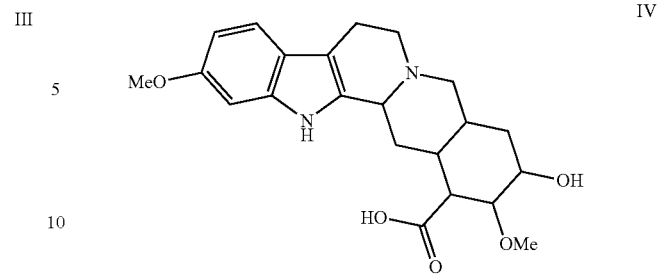

IV or a pharmaceutically acceptable salt, solvate, stereo isomer, tautomer, metabolite, analog, isotopic variant or prodrug thereof.

In another particular embodiment, with respect to the indole alkaloid compound according to formula I, the compound is according to formula V:

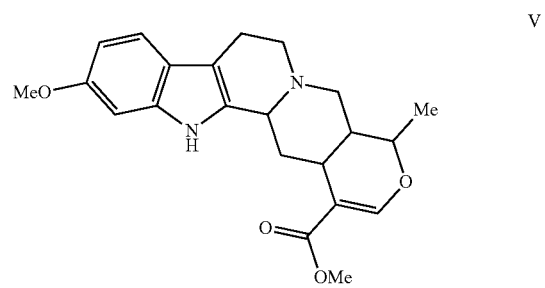 [SMILES: COC(=O)C1=COC(C)C2CN3CCc4c([nH]c5cc(OC)ccc45)C3CC12]

V or a pharmaceutically acceptable salt, solvate, stereo isomer, tautomer, metabolite, analog, isotopic variant or prodrug thereof.

In another particular embodiment, with respect to the indole alkaloid compound according to formula I, the compound is reserpic acid or reserpic acid analog.

In another particular embodiment, with respect to the indole alkaloid compound according to formula I, the compound is reserpic acid.

In another particular embodiment, with respect to the indole alkaloid compound according to formula I, the compound is pubescine or pubescine analog.

In a most particular embodiment, with respect to the indole alkaloid compound according to formula I, the compound is pubescine.

In one particular embodiment, with respect to formulae I-V, the compound is a free base.

In one particular embodiment, with respect to formulae I-V, the compound is a mono HCl salt.

In one particular embodiment, with respect to formulae I-V, the compound is a di HCl salt.

In one particular embodiment, with respect to formulae I-V, the compound is a hydrated salt.

In one particular embodiment, with respect to formulae I-V, the compound is selected from the group consisting of the compounds set forth in Table 1; or a pharmaceutically acceptable salt, solvate, stereo isomer, tautomer, metabolite, analog, isotopic variant or prodrug thereof.

In one particular embodiment, with respect to formulae I-V, the compound is selected from the group consisting of the compounds set forth in Table 2; or a pharmaceutically acceptable salt, solvate, stereo isomer, tautomer, metabolite, analog, isotopic variant or prodrug thereof.

In one embodiment, with respect to the method of invention, the method further comprises an additional active agent. In one embodiment, the additional active agent is a pharmacological agent, a skin darkening agent or a skin tanning agent.

In a further embodiment, with respect to the additional active agent described above, the additional active agent is a tanning agent.

In one embodiment, with respect to the additional active agent described above, the additional active agent is an agent that increases skin melanin content.

In one embodiment, with respect to the additional active agent described above, the additional active agent is an agent that darkens the skin. In one embodiment, the agent is a tanning agent. In another embodiment, the tanning agent is a Dihydroxyaxcetone-based tanner.

In one embodiment, with respect to the additional active agent described above, the additional active agent is a phosphodiesterase inhibitor.

In one embodiment, with respect to the additional active agent described above, the phosphodiesterase inhibitor is a xanthine derivative. In another embodiment, the phosphodiesterase inhibitor is methylxanthine. In yet another embodiment, the phosphodiesterase inhibitor is cipamfylline.

In one embodiment, with respect to the additional active agent described above, the additional active agent is selected from psoralens. In another embodiment, the additional active agent is selected from furocoumarins.

In one embodiment, with respect to the additional active agent described above, the additional active agent is a self tanning agent.

In one embodiment, with respect to the additional active agent described above, the additional active agent is dihydroxyacetone.

In one embodiment, with respect to the additional active agent described above, the additional active agent is ultraviolate light.

In one embodiment, with respect to the additional active agent described above, the additional active agent is an agent that increases skin melanin content.

In one embodiment, with respect to the additional active agent described above, the additional active agent is an agent that darkens the skin.

In one embodiment, with respect to the additional active agent described above, the additional active agent is dihydroxyacetone based tanner.

In one embodiment, with respect to the additional active agent described above, the additional active agent is melanocyte stimulating hormone or an analogue or fragment thereof.

A further aspect extends to a formulation that comprises a combination of a compound with respect to formulae I-V, and an additional pharmaceutical or cosmetic agent. In one embodiment, the additional pharmaceutical or cosmetic agent is a like-acting agent. In a particular embodiment, the like acting agent is selected from a cosmetic ingredient and a pharmacologically active agent.

In one embodiment of the combination just described, a pharmaceutical composition is prepared that is useful to treat a disease for which a melanogenesis promoter is indicated, which comprises a therapeutically effective amount of the combination, wherein the like acting agent is a pharmacologically active agent. More particularly, the like-acting agent is a skin darkening or skin tanning compound.

In a further embodiment of the combination described above, a topical formulation is prepared that comprises a composition for cosmetic or dermatological use, which composition comprises a cosmetically and/or dermatologically effective amount of the combination stated above, wherein the like acting agent is a cosmetically active agent. More particularly, the like-acting agent is a skin darkening or skin tanning compound.

In a further embodiment of the combinations described above, the like acting agent is a tanning agent.

In one embodiment of the combinations described above, the like acting agent is a phosphodiesterase inhibitor.

In one embodiment of the combinations described above, the phosphodiesterase inhibitor is a xanthine derivative. In another embodiment, the phosphodiesterase inhibitor is methylxanthine. In yet another embodiment, the phosphodiesterase inhibitor is cipamfylline.

In one embodiment of the combinations described above, the like acting agent is selected from psoralens. In another embodiment, the like acting agent is selected from furocoumarins.

In one embodiment of the combinations described above, the like acting agent is a self tanning agent.

In one embodiment of the combinations described above, the like acting agent is dihydroxyacetone.

In one embodiment of the combinations described above, the like acting agent is ultraviolate light.

In one embodiment of the combinations described above, the like acting agent is an agent that increases skin melanin content.

In one embodiment of the combinations described above, the like acting agent is an agent that darkens the skin.

In one embodiment of the combinations described above, the like acting agent is a dihydroxyacetone based tanner.

In one embodiment of, with respect to the additional active agent described above, the additional active agent is melanocyte stimulating hormone or an analogue or fragment thereof.

In another embodiment of the combination described above, the additional pharmaceutical or cosmetic agent is a skin care active agent. In some embodiments, the skin care active agent is an abrasive, an absorbent, an astringent, an aesthetic component, such as fragrances, pigments, colorings/colorants, essential oils, skin sensates, astringents and other aesthetic components, an antioxidant, a reducing agent, a sequestrant, a skin darkening or skin tanning agent, a skin conditioning agent, for example humectants and emollients, a skin soothing agent, a skin healing agent, such as pathenol and derivatives, aloe vera, pantothenic acid, allantoin, bisbolol, dipotassium glycyrrhizinate, skin treating agents, vitamins and derivatives, such as a retinoid, or mixtures thereof. In some embodiments, the retinoid is retinol, retinal, retinol esters, retinyl propionate, retinoic acid, retinyl palmitate, or mixtures thereof.

In a further aspect, also provided are methods for preventing, treating, ameliorating or managing a disease or condition involving aberrant melanogenesis, which comprises administering to a patient in need or desirous of such prevention, treatment, amelioration or management, a pharmaceutical composition comprising a prophylactically or therapeutically effective melanogenesis-enhancing amount of the combination as stated and set forth above, wherein the like acting agent is a pharmaceutically active agent. More particularly, the like-acting agent is a skin darkening or skin tanning compound.

In a further aspect, also provided is a method for altering or restoring pigmentation in mammalian skin, hair, wool or fur comprising administering to the mammalian skin, hair, wool or fur an amount of a composition comprising a pigment restoring or altering-effective amount of the combination as stated and set forth above, wherein the like acting agent is a cosmetically active agent. More particularly, the like-acting agent is a skin darkening or skin tanning compound.

In a further aspect, also provided is a method for enhancing melanin synthesis in melan-a cells comprising administering to the melan-a cells an effective amount of a compound of the formula I.

In a further aspect, also provided is a composition useful in for preventing skin damage due to UV irradiation comprising a pharmaceutically acceptable carrier and an effective amount of a compound of invention.

In a further aspect, also provided is a composition for darkening the skin or hair comprising a carrier and an effective amount of a compound of formula I.

In a further aspect, also provided is a method of darkening the skin or hair comprising topically applying thereto a composition comprising a skin-darkening effective amount of a compound of formula I.

In a further aspect, also provided is a self-tanning composition comprising a carrier and an effective amount of a compound of formula I.

In a further aspect, also provided is a method of self-tanning of the skin comprising topically applying thereto a composition comprising a self-tanning effective amount of a compound of formula I.

In a further aspect, also provided is a skin tanning composition comprising a carrier and an effective amount of a compound of formula I.

In a further aspect, also provided is a method of skin tanning of the skin comprising topically applying thereto a composition comprising a skin tanning effective amount of a compound of formula I.

In a further aspect, also provided is a method for promoting pigmentation of the skin, the body hair and/or the cranial hair, comprising topically applying thereto a composition comprising an effective amount of a compound of formula I.

In a further aspect, also provided is a method of stimulating melanogenesis of the skin, the body hair and/or the cranial hair, comprising topically applying thereto a composition comprising an effective amount of a compound of formula I.

In a further aspect, also provided is a method of increasing the pigmentation of mammalian skin, hair, wool or fur comprising topically applying thereto a composition comprising an effective amount of a compound of formula I.

The methods and compositions disclosed herein contemplate the use of one or more of the compounds listed herein as an active ingredient(s) for various uses. In a particular embodiment, the active ingredient(s) is combined with an acceptable carrier to form a topical formulation for application to the skin, for example, for cosmetic and/or therapeutic dermatological uses. Topical formulations may include ointments, lotions, pastes, creams, gels, drops, suppositories, sprays, liquids, foams, shampoos, powders, antiperspirants, deodorants, rinses, soaps, topical make-up products, including but not limited to face power, foundation, rouge, eye shadow, mascara, eyeliner or lipstick, UV-protective products, which may include sunscreens, lotions or creams, and transdermal patches. Thickeners, diluents, emulsifiers, dispersing aids or binders may be used as needed. Preferably, one function of the carrier is to enhance skin penetration of the active ingredient(s), and should be capable of delivering the active ingredient(s) to melanocytes under in vivo conditions. Suitable carriers are well known to skilled practitioners, and include liposomes, ethanol, dimethylsulfoxide (DMSO), petroleum jelly, (petrolatum), mineral oil (liquid petrolatum), water, dimethylformamide, dekaoxyethylene-oleylether, oleic acid, 2-pyrrolidone and Azone® brand penetration promoter (Upjohn). A particular composition may be formulated to include an active ingredient(s) as described in Table I, with one of 2-pyrrolidone, oleic acid and/or Azone® added to enhance penetration, solubilized in a base of water, ethanol, propanol and/or propylene glycol.

As indicated above, vehicles comprising liposomes may be used for topical delivery of some of the compositions disclosed herein. Depending on the composition, and at the discretion of a skilled practitioner, such liposomes may be non-ionic and contain a) glycerol dilaurate (preferably in an amount of between about 5% and about 70% by weight); b) compounds having the steroid backbone found in cholesterol (preferably in an amount of between about 5% and about 45% by weight); and c) one or more fatty acid ethers having from about 12 to about 18 carbon atoms preferably in an amount of between about 5% and about 70% by weight collectively), wherein the constituent compounds of the liposomes are preferably in a ratio of about 37.5:12.5:33.3:16.7. For some compositions, liposomes comprised of glycerol dilaurate/cholesterol/polyoxyethylene-10-stearyl ether/polyoxyethylene-9-lauryl ether (GDL liposomes) are preferred. Liposomes may be present in an amount, based upon the total volume of the composition, of from about 10 mg/mL to about 100 mg/mL, and more preferably from about 20 mg/mL to about 50 mg/mL. A ratio of about 37.5:12.5:33.3:16.7 may be used to particular advantage. Suitable liposomes may be prepared in accordance with standard methods commonly used in the art.

The above described composition may be prepared by combining the desired components in a suitable container and mixing them under ambient conditions in any conventional high shear mixing means well known in the art for non-ionic liposome preparations, such as those disclosed in Niemiec et al. (Pharm. Res. 12:1 184-88 (1995)), which is incorporated by reference herein in its entirety. The presence of such liposomes enhances the depigmenting capabilities of some compositions.

Oil-in-water emulsions, water-in-oil emulsions, solvent-based formulations and aqueous gels known to those of skill in the art may also be utilized as vehicles for the delivery of the disclosed compositions.

Depending on the specific application, the compositions disclosed herein may also include other active ingredients, as well as inert or inactive ingredients. In such alternative embodiments, the topically active pharmaceutical or cosmetic composition may be optionally combined with other ingredients such as moisturizers, cosmetic adjuvants, surfactants, foaming agents, conditioners, humectants, fragrances, viscosifiers, buffering agents, preservatives, sunscreens and the like.

Particular formulations may include at least one active ingredient (for example, a novel melanogenesis modifier described herein) or previously recognized, and particularly, like-acting agents, such as skin darkeners or skin tanners, which may be known to those of skill in the art. Agents known to possess similar activities and/or properties include, but are not limited to: phosphodiesterase inhibitors such as methylxanthines and cipamfylline, psoralens and other furocoumarins, dihydroxyacetone-based self tanners, and ultraviolet light.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved, or a cosmetically desired degree of melanogenesis modification (e.g., increase in pigmentation) is achieved, depending on the application. One of ordinary skill may readily determine optimum dosages, dosing methodologies and repetition rates. In general, it is contemplated that the compositions disclosed herein will have a concentration of a melanogenesis promoter of from about 0.01% to about 50%, preferably from about 0.03% to about 10%. In some embodiments, the compositions disclosed herein will have a concentration of melanogenesis promoter of from about 0.1% to about 25%, or from about 1% to about 10%. In other embodiments, the compositions disclosed herein will have a concentration by weight of from about 0.1% to about 75%, from about 0.5% to about 60%, from about 0.5% to about 50%, from about 0.5% to about 40%, from about 0.5% to about 30%, from about 0.5% to about 20%, from about 0.5% to about 10%, from about 1% to about 75%, from about 1% to about 60%, from about 1% to about 50%, from about 1% to about 40%, from about 1% to about 30%, from about 1% to about 20%, from about 1% to about 10%, from about 5% to about 75%, from about 5% to about 60%, from about 5% to about 50%, from about 5% to about 40%, from about 5% to about 30%, from about 5% to about 20%, from about 5% to about 10%, from about 10% to about 75%, from about 10% to about 60%, from about 10% to about 50%, from about 10% to about 40%, from about 10% to about 30%, from about 10% to about 20%, and from about 10% to about 15%. In some embodiments, the compositions disclosed herein will have a concentration of melanogenesis promoter of 0.1%, 0.5%, 0.75%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 10.5%, 11%, 11.5%, 12%, 12.5%, 13%, 13.5%, 14%, 14.5%, 15%, 16%, 17%, 18%, 19%, 20%, 25%, 30%, 35% 40%, 45% or 50%.

It is also contemplated that the compositions disclosed herein may contain from about 0.01 mg to about 100 mg of melanogenesis promoter, preferably about 0.1 mg to about 10 mg of melanogenesis promoter. In some embodiments, the compositions disclosed herein may contain from about 0.05 to about 5 mg of melanogenesis promoter, or from about 0.1 to about 3 mg of melanogenesis promoter. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of melanogenesis promoter. In some embodiments, the compositions disclosed herein will contain from about 0.3 mg to about 0.75 mg of melanogenesis promoter.

It is further contemplated that the compositions disclosed herein will have a concentration of melanogenesis promoter of from about 0.01 mg/ml to about 50 mg/ml, preferably from about 0.1 mg/ml to about 10 mg/ml. In some embodiments, the compositions disclosed herein will have a concentration of melanogenesis promoter of from about 0.1 mg/ml to about 5 mg/ml, or from about 0.3 mg/ml to about 3 mg/ml. In some embodiments, the compositions will have a concentration of melanogenesis promoter of from about 0.1 to about 50 mg/ml, from about 0.1 to about 45 mg/ml, from about 0.1 to about 40 mg/ml, from about 0.1 to about 35 mg/ml, from about 0.1 to about 30 mg/ml, from about 0.1 to about 25 mg/ml, from about 0.1 to about 20 mg/ml, from about 0.1 to about 15 mg/ml, from about 0.1 to about 10 mg/ml, from about 0.1 to about 5 mg/ml, 0.5 to about 50 mg/ml, from about 0.5 to about 45 mg/ml, from about 0.5 to about 40 mg/ml, from about 0.5 to about 35 mg/ml, from about 0.5 to about 30 mg/ml, from about 0.5 to about 25 mg/ml, from about 0.5 to about 20 mg/ml, from about 0.5 to about 15 mg/ml, from about 0.5 to about 10 mg/ml, from about 0.5 to about 5 mg/ml, 1.0 to about 50 mg/ml, from about 1.0 to about 45 mg/ml, from about 1.0 to about 40 mg/ml, from about 1.0 to about 35 mg/ml, from about 1.0 to about 30 mg/ml, from about 1.0 to about 25 mg/ml, from about 1.0 to about 20 mg/ml, from about 1.0 to about 15 mg/ml, from about 1.0 to about 10 mg/ml, from about 1.0 to about 5 mg/ml, 2.5 to about 50 mg/ml, from about 2.5 to about 45 mg/ml, from about 2.5 to about 40 mg/ml, from about 2.5 to about 35 mg/ml, from about 2.5 to about 30 mg/ml, from about 2.5 to about 25 mg/ml, from about 2.5 to about 20 mg/ml, from about 2.5 to about 15 mg/ml, from about 2.5 to about 10 mg/ml, from about 2.5 to about 5 mg/ml. In some embodiments, the compositions disclosed herein will have a concentration of melanogenesis promoter of 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 13, 13.5, 14, 14.5, 15, 16, 17, 18, 19, 20, 25, 30, 35 40, 45 or 50 mg/ml.

In general, melanogenesis promoters or compounds that increase or promote melanin production and pigmentation in mammalian skin, hair, fur or wool are useful in, for example, the darkening or tanning of skin, hair, wool or fur for cosmetic purposes, or the treatment of hypopigmentation or uneven pigmentation disorders. For such pigmentation applications, the formulation and dosing would be as described above.

In certain aspects, prodrugs and derivatives of the disclosed compounds are provided. Prodrugs are derivatives of the compounds which have metabolically cleavable groups and become by solvolysis or under physiological conditions the compounds which are pharmaceutically active, in vivo. Such examples include, but are not limited to, choline ester derivatives and the like, N-alkylmorpholine esters and the like.

Other derivatives of the compounds have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the disclosed compounds are preferred prodrugs. In some cases it is desirable to prepare double ester type prodrugs such as (acyloxy)alkyl esters or ((alkoxycarbonyl)oxy)alkylesters.

Preferred are the substituted or unsubstituted $C_1$ to $C_8$ alkyl, substituted or unsubstituted $C_2$-$C_8$ alkenyl, aryl, substituted or unsubstituted $C_7$-$C_{12}$ aryl, and substituted or unsubstituted $C_7$-$C_{12}$ arylalkyl esters of the compounds.

Also included are pharmaceutically acceptable acid addition and base salts of any of the aforementioned compounds of formulae I-V. The acids which are used to prepare the pharmaceutically acceptable acid addition salts of the aforementioned base compounds are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

The compounds useful that are basic in nature are capable of forming a wide variety of different salts with various inorganic and organic acids. Although such salts must be pharmaceutically acceptable for administration to animals, it is often desirable in practice to initially isolate a compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds disclosed herein are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds useful that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of the compounds disclosed herein are those that form non-toxic base salts with the acidic compounds of formulae I-IV. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

The appropriate dose regimen, the amount of each dose administered, and specific intervals between doses of the active compound will depend upon the particular active compound employed, the condition of the patient being treated, and the nature and severity of the disorder or condition being treated. Preferably, the melanogenesis promoter is administered in an amount and at an interval that results in the desired treatment of or improvement in the disorder or condition being treated.

Also provided are compounds useful to increase melanin production or to increase skin pigmentation, which correspond to compounds of the formulae I-V, and prodrugs, and analogs thereof, and to pharmaceutical compositions containing them, and including any pharmaceutically acceptable salts or solvates thereof.

Although methods and materials similar or equivalent to those described herein can be used in the practice or testing of the compositions and compounds disclosed herein, preferred methods and materials are described below. The materials, methods, and examples are illustrative only and not intended to be limiting. Other features and advantages will be apparent from the detailed description, examples, and the claims.

Plant Extract Containing Pubescine

In some embodiments, methods of enhancing melanogenesis are disclosed comprising administering to melanocytes an effective amount of a plant extract containing a melanogenesis promoter. In some embodiments, the melanogenesis promoter is an indole alkaloid melanogenesis promoter as in Formula I. In some embodiments, the melanogenesis promoter is pubescine or a pubescine derivative. In some embodiments, the plant extract is derived from a plant of the *Discaria pubescens* family. In some embodiments, the plant extract is derived from *Rauwolfia Nitida*. The plant species listed are not meant to be limiting as to the source of the melanogenesis promoter. Other plant species through which plant extracts can be made comprising a melanogenesis promoter, including a pubescine or a pubescine derivative, may also be used in conjunction with the disclosure herein.

In some embodiments, the plant extract is substantially purified or partially purified for concentration of the melanogenesis promoter. In yet other embodiments, the plant extract may be substantially liquefied or partially liquefied for administration to a patient in need thereof. The plant extract may also be processed to remove particulate matter prior to administration. In some embodiments, the plant extract contains about 0.1 to about 90%, about 0.5% to about 80%, about 1% to about 75%, about 5% to about 60%, about 10% to about 50%, about 25% to about 40% melanogenesis promoter. In other embodiments, the plant extract contains about 1% to about 80%, about 1% to about 70%, about 1% to about 60%, about 1% to about 50%, about 1% to about 40%, about 1% to about 30%, about 1% to about 20%, about 1% to about 10%, about 5% to about 80%, about 5% to about 70%, about 5% to about 60%, about 5% to about 50%, about 5% to about 40%, about 5% to about 30%, about 5% to about 20%, about 5% to about 10%, about 10% to about 80%, about 10% to about 70%, about 10% to about 60%, about 10% to about 50%, about 10% to about 40%, about 10% to about 30% or about 10% to about 20% melanogenesis promoter. In some embodiments, the plant extract contains about 0.5%, 1%, 5%, 10%, 15%, 20%, 25%, 30%, 35%, 40%, 45%, 50%, 55%, 60%, 65%, 70%, 75%, 80%, 85%, 90%, or 95% of a melanogenesis promoter.

In some embodiments, a plant extract is provided containing pubescine or a pubescine derivative for use as a promoter of melanogenesis. In some embodiments, provided are formulations of a plant extract containing pubescine or a pubescine derivative for enhancing melanogenesis. Also provided are methods for preventing, treating, ameliorating or managing a disease or condition involving aberrant melanogenesis, which comprises administering to a patient in need thereof or desirous of such prevention, treatment, amelioration, or management, a prophylactically, therapeutically or cosmetically effective melanogenesis-enhancing amount of a plant extract containing pubescine or a pubescine derivative. In some embodiments, provided are methods for altering or restoring pigmentation in mammalian skin, hair, wool, or fur comprising administering to a mammalian skin, hair, wool or fur an effective amount of a plant extract containing pubescine or a pubescine derivative. In some embodiments, the plant extract is derived from a plant of the *Discaria pubescens* family. In some embodiments, the plant extract is derived from *Rauwolfia Nitida*.

Pubescine is an alkaloid derived from extracts of certain plants including but not limited to *Discaria pubescens*. The plant seed from *Discaria pubescens* is used as an oral remedy for dysentery, diarrhea, intestinal worms, and irregular fever. In some embodiments, the plant extract is derived from *Rauwolfia Nitida*. In some embodiments, the plant extract is substantially purified or partially purified for concentration of the melanogenesis promoter. In yet other embodiments, the plant extract may be substantially liquefied or partially liquefied for administration to a patient in need thereof. The plant extract may also be processed to remove particulate matter prior to administration.

In general, it is contemplated that the plant extract compositions disclosed herein will comprise plant extract in an amount by weight, ranging from about 1% to about 75%, preferably from about 5% to about 50%, more preferably from about 10% to about 30%, and more preferably about 20%. In some embodiments, the compositions disclosed herein will have an amount of plant extract of from about 5% to about 35%, or from about 15% to about 25%. In some embodiments, the compositions disclosed herein will have an amount of plant extract of from about 5% to about 75%, from about 5% to about 70%, from about 5% to about 65%, from about 5% to about 60%, from about 5% to about 55%, from about 5% to about 50%, from about 5% to about 45%, from about 5% to about 40%, from about 5% to about 35%, from about 5% to about 30%, from about 5% to about 25%, from about 5% to about 20%, from about 5% to about 15%, from about 5% to about 10%, from about 10% to about 75%, from about 10% to about 70%, from about 10% to about 65%, from about 10% to about 60%, from about 10% to about 55%, from about 10% to about 50%, from about 10% to about 45%, from about 10% to about 40%, from about 10% to about 35%, from about 10% to about 30%, from about 10% to about 25%, from about 10% to about 20%, and from about 10% to about 15%. In some embodiments, the compositions disclosed herein will have an amount by weight of plant extract of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 32%, 34%, 35%, 36%, 38%, 40%, 45%, 50%, 55%, 60%, 65%, 70% or 75%. The amount of plant extract included in the disclosed compositions will depend on a number of factors, including the amount of melanogenesis promoter, including pubescine or a pubescine derivative, contained in the plant extract preparation. Testing of the plant extract preparations to determine the amount of melanogenesis promoter included in each preparation is contemplated within the scope of the embodiments described herein.

It is also contemplated that the compositions disclosed herein may contain from about 10 mg to about 100 g of plant extract per 100 ml of composition, preferably about 1 g to about 50 g of plant extract per 100 ml of composition. In some embodiments, the compositions disclosed herein may contain from about 100 mg to about 50 g of plant extract per 100 ml of composition, or from about 1 g to about 20 g of plant extract per 100 ml of composition. In some embodiments, the compositions disclosed herein may contain from about 100 mg to about 50 g, from about 100 mg to about 45 g, from about 100 mg to about 40 g, from about 100 mg to about 35 g, from about 100 mg to about 30 g, from about 100 mg to about 25 g, from about 100 mg to about 20 g, from about 100 mg to about 15 g, from about 100 mg to about 10 g, from about 100 mg to about 5 g, from about 100 mg to about 1 g, 1 g to about 50 g, from about 1 g to about 45 g, from about 1 g to about 40 g, from about 1 g to about 35 g, from about 1 g to about 30 g, from about 1 g to about 25 g, from about 1 g to about 20 g, from about 1 g to about 15 g, from about 1 g to about 10 g, from about 1 g to about 5 g, from about 2.5 g to about 50 g, from about 2.5 g to about 45 g, from about 2.5 g to about 40 g, from about 2.5 g to about 35 g, from about 2.5 g to about 30 g, from about 2.5 g to about 25 g, from about 2.5 g to about 20 g, from about 2.5 g to about 15 g, from about 2.5 g to about 10 g, and from about 2.5 g to about 5 g of plant extract per 100 ml of composition. In some embodiments, the compositions disclosed herein will contain from about 0.5 g, 1 g, 2 g, 3 g, 4 g, 5 g, 6 g, 7 g, 8 g, 9 g, 10 g, 11 g, 12 g, 13 g, 14 g, 15 g, 16 g, 17 g, 18 g, 19 g, 20 g, 21 g, 22 g, 23 g, 24 g, 25 g, 26 g, 27 g, 28 g, 29 g, 30 g, 32 g, 35 g, 37 g, 40 g, 45 g, 50 g, 55 g, 60 g, 65 g, 70 g or 75 g of plant extract per 100 ml of composition.

In other embodiments, provided are combinations of a plant extract containing pubescine or a pubescine derivative and a like-acting agent. One example of such plant extract is extract derived from *Discaria pubescens*. The like-acting agent can be any cosmetic ingredient or a pharmacologically active agent disclosed herein. Also provided are pharmaceutical compositions useful in treating disease for which a melanogenesis promoter is indicated, comprising a therapeutically effective amount of a plant extract containing pubescine or a pubescine derivative in combination with a like-acting agent. In some embodiments, the pharmaceutical composition comprising a plant extract containing pubescine or a pubescine derivative in combination with a like-acting agent is a topical formulation for cosmetic or dermatological use.

In still other embodiments, methods are provided for preventing, treating, ameliorating or managing a disease or condition involving aberrant melanogenesis, which comprises administering to a patient in need thereof or desirous of such prevention, treatment, amelioration or management, a pharmaceutical or cosmetic composition comprising prophylactically, therapeutically or cosmetically effective melanogenesis-enhancing amount of a combination of a plant extract containing pubescine or a pubescine derivative with a like-acting agent. In still other embodiments, also provided are methods for altering or restoring pigmentation in mammalian skin, hair, wool or fur comprising administering to a mammalian skin, hair, wool or fur an amount of a composition comprising a pigment-restoring or altering-effective amount of a combination of a plant extract containing pubescine or a pubescine derivative with a like-acting agent. In some embodiments, the like-acting agent is a skin darkening compound.

Methods of Enhancing Melanogenesis

As stated above, the compounds disclosed herein can be used to increase the pigmentation of mammalian skin, hair, wool or fur using the compounds of the invention. This invention further relates to use of the indole alkaloid compounds as tanning agents, skin or hair darkening agents, and as agents to prevent skin damage due to UV irradiation.

The terms "treatment", "therapeutic use", "cosmetic use" and "medicinal use" shall refer to any and all uses of the disclosed compositions which remedy a disease state, one or more symptoms or one or more effects, or otherwise prevent, hinder, retard, or reverse the progression of disease or one or more other undesirable symptoms or effects in any way whatsoever.

Further provided are methods and pharmaceutical and/or cosmetic compositions for increasing skin pigmentation comprising the use of the present compounds either alone or in combination with other, like-acting agents.

The term "about" is used herein to mean approximately, roughly, around, or in the region of. When the term "about" is used in conjunction with a numerical range, it modifies that range by extending the boundaries above and below the numerical values set forth.

By the phrase "increase in melanin production" or "enhancing melanogenesis" is meant a detectable increasing of the amount of melanin synthesized de novo by a melanocyte exposed to a compound disclosed herein, as compared with the amount of melanin synthesized de novo by a control, untreated melanocyte. The term "increasing" as presently used refers, in a first instance, to an increase of at least about 10%, in a further instance, to a increase of at least about 25%, and in a still further instance, to a increase of at least about 50%, in the amount of melanin synthesized de novo.

As one skilled in the art would know in view of this disclosure, the compounds used in the methods disclosed herein may be used alone or in combination with each other.

Thus, the disclosure relates both to methods of modifying, and particularly enhancing the pigmentation of skin in which the active compound used, or a pharmaceutically acceptable salt thereof, and one or more of the other active ingredients referred to above are administered together, as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and the nature and severity of the disorder or condition being treated. Such additional active ingredients will generally be administered in amounts less than or equal to those for which they are effective as single topical therapeutic agents. The FDA approved dosages for such active agents that have received FDA approval for administration to humans are publicly available.

By the phrase "increasing skin pigmentation" is meant a detectable increase in the amount of melanin in the skin, preferably causing a darkening of the skin as a result of a increasing of the amount of melanin synthesized de novo. The term "increasing" as presently used refers, in a first instance, to an increase of at least about 10%, in a further instance, to a increase of at least about 25%, and in a still further instance, to a increase of at least about 50%, in the amount of melanin synthesized de novo. This increasing of melanin synthesized de novo is preferably visually distinguishable to the naked eye, i.e., would not require the aid of a microscope or other such means to detect its occurrence.

Also provided are methods for an increase in skin pigmentation by contacting the skin topically with an effective amount of a compound that alters late endosomal/lysosomal trafficking in the skin. Useful compounds for these methods include those disclosed above.

Pharmaceutical Applications

For pharmaceutical uses, it is preferred that the compounds disclosed herein are part of a pharmaceutical composition. Pharmaceutical compositions, comprising an effective amount of such a compound in a pharmaceutically acceptable carrier, can be administered to a patient, person, or animal having a disease, disorder, or condition which is of a type that e.g., underproduces melanin.

The amount of compound which will be effective in the treatment of a particular disease, disorder, or condition will depend on the nature of the disease, disorder, or condition, and can be determined by standard clinical techniques. Where possible, it is desirable to determine in vitro the cytotoxicity of the compound to the tissue type to be treated, and then in a useful animal model system prior to testing and use in humans.

The compound can be administered for the increase of melanin synthesis by any means that results in contact of the active agent with its site of action in the body of a mammal. The compounds can be administered by any conventional means available for use in conjunction with pharmaceuticals, either as individual therapeutic agents or in a combination of therapeutic agents. Each can be administered alone, but is preferably administered with a pharmaceutical carrier selected on the basis of the chosen route of administration and standard pharmaceutical practice. The pharmaceutical compositions can be adapted for oral, parenteral, rectal, and preferably topical, administration, and can be in unit dosage form, in a manner well known to those skilled in the pharmaceutical art. Parenteral administration includes but is not limited to, injection subcutaneously, intravenously, intraperitoneally or intramuscularly. However, topical application is preferred.

Cosmetic Applications

In addition to pharmaceutical uses, the methods disclosed herein are useful for cosmetic purposes. Cosmetic applications for methods disclosed herein include the topical application of compositions containing one or more compounds to enhance or otherwise alter the visual appearance of skin or hair. Occurrences in the skin or hair of noticeable findings as a result of melanin underproduction can be treated using the methods disclosed herein. Thus, and as discussed above, the compounds and compositions can be used to achieve improvements in skin or hair appearance, as by bronzing, darkening or deepening the same, adding or enhancing luster, and the like. Suitable formulations for these purposes can be prepared by those skilled in the art, and such details of preparation are considered within the scope.

The phrases "pharmaceutical applications" and "cosmetic applications" are not meant to imply mutual exclusivity. In some embodiments, a composition may be applied to both a "pharmaceutical application" and a "cosmetic application" dependent upon the need and course of action called for.

Endpoints and Dosages

An effective dosage and treatment protocol can be determined by conventional means, starting with a low dose in laboratory animals and then increasing the dosage while monitoring the effects, and systematically varying the dosage regimen as well. Animal studies, preferably mammalian studies, are commonly used to determine the maximal tolerable dose, or MTD, of a bioactive agent per kilogram weight. Those skilled in the art can extrapolate doses for efficacy and avoidance of toxicity to other species, including humans.

Before human studies of efficacy are undertaken, Phase I clinical studies in normal subjects can help establish safe doses. Numerous factors can be taken into consideration by a clinician when determining an optimal dosage for a given subject. Primary among these is the toxicity and half-life of the chosen compound that affects or mimics P protein function or that inhibits late endosomal/lysosomal trafficking. Additional factors include the size of the patient, the age of the patient, the general condition of the patient, the particular disease, condition, or disorder being treated, the severity of the disease, condition, or disorder being treated, the presence of other drugs in the patient, the effect desired, and the like. The trial dosages would be chosen after consideration of the results of animal studies and the clinical literature.

One of ordinary skill in the art will appreciate that the endpoint chosen in a particular case will vary according to the disease, condition, or disorder being treated, the outcome desired by the patient, subject, or treating physician, and other factors. Where the composition is being used for cosmetic purposes, such as to darken skin color such as, for example, to reverse hypopigmentation, or to modify hair color, any one of a number of endpoints can be chosen.

In such instance, endpoints can be defined subjectively such as, for example, when the subject is simply "satisfied" with the results of the treatment. For pharmacological applications, the endpoint can be determined by the patient's, or the treating physicians, satisfaction with the results of the treatment. Alternatively, endpoints can be defined objectively. For example, the patient's or subject's skin or hair in the treated area can be compared to a color chart. Treatment is terminated when the color of the skin or hair in the treated area is similar in appearance to a color on the chart. Alternatively, the reflectance of the treated skin or hair can be measured, and treatment can be terminated when the treated skin or hair attains a specified reflectance. Alternatively, the melanin content of the treated hair or skin can be measured. Treatment can be terminated when the melanin content of the treated hair or skin reaches a specified value. Melanin content can be determined in any way known to the art, including by histological methods, with or without enhancement by stains for melanin.

Methods of Administration

The disclosed compounds can be administered topically, e.g., as patches, ointments, creams, gels, lotions, sera, solutions, foams, masks or transdermal administration. The compounds can also be administered orally in solid or semi-solid dosage forms, such as hard or soft-gelatin capsules, tablets, or powders, or in liquid dosage forms, such as elixirs, syrups, or suspensions. Additionally, the compounds can also be administered parenterally, in sterile liquid dosage forms or in suppository form.

Because in vivo use is contemplated, the composition is preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

Useful pharmaceutical dosage forms for administration of the present compounds are described below.

The pharmaceutical compositions can be applied directly to the skin. Alternatively, they can be delivered by various transdermal drug delivery systems, such as transdermal patches as known in the art. For example, for topical administration, the active ingredient can be formulated in a solution, gel, lotion, ointment, cream, suspension, foam, mask, paste, liniment, powder, tincture, aerosol, patch, or the like in a pharmaceutically or cosmetically acceptable form by methods well known in the art. The composition can be any of a variety of forms common in the pharmaceutical or cosmetic arts for topical application to animals or humans, including solutions, lotions, sprays, creams, ointments, salves, gels, etc., as described below. Preferred agents are those that are viscous enough to remain on the treated area, those that do not readily evaporate, and/or those that are easily removed by rinsing with water, optionally with the aid of soaps, cleansers and/or shampoos. Actual methods for preparing topical formulations are known or apparent to those skilled in the art, and are described in detail in *Remington's Pharmaceutical Sciences,* 1990 (supra); and *Pharmaceutical Dosage Forms and Drug Delivery Systems,* 6th ed., Williams & Wilkins (1995).

In order to enhance the percutaneous absorption of the active ingredients, one or more of a number of agents can be added in the topical formulations including, but not limited to, dimethylsulfoxide, dimethylacetamide, dimethylformamide, surfactants, azone, alcohol, acetone, propylene glycol and polyethylene glycol. In addition, physical methods can also be used to enhance transdermal penetration such as, e.g., by iontophoresis or sonophoresis. Alternatively, or in addition, liposomes may be employed.

A topically applied composition contains a pharmaceutically effective amount of at least one of the disclosed compounds as described herein, and those ingredients as are necessary for use as a carrier, such as an emulsion, a cream, an ointment, an ophthalmic ointment, an aqueous solution, a lotion or an aerosol. Non-limiting examples of such carriers are described in more detail below and may be found in International Patent Publication WO 00/62742, published Oct. 26, 2000, U.S. Pat. No. 5,691,380 to Mason et al., issued on Nov. 25, 1997 and U.S. Pat. No. 5,968,528 to Deckner et al., issued on Oct. 19, 1999, U.S. Pat. No. 4,139,619 to Chidsey, III, issued on Feb. 13, 1979 and U.S. Pat. No. 4,684,635 to Orentreich et al., issued on Aug. 4, 1987 which are incorporated herein by reference. Suitable pharmaceutical carriers are further described in *Remington's Pharmaceutical Sciences,* 17th ed., Mack Publishing Company, Easton, Pa. (1990) a standard reference text in this field.

The pharmaceutical compositions may also include optional components. Such optional components should be suitable for application to keratinous tissue, that is, when incorporated into the composition, they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds disclosed herein. The CTFA Cosmetic Ingredient Handbook, Second Edition (1992) describes a wide variety of non-limiting cosmetic and pharmaceutical ingredients commonly used in the skin care industry, which are suitable for use in the compositions disclosed herein. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

In addition to the pharmaceutically effective amount of an agent disclosed herein, the topical compositions also comprise a dermatologically acceptable carrier. The phrase "dermatologically acceptable carrier", as used herein, means that the carrier is suitable for topical application to the skin, i.e., keratinous tissue, has good aesthetic properties, is compatible with the active agents disclosed herein and any other components, and will not cause any safety or toxicity concerns. A safe and effective amount of carrier is from about 10% to about 99.99%, preferably from about 30% to about 99.9%, more preferably from about 50% to about 98%, and most preferably from about 60% to about 95% of the composition.

The carrier utilized in the disclosed compositions can be in a wide variety of forms. These include emulsion carriers, including, but not limited to, oil-in-water, water-in-oil, water-in-oil-in-water, and oil-in-water-in-silicone emulsions, a cream, an ointment, an ophthalmic ointment, an aqueous solution, a lotion or an aerosol. As will be understood by the skilled artisan, a given component will distribute primarily into either the water or oil/silicone phase, depending on the water solubility/dispersibility of the component in the composition.

Emulsions generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560, issued to Dickert, et al. Aug. 28, 1973; U.S. Pat. No. 4,421,769, issued to Dixon, et al. Dec. 20, 1983; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions as disclosed herein comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compounds disclosed herein in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g. mineral oil, vegetable oils, synthetic oils. semisynthetic oils, etc.

Useful topical compositions comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

Topical compositions typically comprise from about 25% to about 90%, preferably from about 40% to about 80%, more preferably from about 60% to about 80%, water in the dispersed aqueous phase by weight of the composition.

The water-in-silicone emulsions preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions comprise from about 0.5% to about 20%, more preferably from about 1% to about 10%, most preferably from about 1% to about 5%, by weight of the composition, of a structuring agent. The preferred structuring agents are selected from the group consisting of stearic acid, palmitic acid, stearyl alcohol, cetyl alcohol, behenyl alcohol, stearic; acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See, McCutcheon's. Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al. issued Dec. 20, 1983; and U.S. Pat. No. 3,755,560. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued Sep. 29, 1992; U.S. Pat. No. 5,151,210 to Steuri et al. issued Sep. 29, 1992; U.S. Pat. No. 5,120,532; U.S. Pat. No. 4,387,090; U.S. Pat. No. 3,155,591; U.S. Pat. No. 3,929,678; U.S. Pat. No. 3,959,461; McCutcheon's, Detergents & Emulsifiers (North American edition 1979) M.C. Publishing Co.; and Schwartz, et al., Surface Active Agents, Their chemistry and Technology, New York: Interscience Publishers, 1949.

Alternatively, other useful cationic emulsifiers include amino-amides. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions disclosed herein, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, Cosmetics, Science and Technology, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the embodiments disclosed herein generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

Ointments may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, Cosmetics, Science and Technology, 2nd Edition, Vol. 1, pp. 72-73 (1972), incorporated herein by reference, and/or an emollient. For example, an ointment may comprise from about 2% to about 10% of an emollient; from about 0.1% to about 2% of a thickening agent; and a pharmaceutically effective amount of an agent described herein.

By way of non-limiting example, 1000 g of topical cream is prepared from the following types and amounts of ingredients: a pharmaceutically effective amount of an agent disclosed herein, tegacid regular (150 g) (a self-emulsifying glyceryl monostearate from Goldschmidt Chemical Corporation, New York, N.Y.), polysorbate 80 (50 g), spermaceti (100 g), propylene glycol (50 g), methylparaben (1 g), and deionized water in sufficient quantity to reach 1000 gm. The tegacid and spermaceti are melted together at a temperature of 70-80° C. The methylparaben is dissolved in about 500 g of water and the propylene glycol, polysorbate 80, and 6-amino-1,2-dihydro-1-hydroxy-2-imino-4-piperidinopyrimidine free base are added in turn, maintaining a temperature of 75-80° C. The methylparaben mixture is added slowly to the tegacid and spermaceti melt, with constant stirring. The addition is continued for at least 30 minutes with additional stirring until the temperature has dropped to 40-45° C. Finally, sufficient water is added to bring the final weight to 1000 g and the preparation stirred to maintain homogeneity until cooled and congealed.

By way of non-limiting example, 1000 g of a topical ointment is prepared from the following types and amounts of ingredients: a pharmaceutically effective amount of an agent disclosed herein, zinc oxide (50 g), calamine (50 g), liquid petrolatum (heavy) (250 g), wool fat (200 g), and enough white petrolatum to reach 1000 g. Briefly, the white petrolatum and wool fat are melted and 100 g of liquid petrolatum added thereto. The pharmaceutically effective amount of an agent disclosed herein, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

By way of non-limiting example, 1000 g of an ointment, e.g., an ophthalmic ointment, containing a pharmaceutically effective amount of an agent disclosed herein is prepared from the following types and amounts of ingredients: a pharmaceutically effective amount of an agent disclosed herein, light liquid petrolatum (250 g), wool fat (200 g), and enough white petrolatum to reach 1000 g. Briefly, the pharmaceutically effective amount of an agent disclosed herein is finely divided and added to the light liquid petrolatum. The wool fat and white petrolatum are melted together, strained, and the temperature adjusted to 45-50° C. The liquid petrolatum slurry is added, and the ointment stirred until congealed.

By way of non-limiting example, 1000 ml of an aqueous solution containing a pharmaceutically effective amount of an agent disclosed herein is prepared from the following types and amounts of ingredients: a pharmaceutically effective amount of an agent disclosed herein, polyethylene glycol 4000 (120 g) myristyl-gamma-picolinium chloride (0.2 g), polyvinylpyrrolidone (1 g), and enough deionized water to reach 1000 milliliters. Briefly, the ingredients are dissolved in the water and the resulting solution is sterilized by filtration.

By way of non-limiting example, 1000 g of lotion containing a pharmaceutically effective amount of an agent disclosed herein is prepared from the following types and amounts of ingredients: a pharmaceutically effective amount of an agent disclosed herein, N-methyl pyrolidone (40 g), and enough propylene glycol to reach 1000 g.

By way of non-limiting example, an aerosol containing a pharmaceutically effective amount of an agent disclosed herein is prepared from the following types and amounts of materials: a pharmaceutically effective amount of an agent disclosed herein, absolute alcohol (4.37 g), Dichlorodifluoroethane (1.43 g) and dichlorotetrafluoroethane (5.70 g). Briefly, the pharmaceutically effective amount of an agent disclosed herein is dissolved in the absolute alcohol and the resulting solution filtered to remove particles and lint. This solution is chilled to about −30° C. Then, to this is added the chilled mixture of dichlorodifluoromethane and dichlorotetrafluoroethane.

For oral administration, Gelatin capsules or liquid-filled soft gelatin capsules can contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, sterile water, oil, saline, aqueous dextrose (glucose), polysorbate and related sugar solutions and glycols such as propylene glycol or polyethylene glycols, are suitable carriers for parenteral solutions. Solutions or emulsions for parenteral administration preferably contain about 5-15% polysorbate 80 or lecithin, suitable stabilizing agents and, if necessary, buffer substances. Antioxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

As will be understood by those in the art, the compositions and pharmaceutical compositions may be provided in the form of a kit. Kits comprise one or more specific compositions and/or pharmaceutical compositions disclosed herein. Optionally, the kit further contains printed instructions as a label or package insert directing the use of such reagents to modify skin pigmentation, i.e., to darken skin as appropriate to the particular included composition. These compounds are provided in a container designed to prevent contamination, minimize evaporation or drying of the composition, etc. The compounds may or may not be provided in a preset unit dose or usage amount.

The following formulation examples illustrate representative pharmaceutical compositions that may be prepared in accordance with the embodiments disclosed herein, but are not meant to be limited to the following pharmaceutical compositions.

Formulation 1

Tablets

An effective amount of a compound as in Formulae I-V may be admixed as a dry powder with a dry gelatin binder in an approximate 1:2 weight ratio. A minor amount of magnesium stearate may be added as a lubricant. The mixture is formed into 240-270 mg tablets (80-90 mg of active compound per tablet) in a tablet press.

Formulation 2

Capsules

An effective amount of a compound as in Formulae I-V may be admixed as a dry powder with a starch diluent in an approximate 1:1 weight ratio. The mixture may be filled into 250 mg capsules (125 mg of active compound per capsule).

Formulation 3

Liquid

An effective amount of a compound as in Formulae I-V (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then added to produce a total volume of 5 mL.

Formulation 4

Tablets

An effective amount of a compound as in Formulae I-V may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

An effective amount of a compound as in Formulae I-V may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of a compound as in Formulae I-V (10-50 g of active compound) methylparaben (0.25 g), propylparaben (0.15 g), sodium lauryl sulfate (10 g), and propylene glycol (120 g) dissolved in water (about 370 g) is added and the resulting mixture would be stirred until it congeals.

General Synthetic Procedures

The indole alkaloid compounds as in Formulae I-V which comprise various known drugs or drug like molecules can be purchased from commercial sources and tested for their activities. The indole alkaloid compounds which are not commercially available can be prepared from readily available starting materials using various general methods and procedures known in the art.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

EXAMPLES

Example 1

Screening of Compounds in Cultured Murine Melanocytes

The Spectrum Collection library consisting of 2000 drug compounds or natural products was screened to identify novel pigmentation inhibitors or stimulators in cultured murine melanocytes (melan-a). Compounds were dissolved in dimethylsulfoxide (DMSO) to a final concentration of 10 mM. Screening was performed with cultured melanocytes in 24-well plates followed by melanin assay (see below). A minimum change of 50% in melanin formation was established as significant for a pigmentation inhibitor or stimulator. DMSO was used as a negative control and the widely used depigmenting agent, hydroquinone, was used as a positive control on every plate. Primary screening was performed at a final concentration of 1 µM and potential candidates from the primary screening were reconfirmed in duplicate at final concentrations of 1 and 5 µM.

Melan-a cells were plated at $5 \times 10^4$ cells per well in 1 ml of culture media in 24-well plates the day before adding the library compounds. All compounds were added at the indicated final concentrations. Cells were harvested after 72 hours of incubation, and melanin assay was performed.

For further test and mechanism of action studies, the compounds were purchased from either Sigma or MicroSource. These compounds were dissolved in dimethylsulfoxide (DMSO) to a final concentration of 10 mM, and were tested for their effect on melanin synthesis at the indicated final concentrations.

Example 2

Melanin Assay

For the primary and secondary screening, cells were harvested and dissolved in 200 µl of 2N NaOH in 20% DMSO at 70° C. A 180-µl aliquot of the resulting solution was measured for absorbance at 490 nm.

Cells are harvested in extraction buffer (1% Triton X-100, 50 mM Tris, 2 mM EDTA, 150 mM NaCl, pH 7.5) containing a complete protease inhibitor cocktail (Roche). The lysates were centrifuged at 14,000 rpm for 10 minutes at 4° C. BCA protein assay kit (Pierce) was used to measure the protein concentrations of the supernatants, and bovine serum albumin was used as a standard. The remaining pellets were incubated with 100 µl ethanol-ether (1:1) for 10 minutes at room temperature. After removing the ethanol-ether, the pellets were dissolved in 200 µl of 2N NaOH in 20% DMSO at 70° C. A 180-µl aliquot of the resulting solution was measured for absorbance at 490 nm. The melanin contents were normalized to the total amount of protein.

Figure 2:
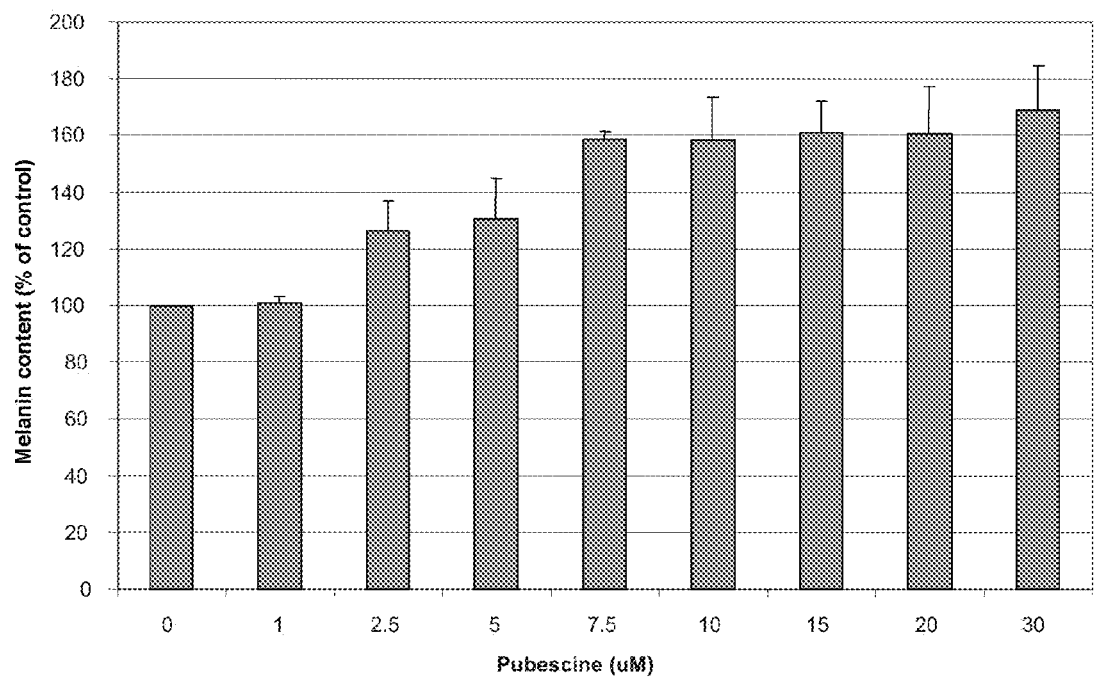
FIG. 2 is a bar graph presenting the melanine assay results for pubescine at various concentrations.

The compounds, their structures, and activity data expressed as % of control remaining are shown in Table 1, below (FIGS. 1 and 2).

TABLE 1

Activity Data for Compounds Useful as Melanogenesis Modifiers

| ID | Name | Structure | % of control after treatment @ 1 μM | % of control after treatment @ 5 μM |
|---|---|---|---|---|
| 1 | Corynanthine | 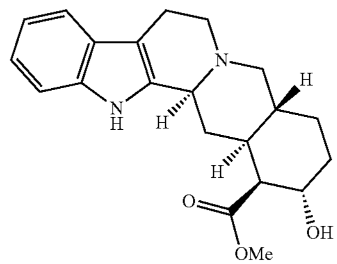 [SMILES: COC(=O)[C@H]1[C@H]2C[C@H]3c4[nH]c5ccccc5c4CCN3C[C@@H]2CC[C@@H]1O] | 1.11 | 2.11 |
| 2 | Ajmaline | 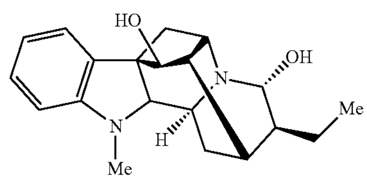 [SMILES: CC[C@H]1C2C[C@H]3C4N(C)c5ccccc5[C@]45CC([C@@H]2[C@@H]5O)N3[C@@H]1O] | 1.17 | 2.06 |
| 3 | Ajmalicine | 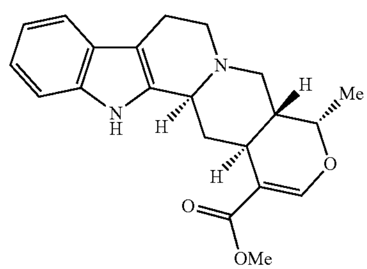 [SMILES: COC(=O)C1=CO[C@@H](C)[C@H]2CN3CCc4c([nH]c5ccccc45)[C@@H]3C[C@H]12] | 1.06 | 1.33 |
| 4 | Reserpine | 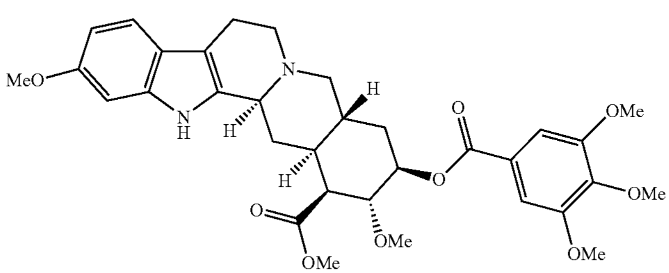 [SMILES: COC(=O)[C@H]1[C@H]2C[C@H]3c4[nH]c5cc(OC)ccc5c4CCN3C[C@@H]2C[C@@H](OC(=O)c2cc(OC)c(OC)c(OC)c2)[C@@H]1OC] | 1.17 | 1.33 |
| 5 | Reserpic Acid | 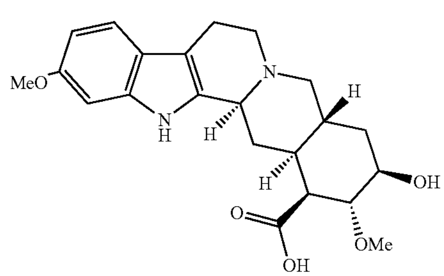 [SMILES: COc1ccc2c3c([nH]c2c1)[C@@H]1C[C@H]2[C@@H](C[C@@H](O)[C@H](OC)[C@H]2C(=O)O)CN1CC3] | 1.11 | 2.17 |

TABLE 1-continued

Activity Data for Compounds Useful as Melanogenesis Modifiers

| ID | Name | Structure | % of control after treatment @ 1 μM | % of control after treatment @ 5 μM |
|----|------|-----------|---------|---------|
| 6 | Pubescine | 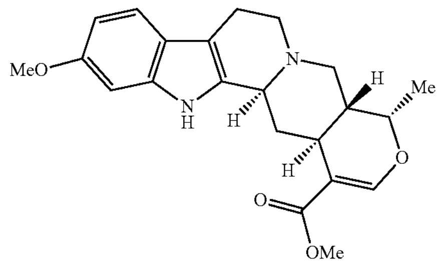 [SMILES: COC(=O)C1=CO[C@@H](C)[C@H]2CN3CCc4c([nH]c5cc(OC)ccc45)[C@@H]3C[C@H]12] | 1.72 | 2.67 |

Additional Pubescine Derivatives

The following additional pubescine derivatives can be prepared or commercially obtained and tested for their melanogenesis activity (Table 2).

TABLE 2

Additional Pubescine Derivatives

| ID | PUBCHEM COMPOUND CID | STRUCTURE | MW |
|----|---------------------|-----------|-----|
| 101 | 9995427 | 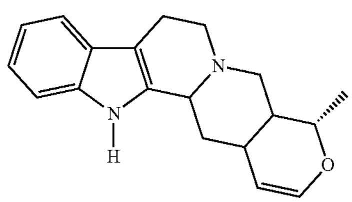 [SMILES: C[C@@H]1OC=CC2CC3c4[nH]c5ccccc5c4CCN3CC21] | 294.4 |
| 102 | 21771394 | 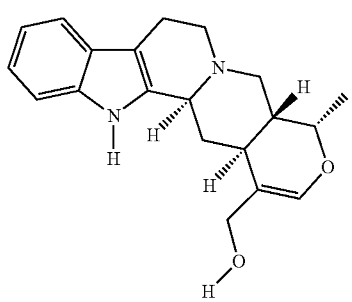 [SMILES: C[C@@H]1OC=C(CO)[C@H]2C[C@H]3c4[nH]c5ccccc5c4CCN3C[C@H]12] | 324.426 |
| 103 | 44269925 | 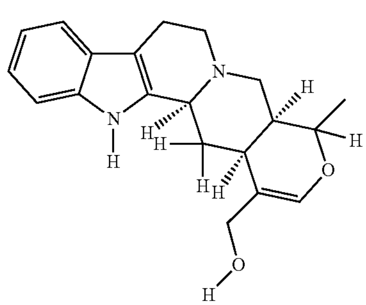 [SMILES: CC1OC=C(CO)[C@H]2C[C@H]3c4[nH]c5ccccc5c4CCN3C[C@@H]12] | 324.426 |

TABLE 2-continued

Additional Pubescine Derivatives

| ID | PUBCHEM COMPOUND CID | STRUCTURE | MW |
|---|---|---|---|
| 104 | 3010369 | 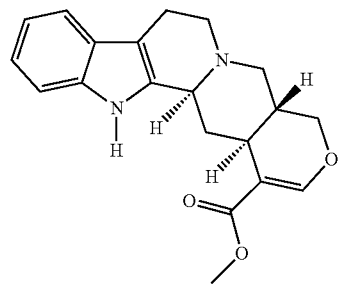 [SMILES: COC(=O)C1=COC[C@H]2CN3CCc4c([nH]c5ccccc45)[C@@H]3C[C@H]12] | 338.41 |
| 105 | 3055759 | 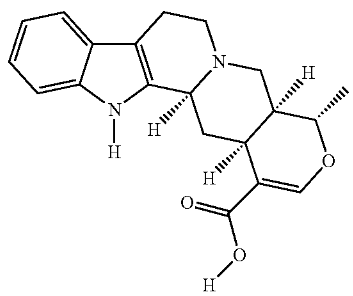 [SMILES: C[C@@H]1OC=C(C(=O)O)[C@H]2C[C@H]3c4[nH]c5ccccc5c4CCN3C[C@@H]12] | 338.41 |
| 106 | 10043579 | 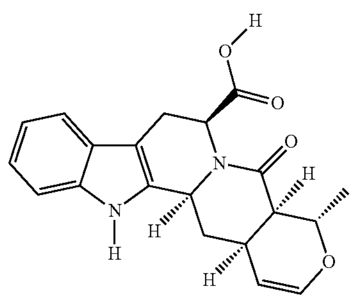 [SMILES: C[C@@H]1OC=C[C@H]2C[C@H]3c4[nH]c5ccccc5c4C[C@@H](C(=O)O)N3C(=O)[C@@H]12] | 352.393 |
| 107 | 72338 | 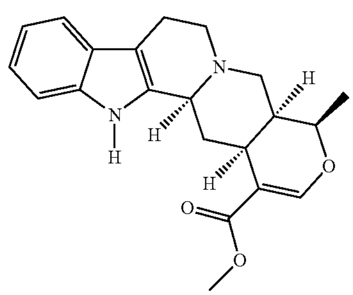 [SMILES: COC(=O)C1=CO[C@H](C)[C@@H]2CN3CCc4c([nH]c5ccccc45)[C@@H]3C[C@H]12] | 352.437 |
| 108 | 72340 | 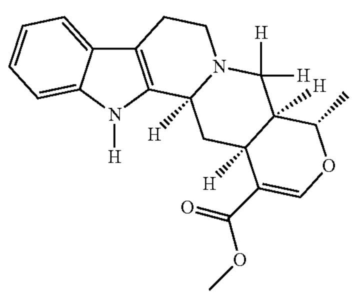 [SMILES: COC(=O)C1=CO[C@@H](C)[C@@H]2CN3CCc4c([nH]c5ccccc45)[C@@H]3C[C@H]12] | 352.437 |

TABLE 2-continued
Additional Pubescine Derivatives
| ID | PUBCHEM COMPOUND CID | STRUCTURE | MW |
|---|---|---|---|
| 109 | 179460 | 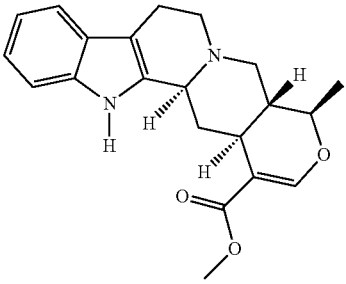 [SMILES: COC(=O)C1=CO[C@H](C)[C@H]2CN3CCc4c([nH]c5ccccc45)[C@@H]3C[C@H]12] | 352.437 |
| 110 | 179461 | 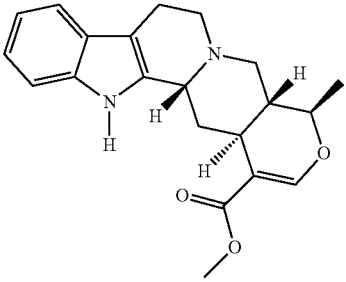 [SMILES: COC(=O)C1=CO[C@H](C)[C@H]2CN3CCc4c([nH]c5ccccc45)[C@H]3C[C@H]12] | 352.437 |
| 111 | 251561 | 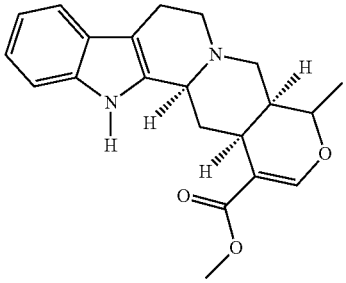 [SMILES: COC(=O)C1=COC(C)[C@@H]2CN3CCc4c([nH]c5ccccc45)[C@@H]3C[C@H]12] | 352.437 |
| 113 | 638248 | 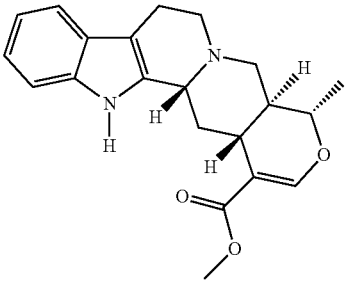 [SMILES: COC(=O)C1=CO[C@@H](C)[C@@H]2CN3CCc4c([nH]c5ccccc45)[C@H]3C[C@@H]12] | 352.437 |
| 114 | 969486 | 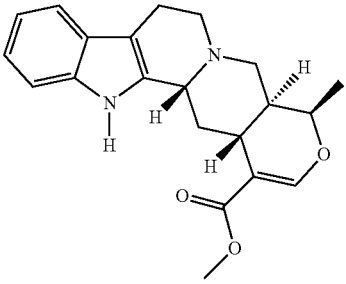 [SMILES: COC(=O)C1=CO[C@H](C)[C@@H]2CN3CCc4c([nH]c5ccccc45)[C@H]3C[C@@H]12] | 352.437 |

TABLE 2-continued
Additional Pubescine Derivatives
| ID | PUBCHEM COMPOUND CID | STRUCTURE | MW |
|---|---|---|---|
| 115 | 1268096 | 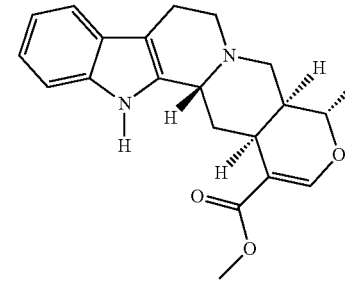 | 352.437 |
| 116 | 6101903 | 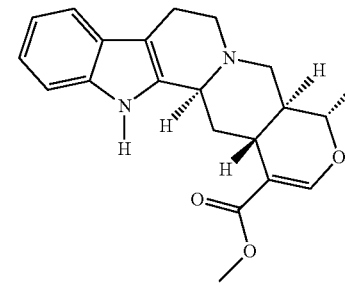 | 352.437 |
| 117 | 6419959 | 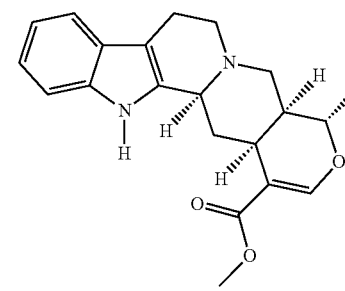 | 352.437 |
| 118 | 7072790 | 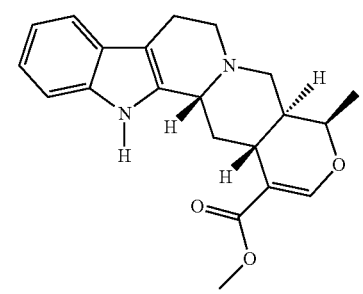 [SMILES: COC(=O)C1=CO[C@H](C)[C@@H]2CN3CCc4c([nH]c5ccccc45)[C@H]3C[C@@H]12] | 352.437 |
| 119 | 10473206 | 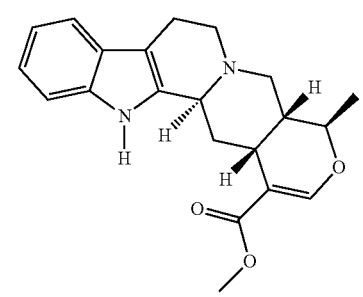 [SMILES: COC(=O)C1=CO[C@H](C)[C@H]2CN3CCc4c([nH]c5ccccc45)[C@@H]3C[C@@H]12] | 352.437 |

TABLE 2-continued

Additional Pubescine Derivatives

| ID | PUBCHEM COMPOUND CID | STRUCTURE | MW |
|---|---|---|---|
| 120 | 11416867 | 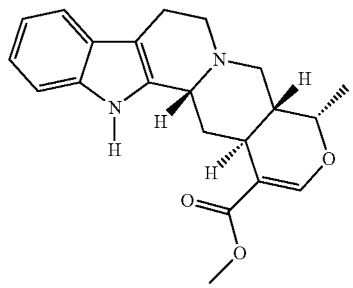 [SMILES: COC(=O)C1=CO[C@@H](C)[C@H]2CN3CCc4c([nH]c5ccccc45)[C@H]3C[C@H]12] | 352.437 |
| 121 | 12047508 | 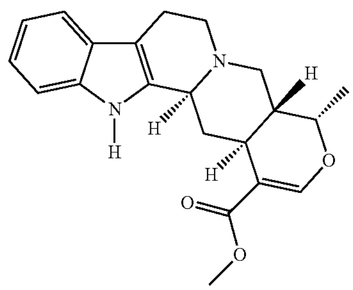 [SMILES: COC(=O)C1=CO[C@@H](C)[C@H]2CN3CCc4c([nH]c5ccccc45)[C@@H]3C[C@H]12] | 352.437 |
| 122 | 15558583 | 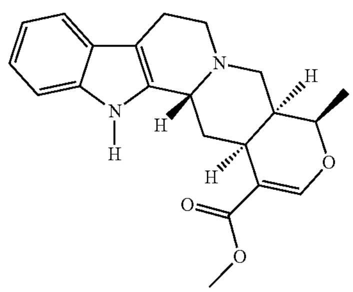 [SMILES: COC(=O)C1=CO[C@H](C)[C@@H]2CN3CCc4c([nH]c5ccccc45)[C@H]3C[C@H]12] | 352.437 |
| 123 | 20056669 | 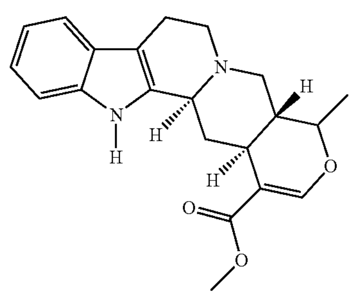 [SMILES: COC(=O)C1=COC(C)[C@H]2CN3CCc4c([nH]c5ccccc45)[C@@H]3C[C@H]12] | 352.437 |
| 124 | 44269728 | 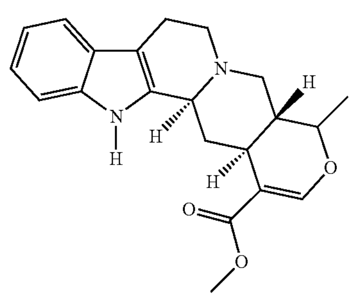 [SMILES: COC(=O)C1=COC(C)[C@H]2CN3CCc4c([nH]c5ccccc45)[C@@H]3C[C@H]12] | 352.437 |

TABLE 2-continued

Additional Pubescine Derivatives

| ID | PUBCHEM COMPOUND CID | STRUCTURE | MW |
|---|---|---|---|
| 125 | 3055398 | 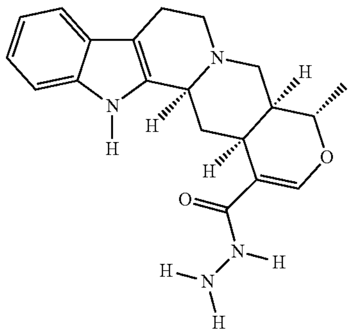 [SMILES: C[C@@H]1OC=C(C(=O)NN)[C@H]2C[C@H]3c4[nH]c5ccccc5c4CCN3C[C@@H]12] | 352.44 |
| 126 | 3055440 | 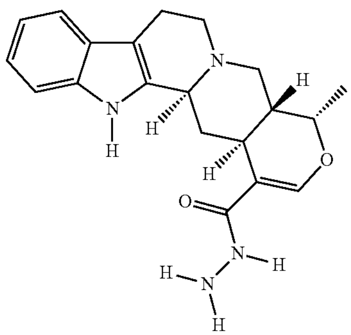 [SMILES: C[C@@H]1OC=C(C(=O)NN)[C@H]2C[C@H]3c4[nH]c5ccccc5c4CCN3C[C@H]12] | 352.44 |
| 127 | 6957653 | 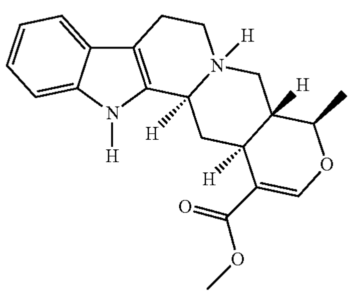 | 353.445 |
| 128 | 7072789 | 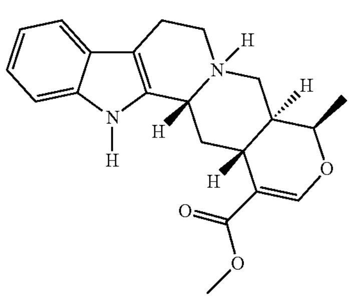 | 353.445 |

TABLE 2-continued

Additional Pubescine Derivatives

| ID | PUBCHEM COMPOUND CID | STRUCTURE | MW |
|---|---|---|---|
| 129 | 7072792 | 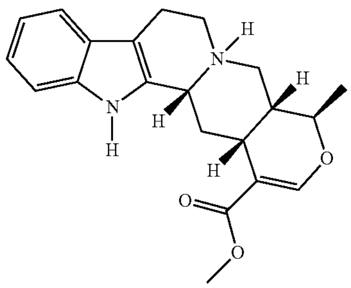 | 353.445 |
| 130 | 11870461 | 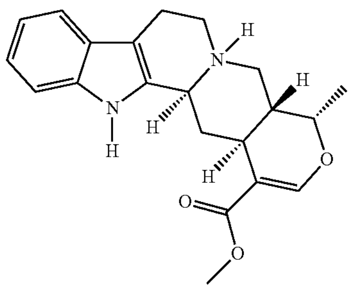 | 353.445 |
| 131 | 11871583 | 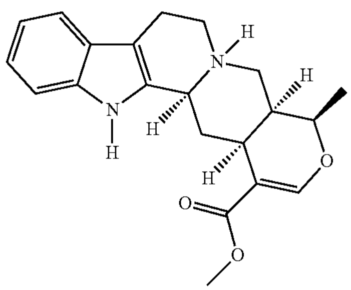 | 353.445 |
| 132 | 11871584 | 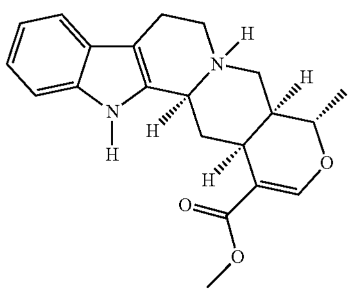 | 353.445 |
| 133 | 23681623 | 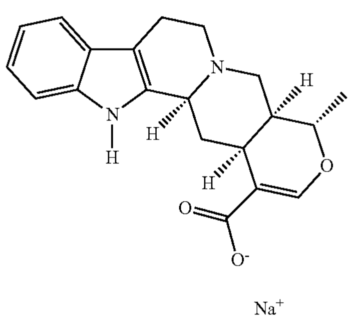 [SMILES: C[C@@H]1OC=C(C(=O)[O-])[C@H]2C[C@H]3c4[nH]c5ccccc5c4CCN3C[C@@H]12 ; [Na+]] | 360.392 |

TABLE 2-continued

Additional Pubescine Derivatives

| ID | PUBCHEM COMPOUND CID | STRUCTURE | MW |
|---|---|---|---|
| 134 | 3061398 | 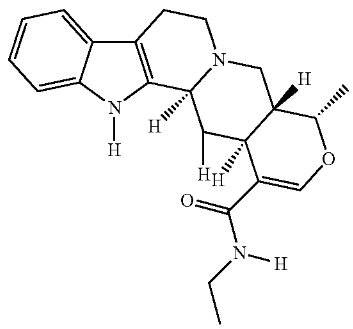 [SMILES: CCNC(=O)C1=CO[C@@H](C)[C@H]2CN3CCc4c([nH]c5ccccc45)[C@@H]3C[C@H]12] | 365.479 |
| 135 | 3036058 | 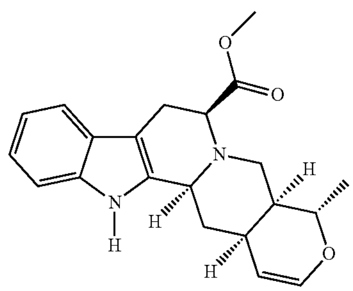 [SMILES: COC(=O)[C@@H]1Cc2c([nH]c3ccccc23)[C@@H]2C[C@@H]3C=CO[C@@H](C)[C@@H]3CN12] | 366.42 |
| 136 | 6336137 | 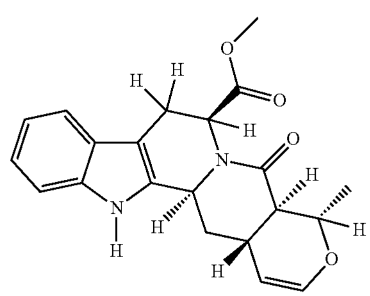 [SMILES: COC(=O)[C@@H]1Cc2c([nH]c3ccccc23)[C@@H]2C[C@H]3C=CO[C@@H](C)[C@@H]3C(=O)N12] | 366.42 |
| 137 | 25109981 | 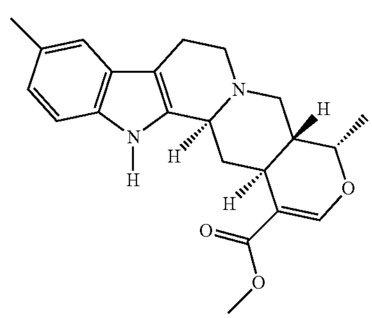 | 366.464 |
| 138 | 20054968 | 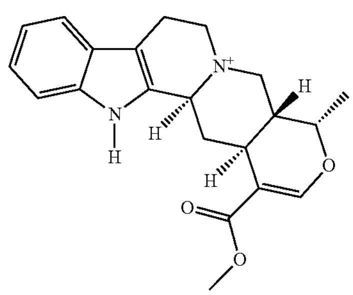 [SMILES: COC(=O)C1=CO[C@@H](C)[C@H]2C[NH+]3CCc4c([nH]c5ccccc45)[C@@H]3C[C@H]12] | 367.472 |

TABLE 2-continued

Additional Pubescine Derivatives

| ID | PUBCHEM COMPOUND CID | STRUCTURE | MW |
|---|---|---|---|
| 139 | 5319994 | 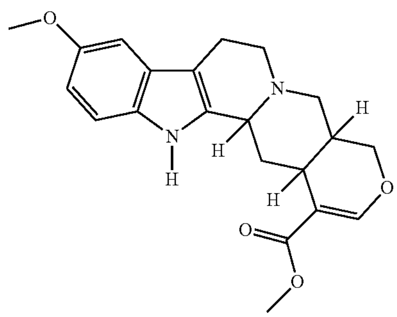 [SMILES: COC(=O)C1=COCC2CN3CCc4c([nH]c5ccc(OC)cc45)C3CC12] | 368.436 |
| 140 | 15837430 | 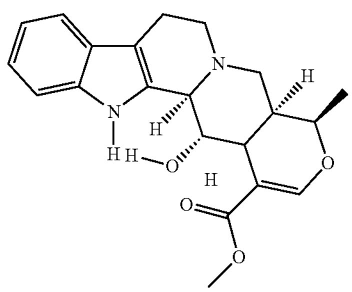 | 368.436 |
| 141 | 20056472 | 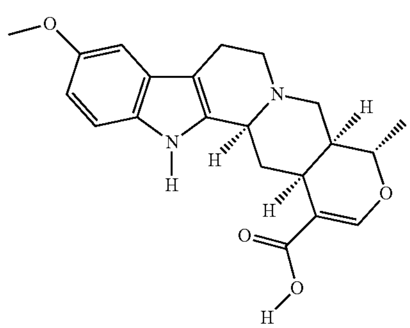 | 368.436 |
| 142 | 21115135 | 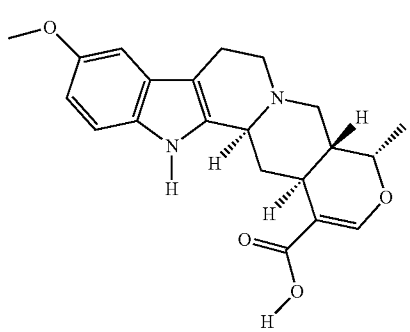 | 368.436 |

TABLE 2-continued

Additional Pubescine Derivatives

| ID | PUBCHEM COMPOUND CID | STRUCTURE | MW |
|---|---|---|---|
| 143 | 21586699 | 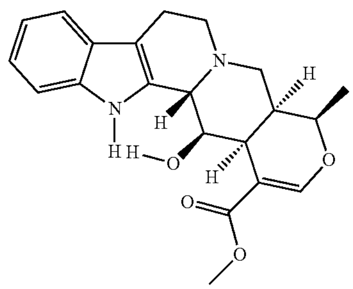 [SMILES: COC(=O)C1=CO[C@H](C)[C@@H]2CN3CCc4c([nH]c5ccccc45)[C@H]3[C@H](O)[C@H]12] | 368.436 |
| 144 | 21634908 | 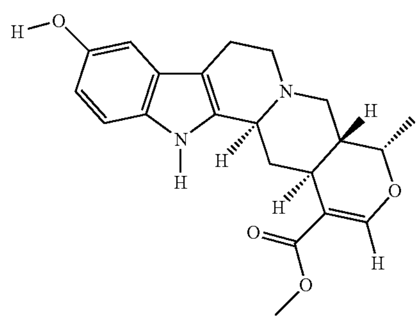 [SMILES: COC(=O)C1=CO[C@@H](C)[C@H]2CN3CCc4c([nH]c5ccc(O)cc45)[C@@H]3C[C@H]12] | 368.436 |
| 145 | 21634909 | 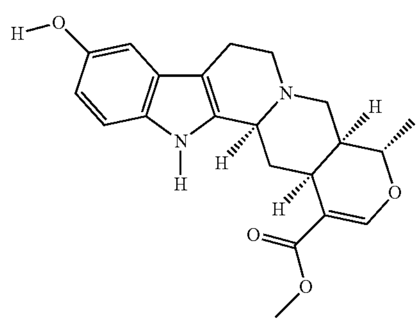 [SMILES: COC(=O)C1=CO[C@@H](C)[C@@H]2CN3CCc4c([nH]c5ccc(O)cc45)[C@@H]3C[C@H]12] | 368.436 |
| 146 | 21634910 | 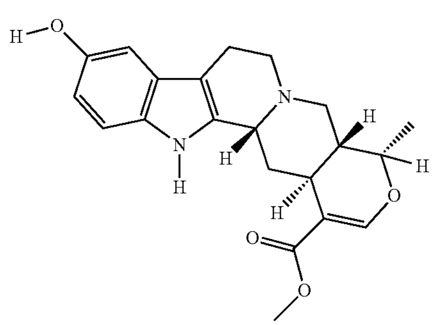 [SMILES: COC(=O)C1=CO[C@@H](C)[C@H]2CN3CCc4c([nH]c5ccc(O)cc45)[C@H]3C[C@H]12] | 368.436 |

TABLE 2-continued
Additional Pubescine Derivatives
| ID | PUBCHEM COMPOUND CID | STRUCTURE | MW |
|---|---|---|---|
| 147 | 21634911 | 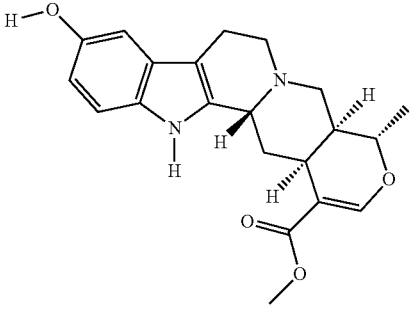 [SMILES: COC(=O)C1=CO[C@@H](C)[C@@H]2CN3CCc4c([nH]c5ccc(O)cc45)[C@H]3C[C@H]12] | 368.436 |
| 148 | 21634912 | 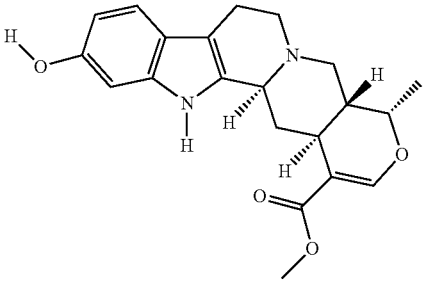 [SMILES: COC(=O)C1=CO[C@@H](C)[C@H]2CN3CCc4c([nH]c5cc(O)ccc45)[C@@H]3C[C@H]12] | 368.436 |
| 149 | 21634913 | 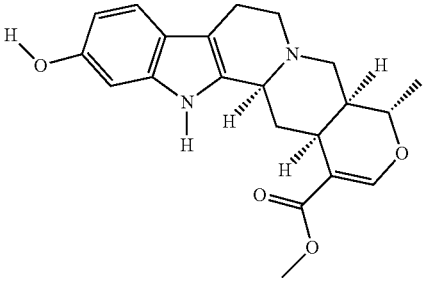 [SMILES: COC(=O)C1=CO[C@@H](C)[C@@H]2CN3CCc4c([nH]c5cc(O)ccc45)[C@@H]3C[C@H]12] | 368.436 |
| 150 | 21634914 | 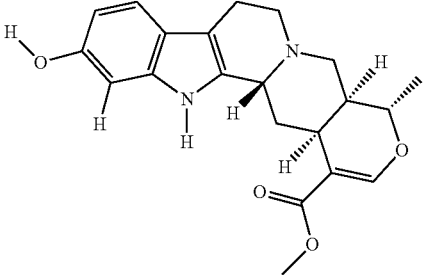 [SMILES: COC(=O)C1=CO[C@@H](C)[C@@H]2CN3CCc4c([nH]c5cc(O)ccc45)[C@H]3C[C@H]12] | 368.436 |
| 151 | 21636096 | 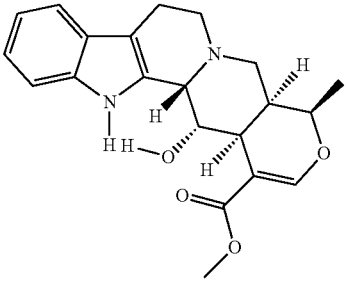 [SMILES: COC(=O)C1=CO[C@H](C)[C@@H]2CN3CCc4c([nH]c5ccccc45)[C@H]3[C@@H](O)[C@H]12] | 368.436 |

TABLE 2-continued
Additional Pubescine Derivatives
| ID | PUBCHEM COMPOUND CID | STRUCTURE | MW |
|---|---|---|---|
| 152 | 11057920 | 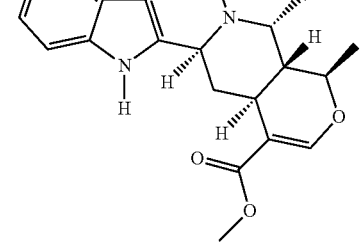 | 377.447 |
| 153 | 11079363 | 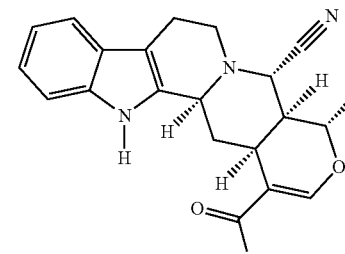 | 377.447 |
| 154 | 21763836 | 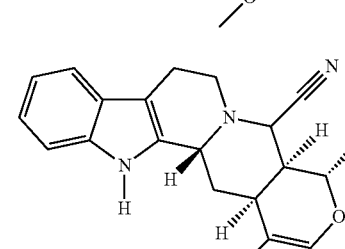 | 377.447 |
| 155 | 72313 | 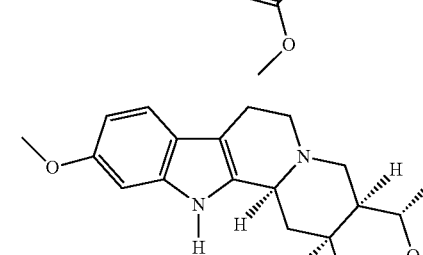 | 382.464 |
| 156 | 72339 | 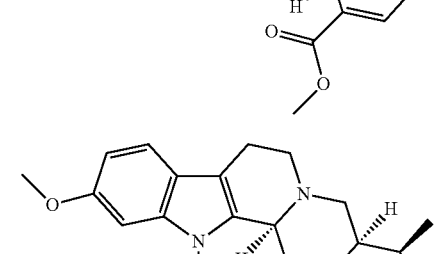 | 382.464 |

TABLE 2-continued

Additional Pubescine Derivatives

| ID | PUBCHEM COMPOUND CID | STRUCTURE | MW |
|---|---|---|---|
| 157 | 95501 | 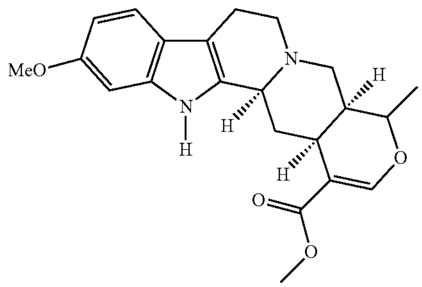 [SMILES: COC(=O)C1=COC(C)[C@@H]2CN3CCc4c([nH]c5cc(OC)ccc45)[C@@H]3C[C@H]12] | 382.464 |
| 159 | 251563 | 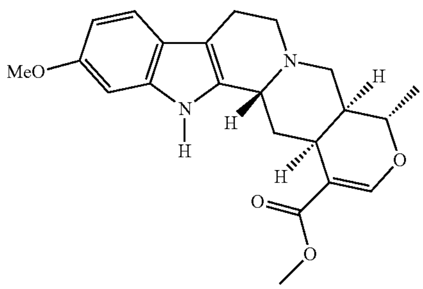 [SMILES: COC(=O)C1=CO[C@@H](C)[C@@H]2CN3CCc4c([nH]c5cc(OC)ccc45)[C@H]3C[C@H]12] | 382.464 |
| 160 | 251575 | 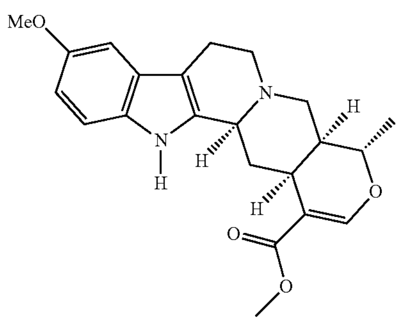 [SMILES: COC(=O)C1=CO[C@@H](C)[C@@H]2CN3CCc4c([nH]c5ccc(OC)cc45)[C@@H]3C[C@H]12] | 382.464 |
| 161 | 354380 | 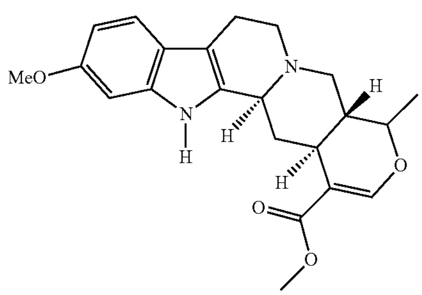 [SMILES: COC(=O)C1=COC(C)[C@H]2CN3CCc4c([nH]c5cc(OC)ccc45)[C@@H]3C[C@H]12] | 382.464 |
| 162 | 443030 | 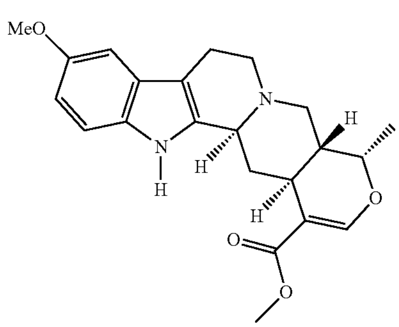 [SMILES: COC(=O)C1=CO[C@@H](C)[C@H]2CN3CCc4c([nH]c5ccc(OC)cc45)[C@@H]3C[C@H]12] | 382.464 |

TABLE 2-continued
Additional Pubescine Derivatives
| ID | PUBCHEM COMPOUND CID | STRUCTURE | MW |
|---|---|---|---|
| 163 | 1403337 | 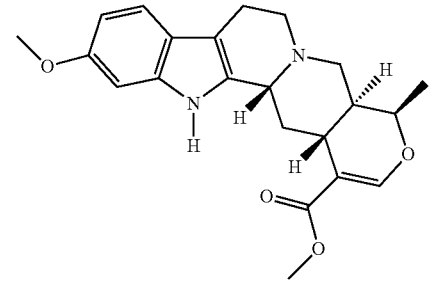 | 382.464 |
| 164 | 3483176 | 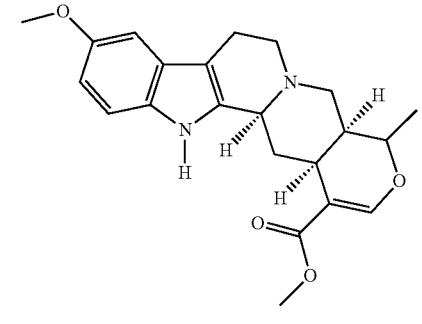 | 382.464 |
| 165 | 4529448 | 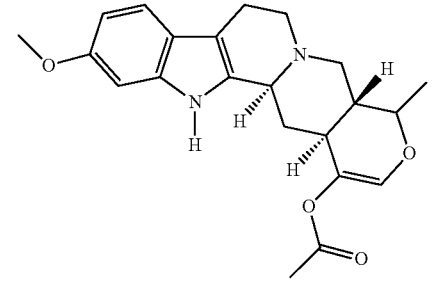 | 382.464 |
| 166 | 6553934 | 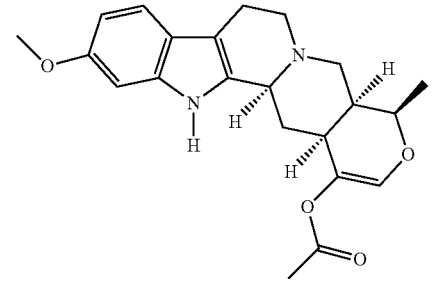 | 382.464 |
| 167 | 6732860 | 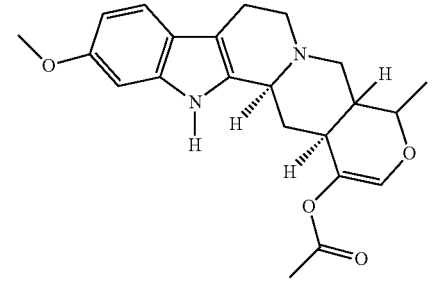 | 382.464 |

TABLE 2-continued

Additional Pubescine Derivatives

| ID | PUBCHEM COMPOUND CID | STRUCTURE | MW |
|---|---|---|---|
| 168 | 7565650 | 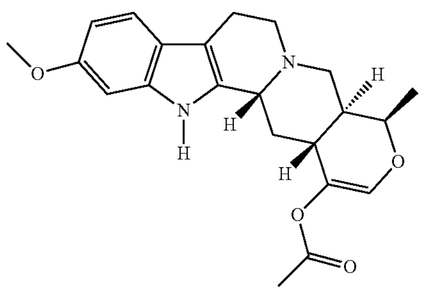 | 382.464 |
| 169 | 7565665 | 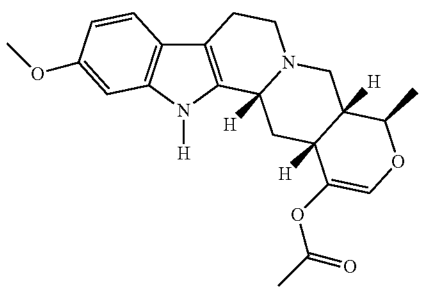 | 382.464 |
| 170 | 11908402 | 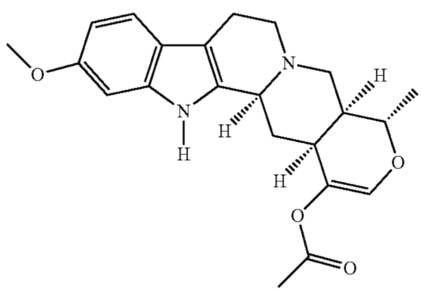 | 382.464 |
| 171 | 11908404 | 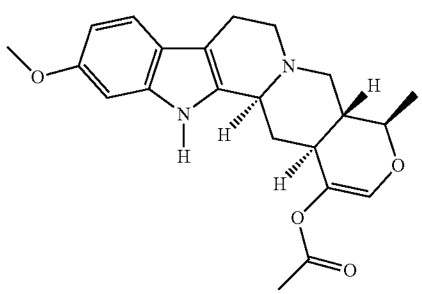 | 382.464 |
| 172 | 11908406 | 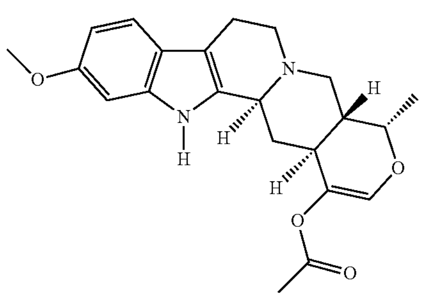 | 382.464 |

TABLE 2-continued
Additional Pubescine Derivatives
| ID | PUBCHEM COMPOUND CID | STRUCTURE | MW |
|---|---|---|---|
| 173 | 21117085 | 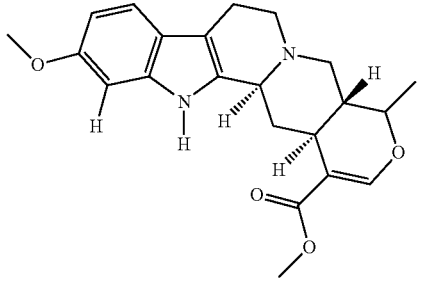 | 382.464 |
| 174 | 40493520 | 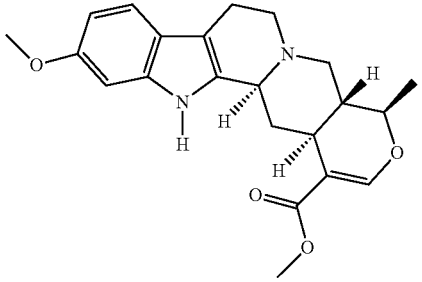 | 382.464 |
| 175 | 3055402 | 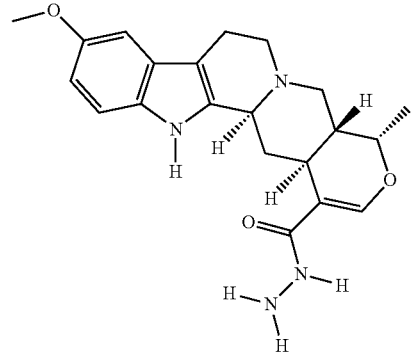 | 382.466 |
| 176 | 1597078 | 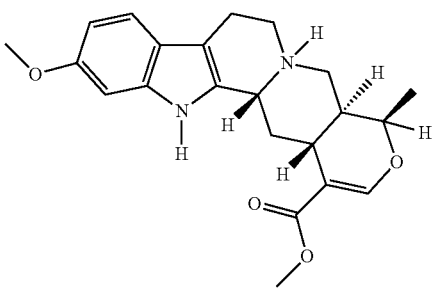 | 383.471 |

TABLE 2-continued

Additional Pubescine Derivatives

| ID | PUBCHEM COMPOUND CID | STRUCTURE | MW |
|---|---|---|---|
| 177 | 6562597 | 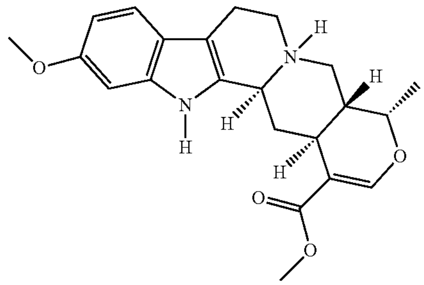 | 383.471 |
| 178 | 6984601 | 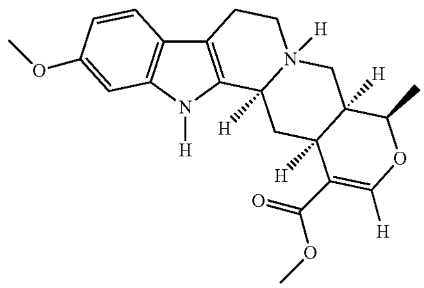 | 383.471 |
| 179 | 7565649 | 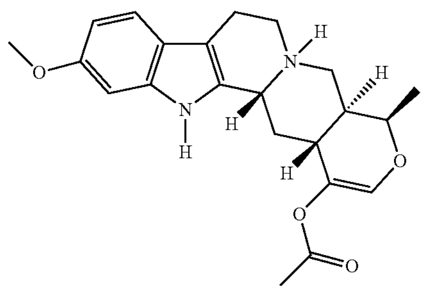 | 383.471 |
| 180 | 7565664 | 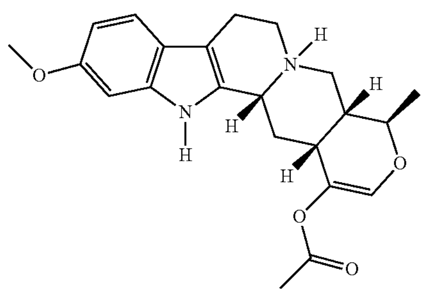 | 383.471 |
| 181 | 11862127 | 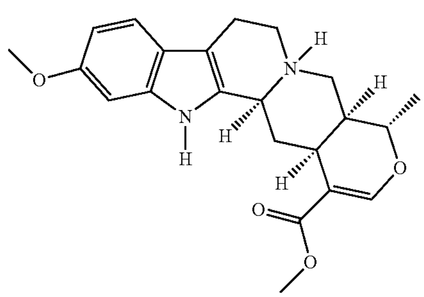 | 383.471 |

TABLE 2-continued

Additional Pubescine Derivatives

| ID | PUBCHEM COMPOUND CID | STRUCTURE | MW |
|---|---|---|---|
| 182 | 11908400 | 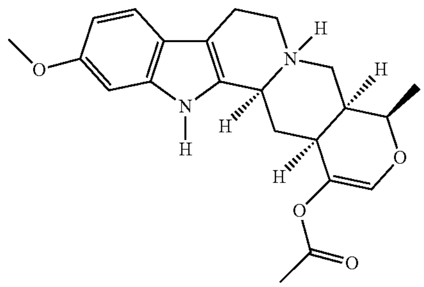 | 383.471 |
| 183 | 11908401 | 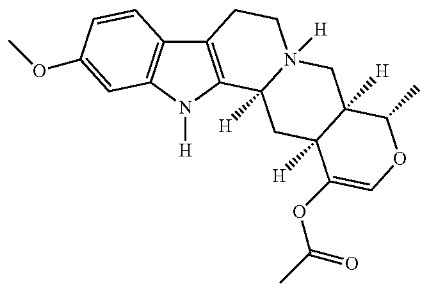 | 383.471 |
| 184 | 11908403 | 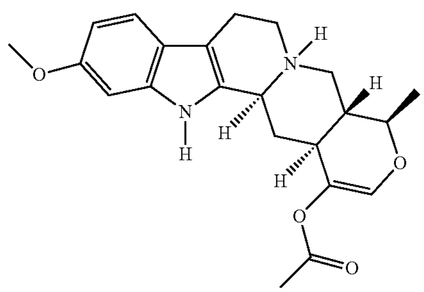 | 383.471 |
| 185 | 11908405 | 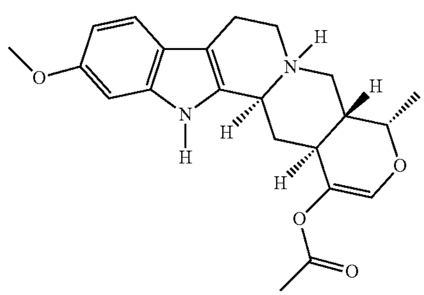 | 383.471 |
| 186 | 40493519 | 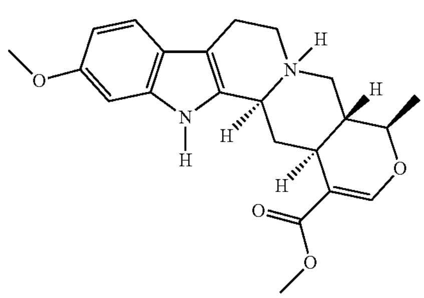 | 383.471 |

TABLE 2-continued
| | Additional Pubescine Derivatives | | |
|---|---|---|---|
| ID | PUBCHEM COMPOUND CID | STRUCTURE | MW |
| 187 | 25109980 | 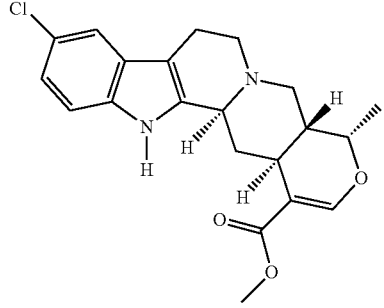 [SMILES: COC(=O)C1=CO[C@@H](C)[C@H]2CN3CCc4c([nH]c5ccc(Cl)cc45)[C@@H]3C[C@H]12] | 386.882 |
| 188 | 168978 | 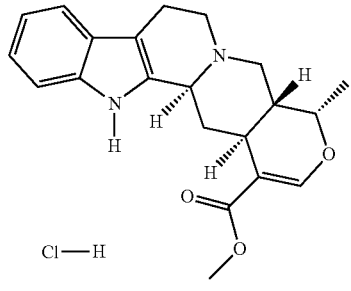 [SMILES: COC(=O)C1=CO[C@@H](C)[C@H]2CN3CCc4c([nH]c5ccccc45)[C@@H]3C[C@H]12 ; Cl] | 388.898 |
| 189 | 353514 | 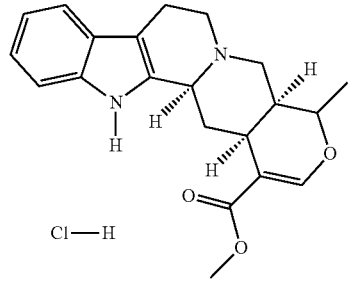 [SMILES: COC(=O)C1=COC(C)[C@@H]2CN3CCc4c([nH]c5ccccc45)[C@@H]3C[C@H]12 ; Cl] | 388.898 |
| 190 | 21124741 | 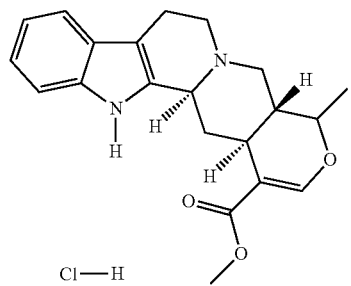 [SMILES: COC(=O)C1=COC(C)[C@H]2CN3CCc4c([nH]c5ccccc45)[C@@H]3C[C@H]12 ; Cl] | 388.898 |

TABLE 2-continued

Additional Pubescine Derivatives

| ID | PUBCHEM COMPOUND CID | STRUCTURE | MW |
|---|---|---|---|
| 191 | 3061384 | 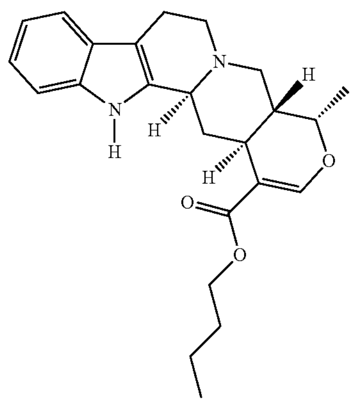 [SMILES: CCCCOC(=O)C1=CO[C@@H](C)[C@H]2CN3CCc4c([nH]c5ccccc45)[C@@H]3C[C@H]12] | 394.518 |
| 192 | 3055405 | 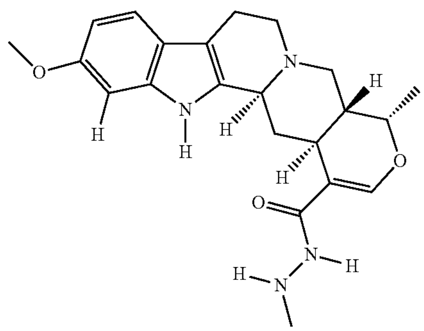 | 396.493 |
| 193 | 21115237 | 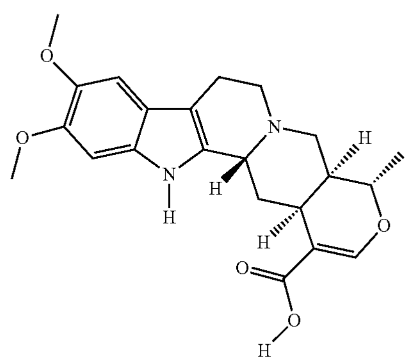 | 398.463 |
| 194 | 3060112 | 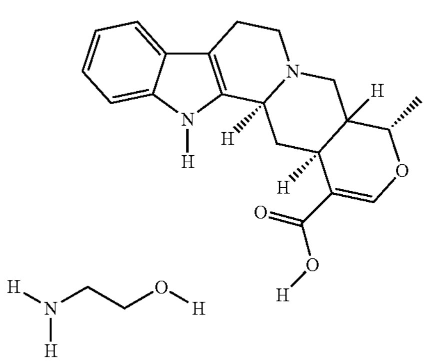 | 399.494 |

TABLE 2-continued

Additional Pubescine Derivatives

| ID | PUBCHEM COMPOUND CID | STRUCTURE | MW |
|---|---|---|---|
| 195 | 3061397 | 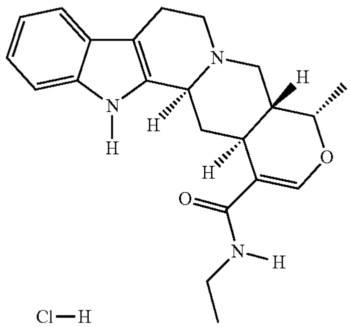 [SMILES: CCNC(=O)C1=CO[C@@H](C)[C@H]2CN3CCc4c([nH]c5ccccc45)[C@@H]3C[C@H]12 ; Cl] | 401.94 |
| 196 | 3060114 | 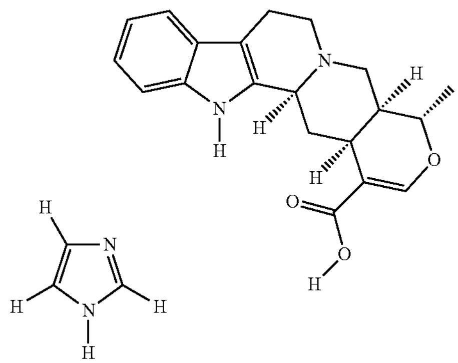 [SMILES: c1c[nH]cn1 ; C[C@@H]1OC=C(C(=O)O)[C@H]2C[C@H]3c4[nH]c5ccccc5c4CCN3C[C@@H]12] | 406.489 |
| 197 | 21636098 | 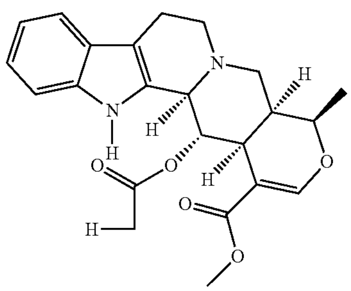 [SMILES: COC(=O)C1=CO[C@H](C)[C@@H]2CN3CCc4c([nH]c5ccccc45)[C@@H]3[C@@H](OC(C)=O)[C@H]12] | 410.474 |
| 198 | 21769030 | 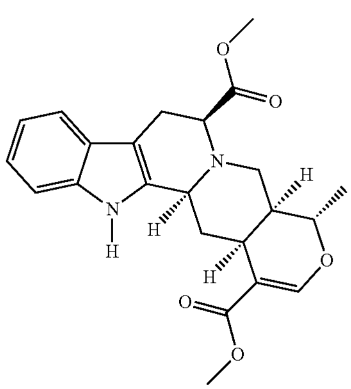 [SMILES: COC(=O)C1=CO[C@@H](C)[C@@H]2CN3[C@H](C(=O)OC)Cc4c([nH]c5ccccc45)[C@@H]3C[C@H]12] | 410.474 |

TABLE 2-continued

Additional Pubescine Derivatives

| ID | PUBCHEM COMPOUND CID | STRUCTURE | MW |
|---|---|---|---|
| 199 | 67228 | 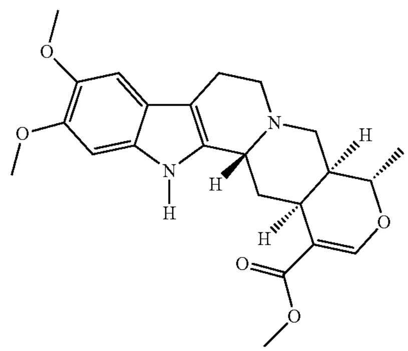 | 412.49 |
| 200 | 161345 | 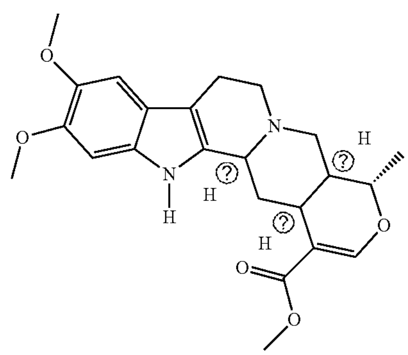 | 412.49 |
| 201 | 201052 | 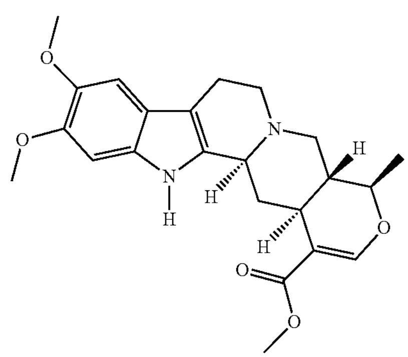 | 412.49 |
| 202 | 234846 | 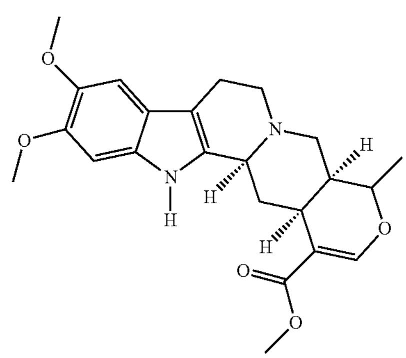 | 412.49 |

TABLE 2-continued

Additional Pubescine Derivatives

| ID | PUBCHEM COMPOUND CID | STRUCTURE | MW |
|---|---|---|---|
| 203 | 3085270 | 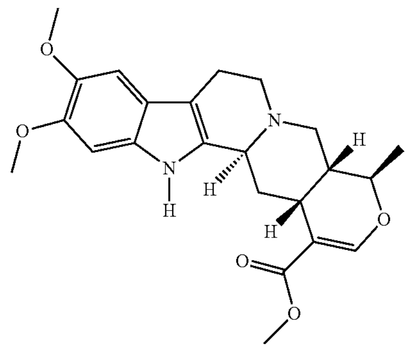 | 412.49 |
| 204 | 5320929 | 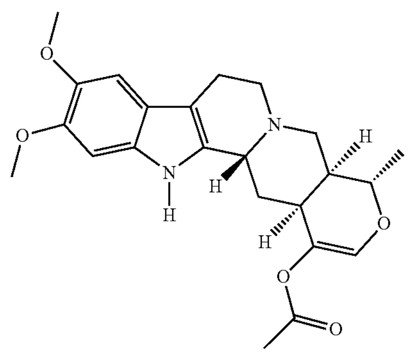 | 412.49 |
| 205 | 11742418 | 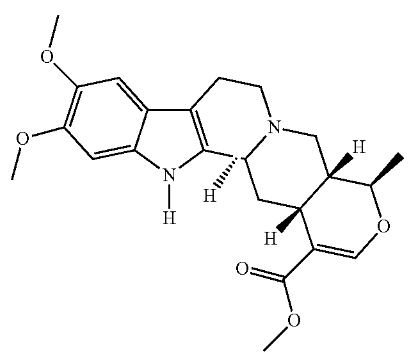 | 412.49 |
| 206 | 21127010 | 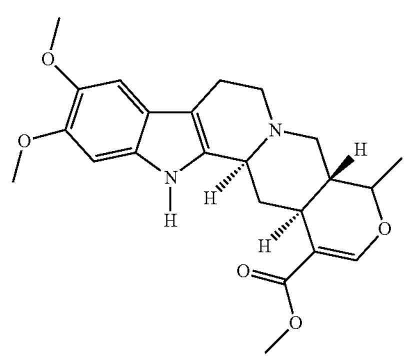 | 412.49 |

TABLE 2-continued

Additional Pubescine Derivatives

| ID | PUBCHEM COMPOUND CID | STRUCTURE | MW |
|---|---|---|---|
| 207 | 21595047 | 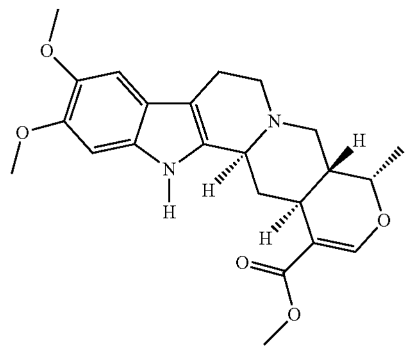 | 412.49 |
| 208 | 40492910 | 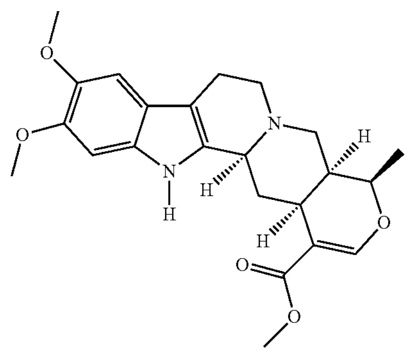 | 412.49 |
| 209 | 3053963 | 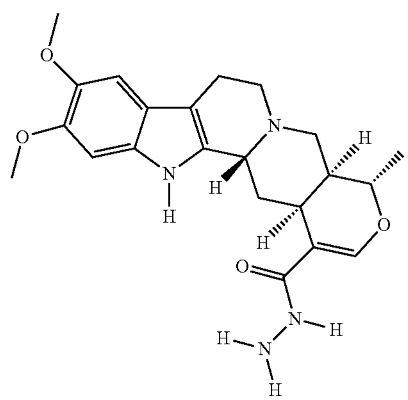 | 412.493 |
| 210 | 21595046 | 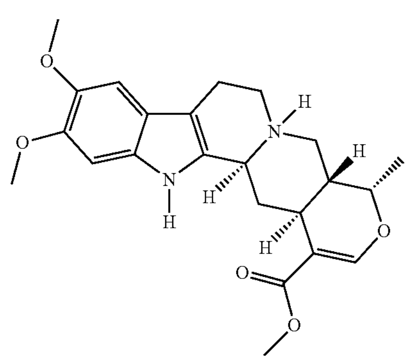 | 413.498 |

TABLE 2-continued
Additional Pubescine Derivatives
| ID | PUBCHEM COMPOUND CID | STRUCTURE | MW |
|---|---|---|---|
| 211 | 40492909 | 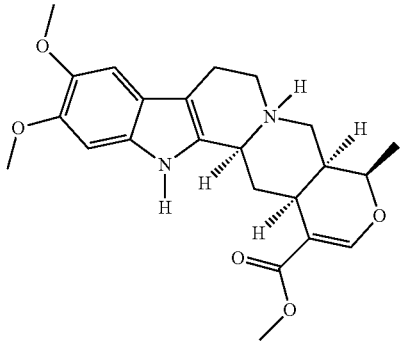 | 413.498 |
| 212 | 40492911 | 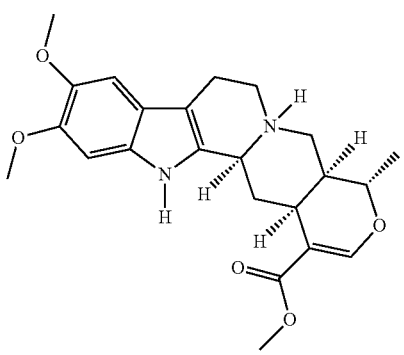 | 413.498 |
| 213 | 40492912 | 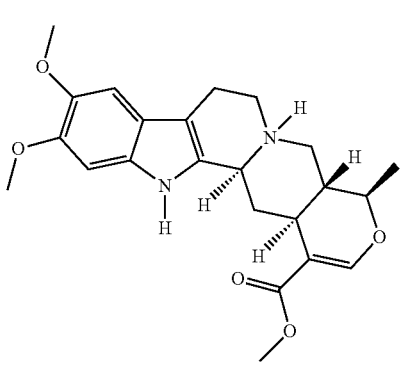 | 413.498 |
| 214 | 3036057 | 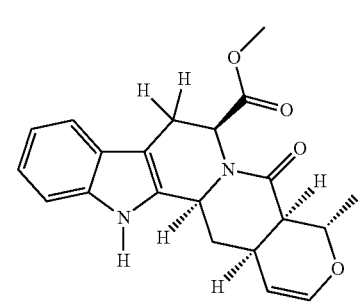 | 424.501 |

TABLE 2-continued

Additional Pubescine Derivatives

| ID | PUBCHEM COMPOUND CID | STRUCTURE | MW |
|---|---|---|---|
| 215 | 3055401 | 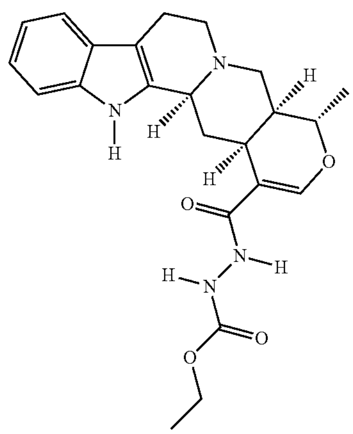 [SMILES: CCOC(=O)NNC(=O)C1=CO[C@@H](C)[C@@H]2CN3CCc4c([nH]c5ccccc45)[C@@H]3C[C@H]12] | 424.504 |
| 216 | 3055441 | 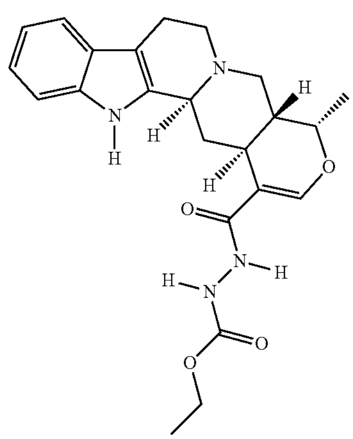 [SMILES: CCOC(=O)NNC(=O)C1=CO[C@@H](C)[C@H]2CN3CCc4c([nH]c5ccccc45)[C@@H]3C[C@H]12] | 424.504 |
| 217 | 3055399 | 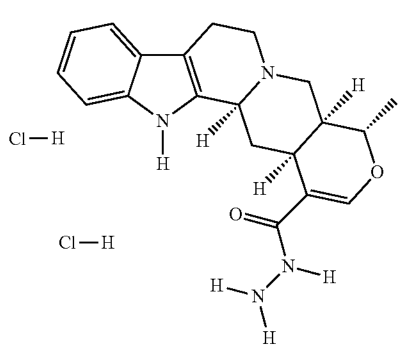 | 425.362 |

TABLE 2-continued
Additional Pubescine Derivatives
| ID | PUBCHEM COMPOUND CID | STRUCTURE | MW |
|---|---|---|---|
| 218 | 3061383 | 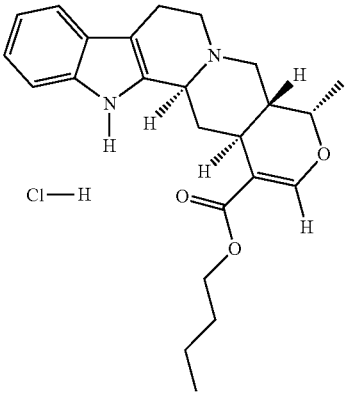 | 430.979 |
| 219 | 3085269 | 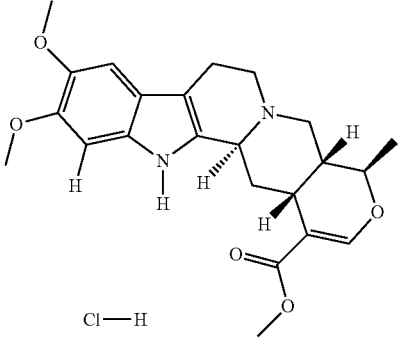 | 448.951 |
| 220 | 21155989 | 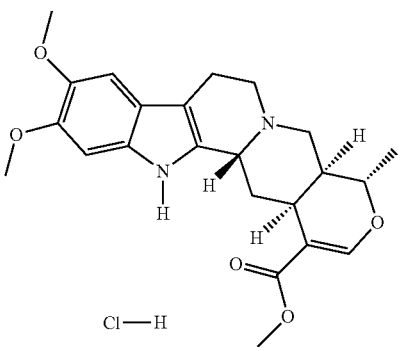 | 448.951 |

TABLE 2-continued

| | Additional Pubescine Derivatives | | |
|---|---|---|---|
| ID | PUBCHEM COMPOUND CID | STRUCTURE | MW |
| 221 | 3043985 | | 449.598 |
| 222 | 2055400 | | 460.965 |
| 223 | 3088 | | 469.586 |

TABLE 2-continued

Additional Pubescine Derivatives

| ID | PUBCHEM COMPOUND CID | STRUCTURE | MW |
|---|---|---|---|
| 224 | 71464 | 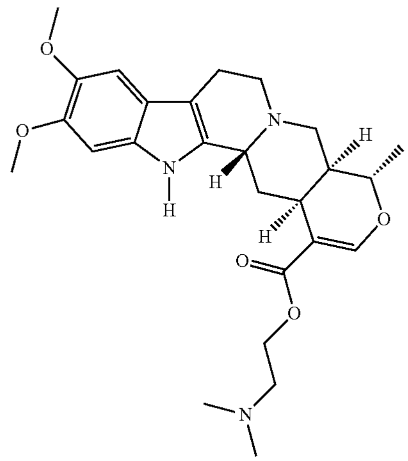 | 469.586 |
| 225 | 21115035 | 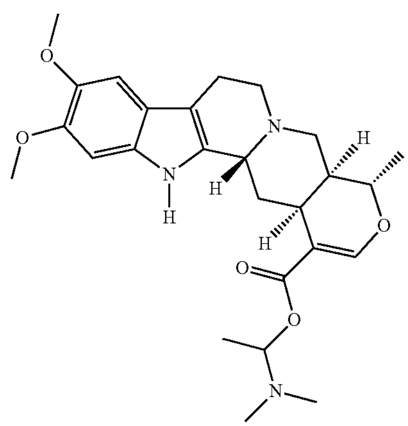 | 469.586 |
| 226 | 3043984 | 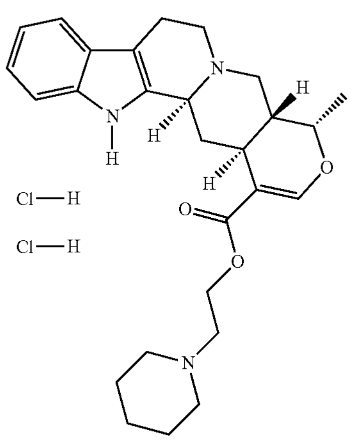 | 522.52 |

TABLE 2-continued

Additional Pubescine Derivatives

| ID | PUBCHEM COMPOUND CID | STRUCTURE | MW |
|---|---|---|---|
| 227 | 71463 | 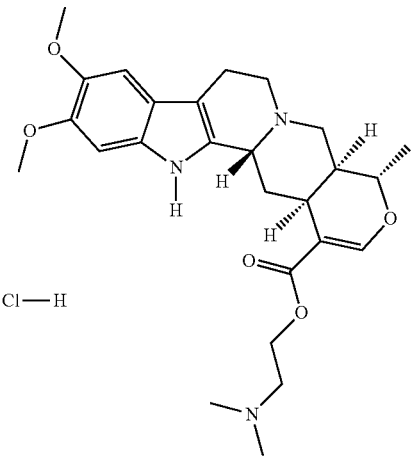 | 542.508 |
| 228 | 188431 | 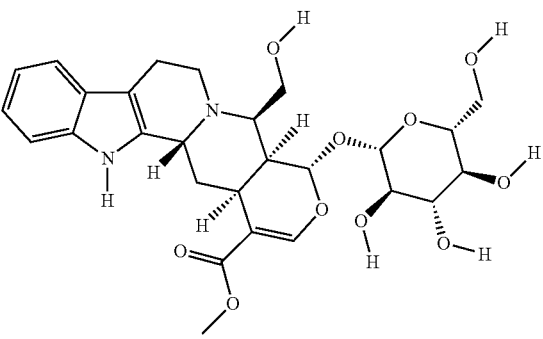 [SMILES: COC(=O)C1=CO[C@@H](O[C@@H]2O[C@H](CO)[C@@H](O)[C@H](O)[C@H]2O)[C@H]2[C@@H]1C[C@@H]1c3[nH]c4ccccc4c3CCN1[C@H]2CO] | 546.579 |

Example 3

MelanoDerm™ Pigmentation Assay

The compounds of the invention were tested in the MelanoDerm™ pigmentation assay, to confirm and demonstrate their activity as modulators or promoters in a setting that replicates in vivo conditions. MelanoDerm™, made by MatTek Corp., is a viable reconstituted three-dimensional human skin equivalent containing normal melanocytes and keratinocytes that are derived from African-American (MEL-B), Asian (MEL-A) or Caucasian (MEL-C) donors. Both MEL-A and MEL-B tissues were used in the current study, and they were maintained in the NMM-113 medium as recommended by the manufacturer.

Pubescine (from Sigma) was dissolved in 30% ethanol: 70% propylene glycol to a final concentration of 1.0 mM (equal to 356.6 μg/ml), and this was maintained constant and used on all samples tested. A 25 μl of its aliquot was applied topically to the MelanoDerm™ tissue (MEL-B) on Days 0, 1, 3, 6, 8 and 10. The MelanoDerm™ tissues were fed every other day with 5 ml fresh NMM-113. Prior to each application, the tissues were washed with 1 ml PBS to remove any residual test compound. Tissues were fixed on Days 10 and 13 for microscopic analysis and histological evaluation. In addition, duplicate tissues were frozen on Days 10 and 13 for the melanin assay.

Similar experiments were performed on Asian skin equivalent (MEL-A) except: the treatments were applied on Days 0, 1, 3, 6, 8, 10 and 13. Tissues were taken out on Days 13 and 16 for the various assays. 30% ethanol: 70% propylene glycol was used as a negative control and the well-known pigmentation inhibitor, arbutin (at concentration of 3 mg/ml), was used as a positive control.

The experiments were repeated twice on both MEL-A and MEL-B tissues from different lots to make sure that the results are reproducible (study 1 or 2). For each experiment, six tissues were treated with pubescine, and six were treated with vesicle (30% ethanol: 70% PEG) or arbutin if applicable. For MEL-B, on day 10, three tissues under each treatment condition were taken out, and one was used for histological studies and the other two were used for the melanin assay. The same protocol was followed with the MEL-B samples after 13 days' treatment and MEL-A after either 13 or 16 days' treatments.

For the histological studies:

Procedure 1: the effects of pubescine on melanin synthesis in MEL-A or B were evaluated by light microscopy (views from the top surface of the tissue).

Procedure 2: the distribution of melanin in the treated-MEL-A or B was accessed by image analysis using Fontana-Masson stained histological sections (views from the side of the tissue).

For the melanin tissues, the melanin content of each individual tissue was determined, and the final data show the average melanin content of 2 tissues treated under identical conditions.

Figure 5:
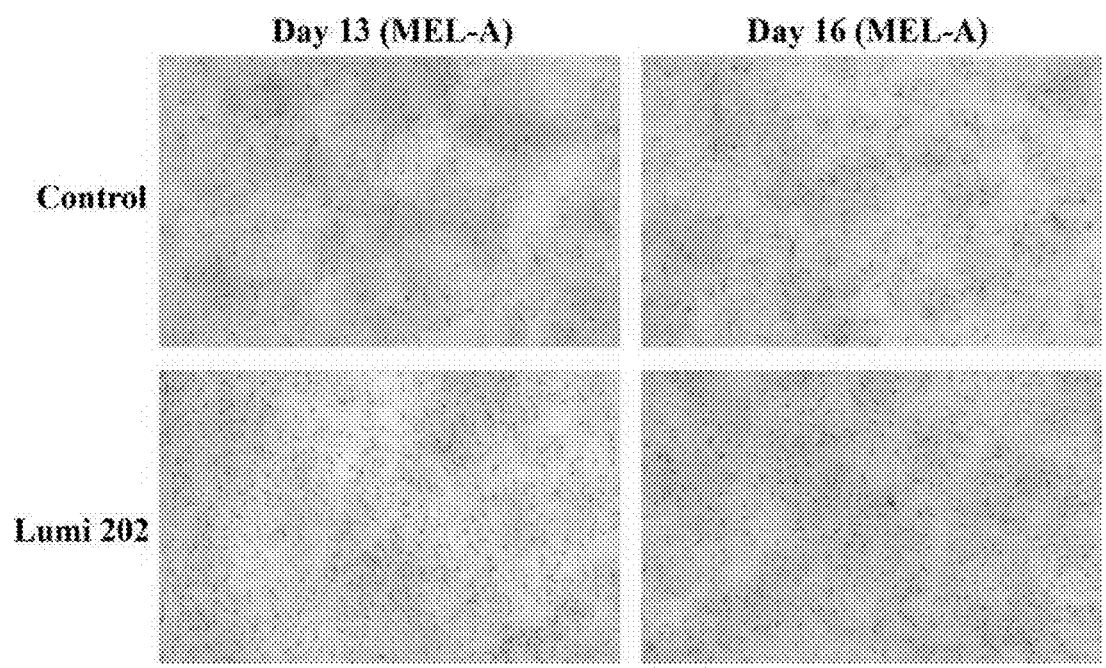
FIG. 5 presents the effect of Pubescine on Asian Skin Equivalent (MEL-A) (Lumi 202 is Pubescine).
Figure 6:
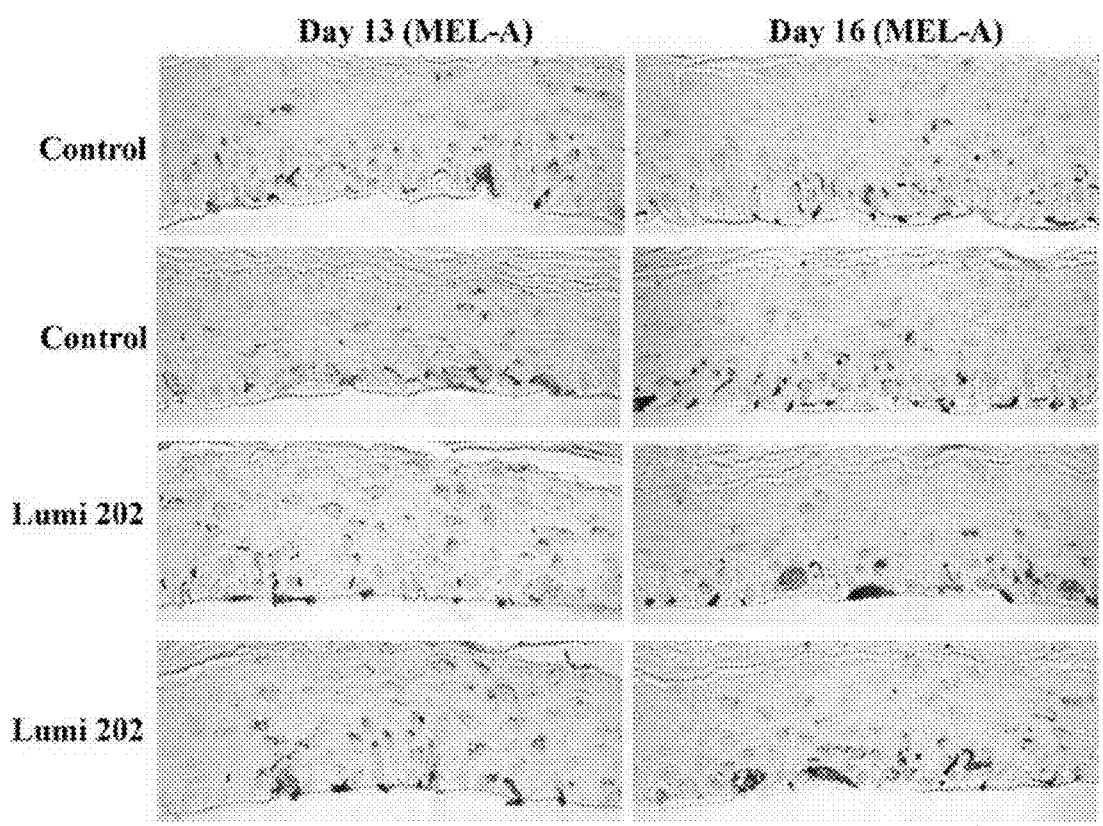
FIG. 6 presents Fontana-Masson Staining indicating that pubescine treatment results in an increase in the melanin content of Asian skin equivalent (MEL-A) (Lumi 202 is Pubescine).
Figure 7:
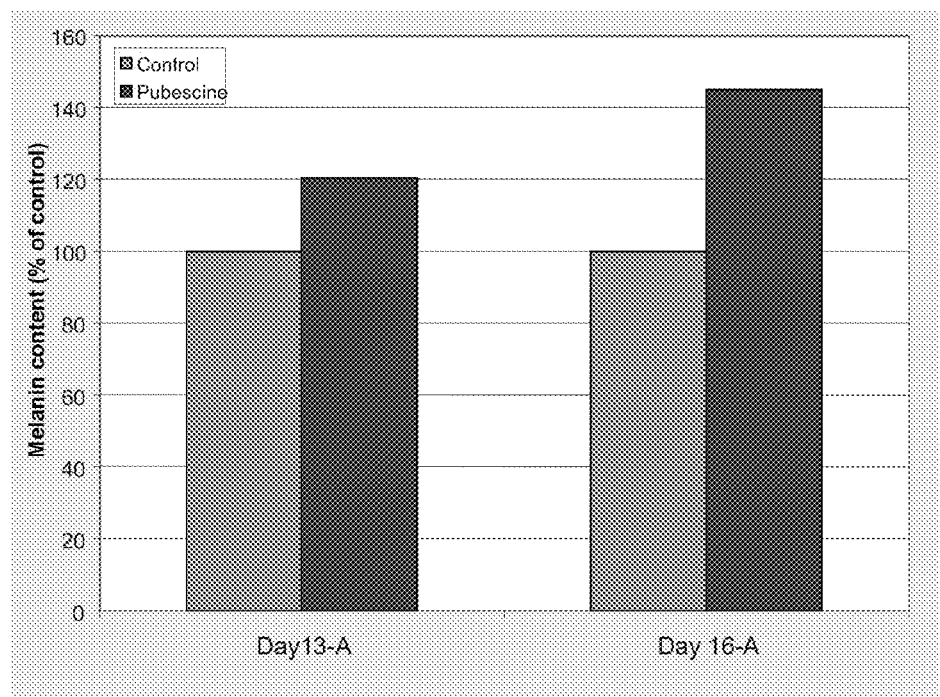
FIG. 7 shows that Melanin content of Asian skin equivalent (MEL-A) increases ~40% with pubescine treatment.
Figure 7:
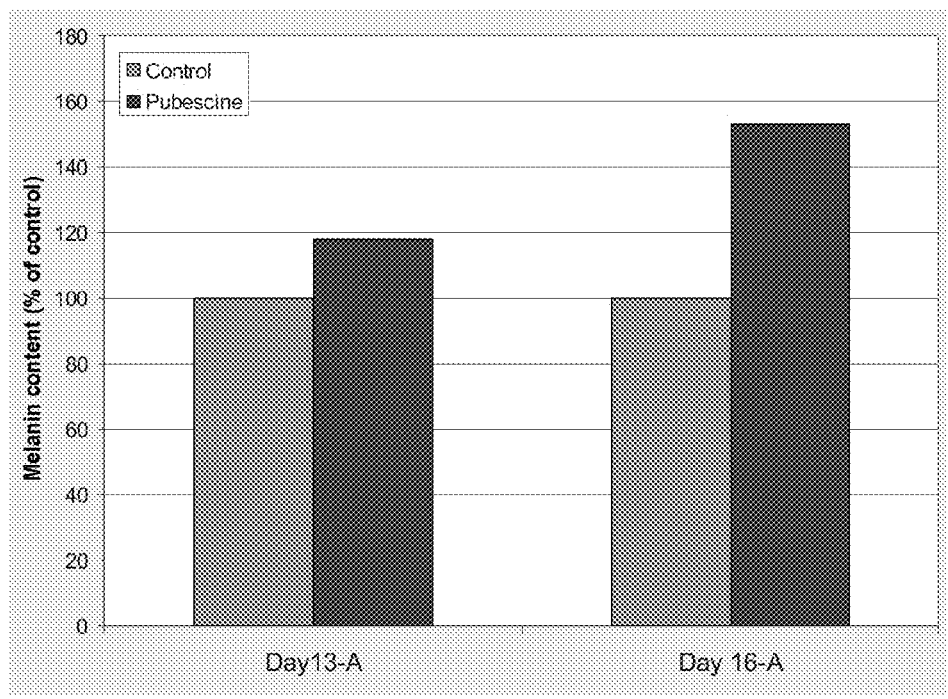

The results of the assays of both skin equivalents are set forth in FIGS. 5-6, and clearly demonstrate that the compounds of the invention achieve skin darkening in all of the samples tested.

Example 4

Effects of Pubescine on Cellular Levels of Tyr Gene Family Proteins and Gp100 in Melan-a Cells As tyrosinase plays a central role in melanogenesis, many depigmenting compounds act via effects on the expression, processing, maturation, degradation and enzymatic activity of this enzyme (Parvez, S., et al. *Phytother. Res.* 20, 921-934 (2006) and Solano, F., et al. *Pigment Cell Res.* 19, 550-571 (2006). Several assays were performed to determine whether pubescine affected tyrosinase expression, processing, maturation, degradation and enzymatic activity.

The effect of pubescine on tyrosinase activity was studied in vitro using melan-a cell lysates.

Tyrosinase activity assay was performed in triplicate on melan-a cell lysates as previously described (Orlow et al. 1990).

Figure 3:
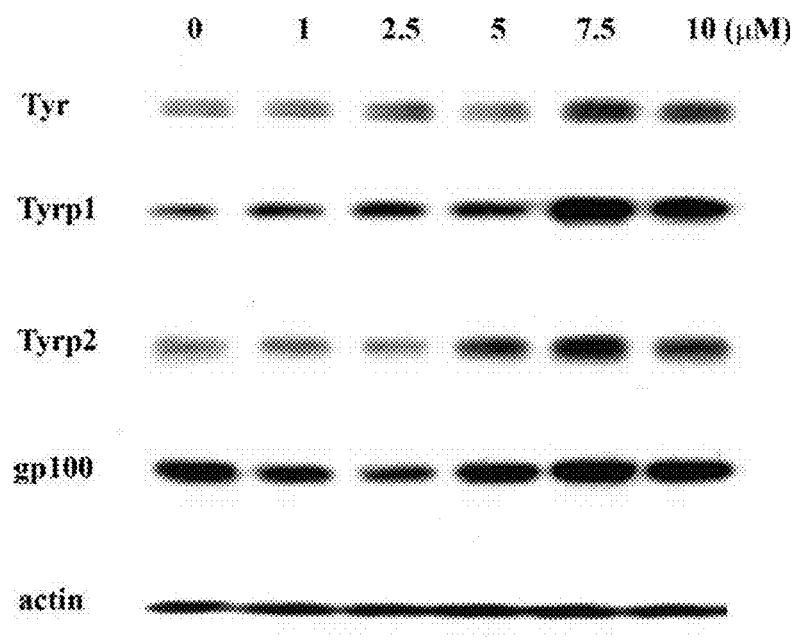
FIG. 3 presents effects of Pubescine on Cellular Levels of Tyr Gene Family Proteins and gp100 in Melan-a Cells.

Melan-a cells were incubated with various concentrations of pubescine for 72 hrs. Cell lysates were prepared and separated by 7.5% sodium dodecyl sulfate-polyacrylamide gel and transferred to Immobilon-P membranes. Tyrosinase gene family proteins were detected with antibodies against each protein. The results are set forth in the gel of FIG. 3.

The results show that Pubescine increases cellular levels of tyrosinase family proteins and gp100 in a dose-dependent manner.

Example 5

Figure 4A:
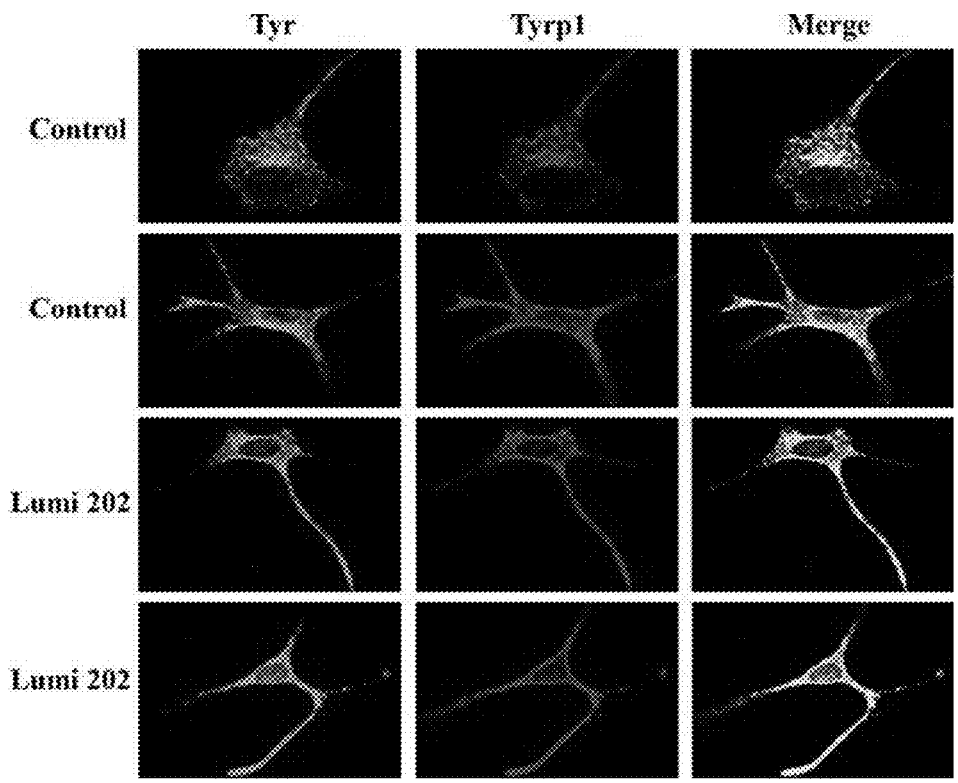
FIGS. 4A and 4B show that Pubescine does not alter the sub-cellular localization Tyr, Tryp-1 or Lamp-1 in melan-a cells (Lumi 202 is Pubescine).
Figure 4B:
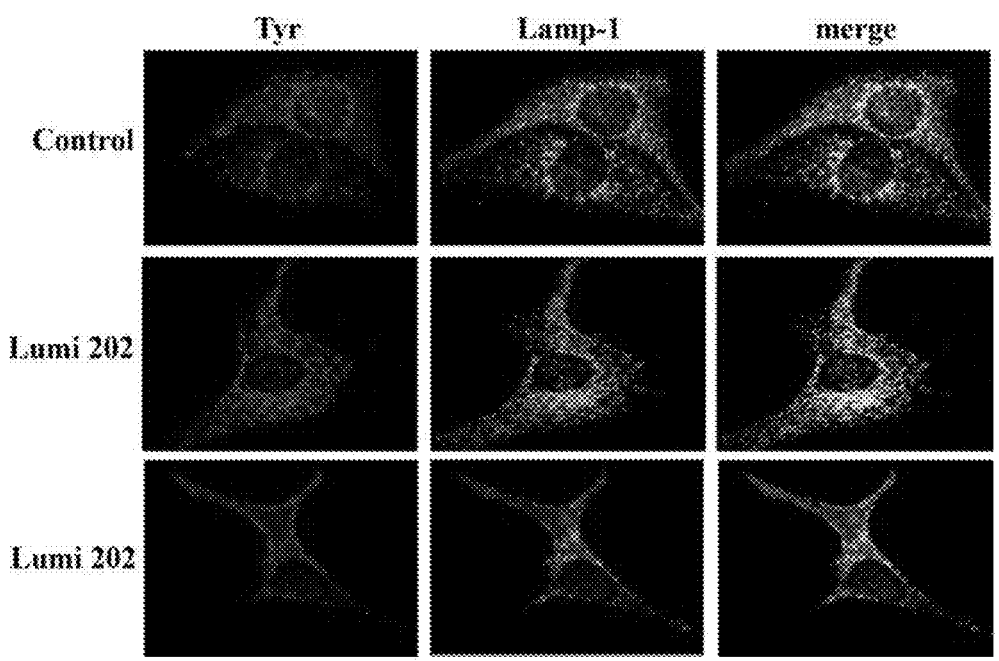

The Effect of Pubescine on Sub-Cellular Localization Tyr, Tryp-1 or Lamp-1 in Melan-a Cells Cells were cultured on cover slips, incubated with or without 10 μM pubescine for 72 hrs at 37° C. The cells were fixed with −20° C. methanol for 5 min and stained by immunofluorescence with antibodies for Tyr, Tyrp-1 and/or Lamp-1. The slides were analyzed with a confocal microscope (LSM 510, Zeiss). The results show that Pubescine does not alter the sub-cellular localization Tyr, Tryp-1 or Lamp-1 in melan-a cells (FIGS. 4A and 4B).

While certain of the preferred embodiments have been described and specifically exemplified above, it is not intended that the invention be limited to such embodiments. Various modifications may be made thereto without departing from the scope and spirit of the present invention, as set forth in the following claims.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds given in this application were generated using various commercially available chemical naming software tools including MDL's ISIS Draw Autonom Software tool, and were not verified. Particularly, in the event of inconsistency, the depicted structure governs.

What is claimed is:

1. A method for increasing the melanin content in a mammalian subject in need thereof, comprising administering to said mammal a melanin content-increasing amount of i) an indole alkaloid compound; or ii) a plant extract containing pubescine;

wherein the indole alkaloid compound is according to formula I:

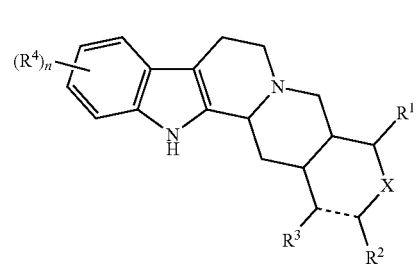

wherein
X is O or $CR^5$;
$R^1$ is selected from the group consisting of hydrogen, hydroxy, substituted or unsubstituted ($C_1$-$C_6$) alkyl, and substituted or unsubstituted ($C_1$-$C_6$) alkoxy;
$R^2$ is selected from the group consisting of hydrogen, hydroxy, substituted or unsubstituted ($C_1$-$C_6$) alkyl, substituted or unsubstituted acyloxy, and substituted or unsubstituted ($C_1$-$C_6$) alkoxy;
$R^3$ is selected from the group consisting of hydrogen, hydroxy, substituted or unsubstituted ($C_1$-$C_6$) alkyl, substituted or unsubstituted acyloxy, substituted or unsubstituted ($C_1$-$C_6$) alkoxy, carboxy, substituted or unsubstituted alkoxycarbonyl, and substituted or unsubstituted amido;
$R^4$ is selected from the group consisting of hydroxy, substituted or unsubstituted ($C_1$-$C_6$) alkyl, substituted or unsubstituted ($C_1$-$C_6$) alkoxy, and halo;
$R^5$ is selected from the group consisting of hydrogen, hydroxy, substituted or unsubstituted ($C_1$-$C_6$) alkyl, substituted or unsubstituted acyloxy, substituted or unsubstituted ($C_1$-$C_6$) alkoxy;
n is 0, 1, 2, 3, or 4; and the dotted bond is a single or a double bond;
or pharmaceutically acceptable salts, solvates, stereo isomers, tautomers, isotopic variants or prodrugs thereof.

2. The method of claim 1, wherein the compound is according to formula II:

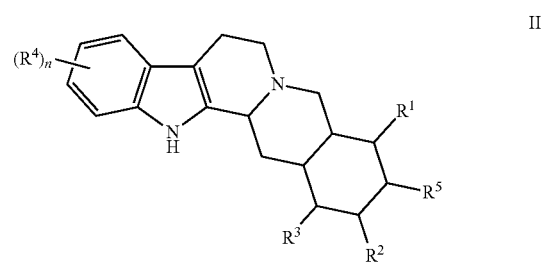

wherein $R^1$-$R^5$, and n are as in claim 1; or a pharmaceutically acceptable salt, solvate, stereo isomer, tautomer, isotopic variant or prodrug thereof.

3. The method according to claim 1, wherein $R^5$ is H, OH, substituted or unsubstituted ($C_1$-$C_6$) alkoxy, or $OCOR^6$; and $R^6$ is OH, substituted or unsubstituted ($C_1$-$C_6$) alkyl, substituted or unsubstituted aryl, or substituted or unsubstituted heteroaryl.

4. The method according to claim 1, wherein $R^5$ is H, OH, OMe, OCOPh, OC(O)-(3,4,5-trimethoxyphen-1-yl), OCOMe, or $OCOCH_2COMe$.

5. The method of claim 1, wherein the compound is according to formula III:

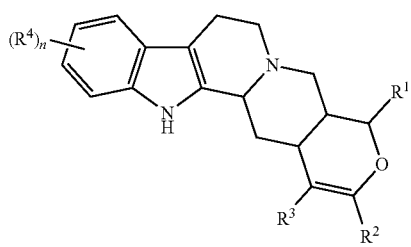

wherein $R^1$-$R^4$, and n are as in claim 1; or a pharmaceutically acceptable salt, solvate, stereo isomer, tautomer, isotopic variant or prodrug thereof.

6. The method according to claim 1, wherein $R^1$ is H, OH, OMe, Me, or Et.

7. The method according to claim 1, wherein $R^2$ is H, OH, substituted or unsubstituted acyloxy, and substituted or unsubstituted ($C_1$-$C_6$) alkoxy.

8. The method according to claim 1, wherein $R^3$ is $CO_2H$, $CO_2Me$, $CO_2Et$, $C(O)OCH_2CH_2NH_2$, $C(O)OCH_2CH_2NMe_2$, $CONH_2$, CONHMe, CONHPh, $CONMe_2$, or $C(O)NHCH_2CH_2NH_2$.

9. The method according to claim 1, wherein n is 1 or 2; and each $R^4$ is independently F, Cl, Me, OMe or OEt.

10. The method of claim 1, wherein the compound is according to formula IV:

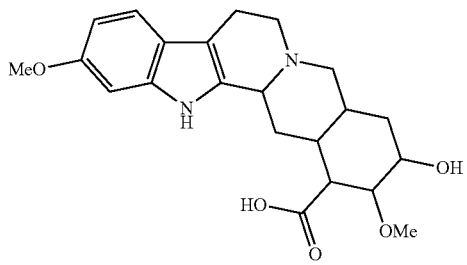

or a pharmaceutically acceptable salt, solvate, stereo isomer, tautomer, isotopic variant or prodrug thereof.

11. The method of claim 1, wherein the compound is according to formula V:

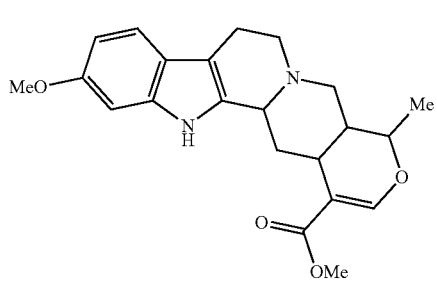

or a pharmaceutically acceptable salt, solvate, stereo isomer, tautomer, isotopic variant or prodrug thereof.

12. The method of claim 1, wherein the compound is resperic acid or pubescine.

13. A method for increasing the melanin content in a mammalian subject in need thereof, comprising administering to said mammal a melanin content-increasing amount of a compound; wherein the compound is selected from the group consisting of the following compounds:

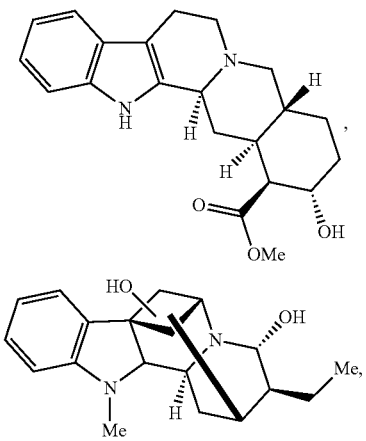

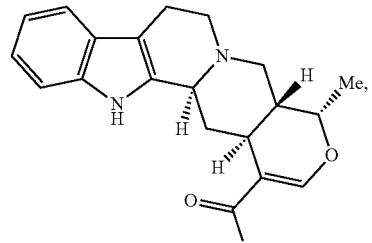

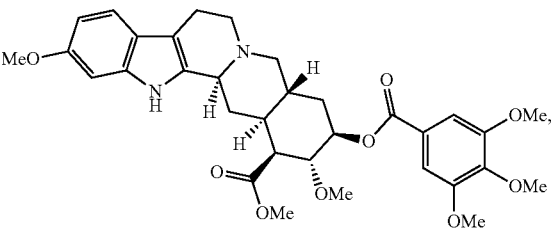

113
-continued
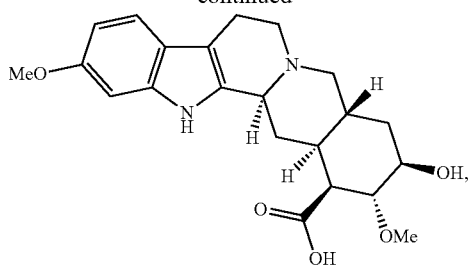
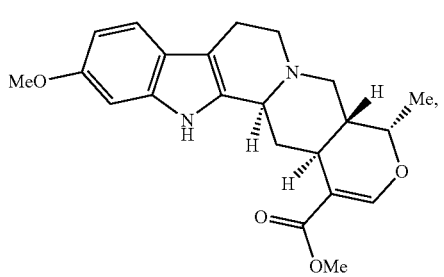
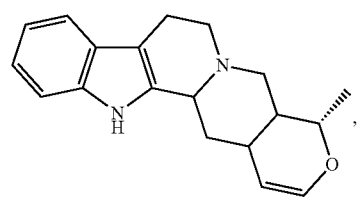
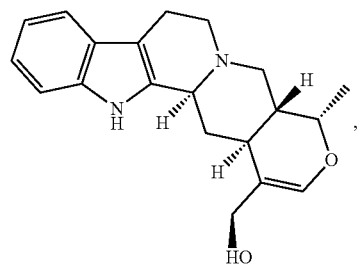
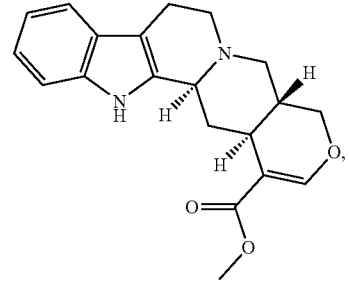
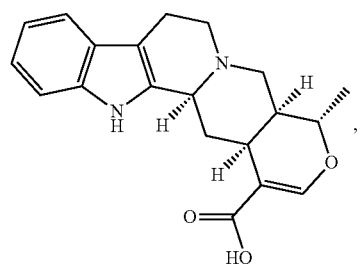
114
-continued
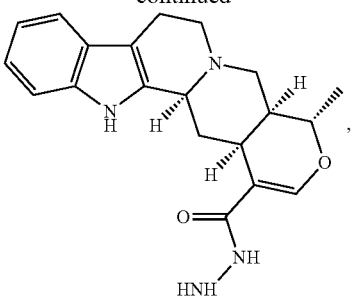
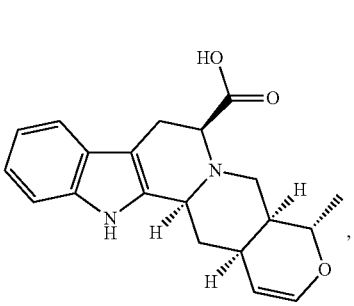
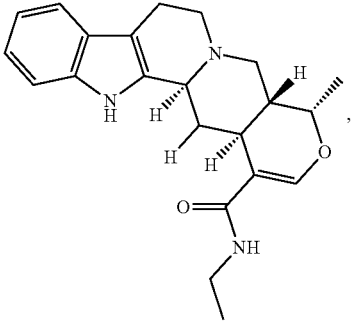
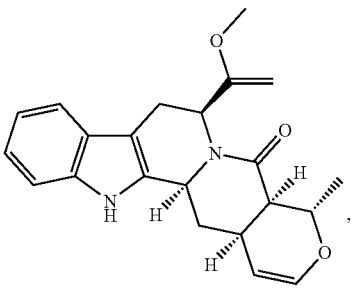
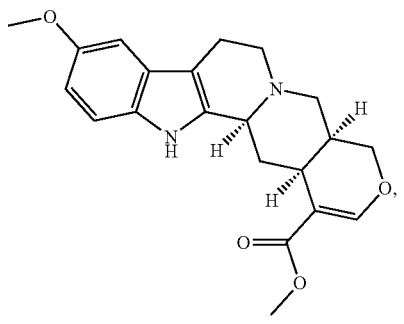

115
-continued
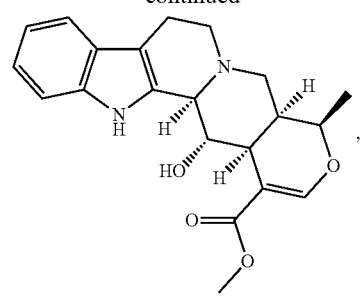
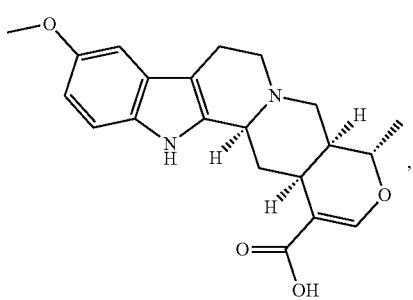
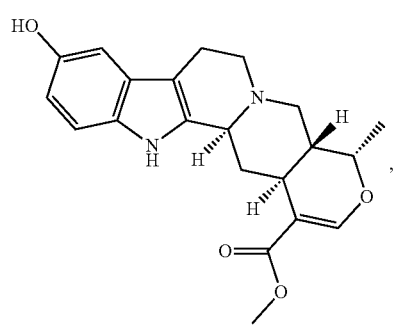
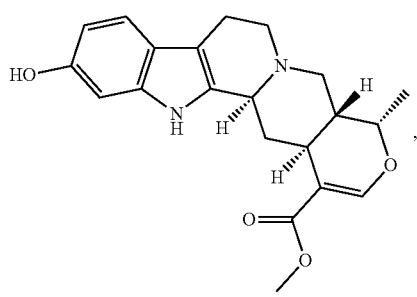
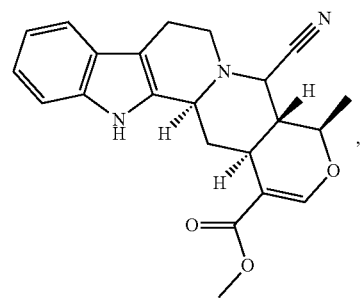
116
-continued
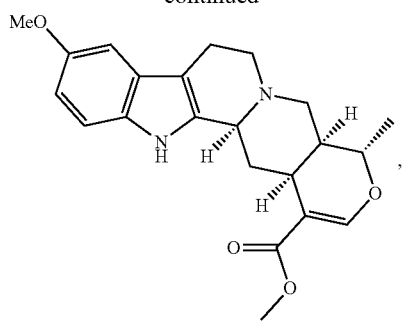
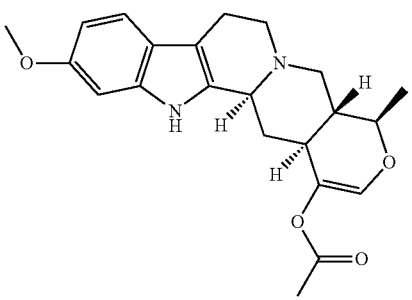
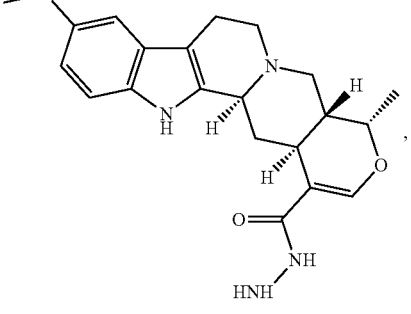
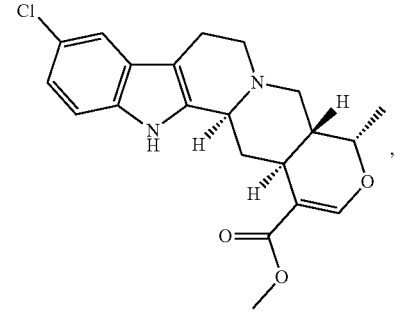
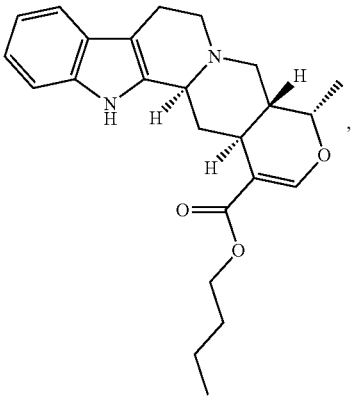

117
-continued
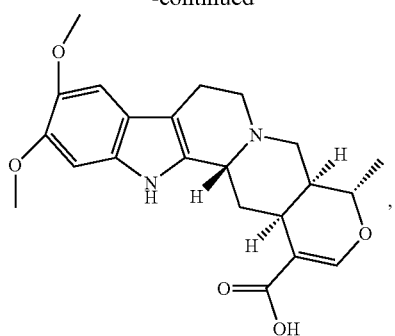
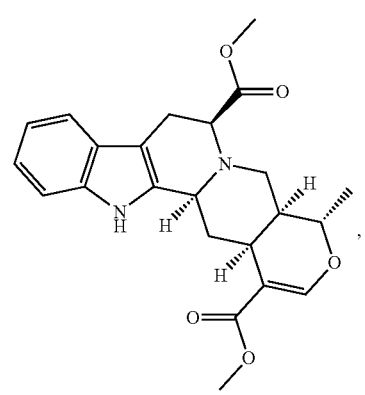
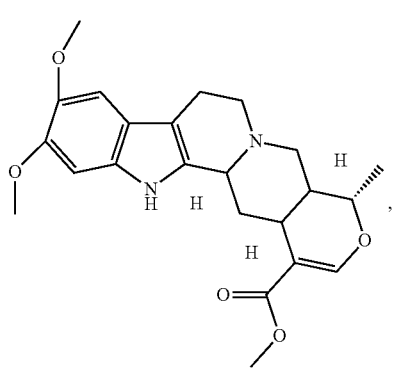
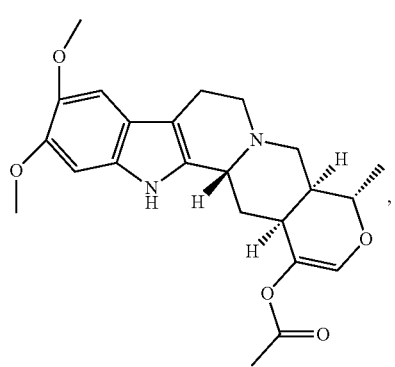
118
-continued
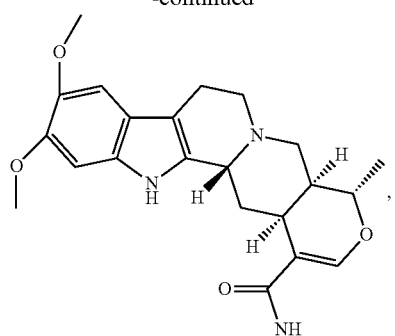
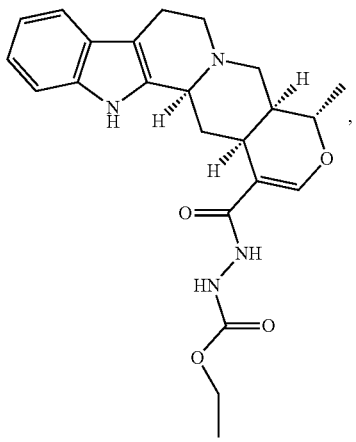
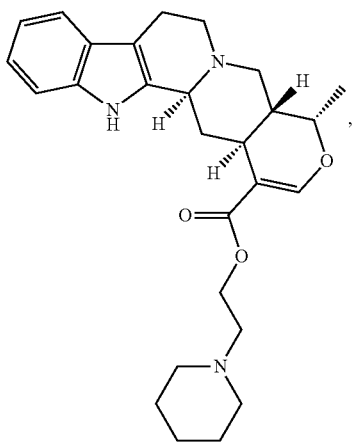
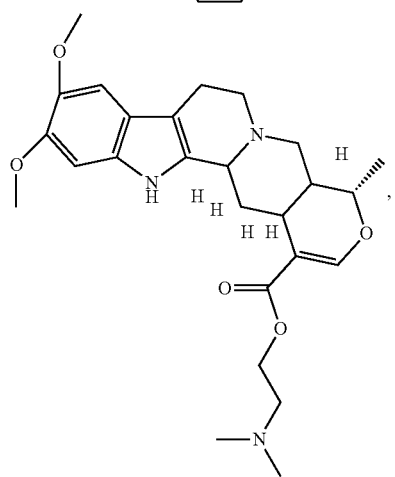

-continued

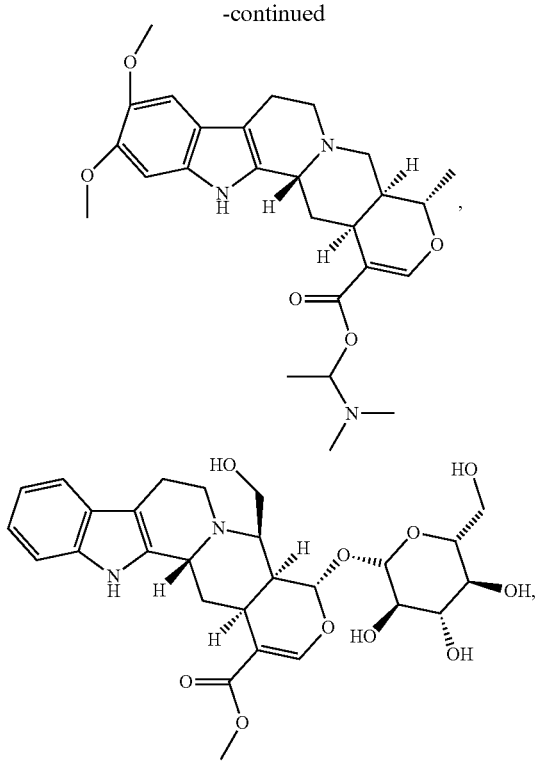

or a pharmaceutically acceptable salt, solvate, stereo isomer, tautomer, isotopic variant or prodrug thereof.

14. The method of claim 1, further comprising an additional active agent.

15. The method of claim 1, further comprising an additional active agent, and wherein the additional active agent is a pharmacological agent, a skin darkening agent, a skin tanning agent, another melanogenesis promoter, a tanning agent, a phosphodiesterase inhibitor, methylxanthine, cipamfylline, psoralen, flurocoumarin, a self tanning agent, or a dihydroxyacetone based tanner.

16. A method for treating, ameliorating or managing a disease or condition involving aberrant melanogenesis, which comprises administering to a patient in need or desirous of such treatment, amelioration or management, a therapeutically effective melanogenesis-enhancing amount of i) an indole alkaloid compound; or ii) a plant extract containing pubescine; and wherein the indole alkaloid compound is according to claim 1.

17. The method of claim 16, wherein the compound or the extract is administered to darken or increase pigmentation levels.

18. The method of claim 1, wherein the plant extract is derived from *Discaria pubescens*.

\* \* \* \* \*